US007749957B2

(12) United States Patent
Ittel et al.

(10) Patent No.: US 7,749,957 B2
(45) Date of Patent: Jul. 6, 2010

(54) CLAY-BINDING PEPTIDES AND METHODS OF USE

(75) Inventors: Steven Dale Ittel, Wilmington, DE (US); Scott D. Cunningham, Chadds Ford, PA (US); Pierre E. Rouviere, Wilimington, DE (US); Stephen R. Fahnestock, Wilmington, DE (US); John P. O'Brien, Oxford, PA (US); Eberhard Schneider, Denkte (DE); Gregor Schurmann, Hannover (DE); Peter Wagner, Braunschweig (DE)

(73) Assignee: E.I. du Pont de Nemours and Company, Wilmington, DE (US)

( * ) Notice: Subject to any disclaimer, the term of this patent is extended or adjusted under 35 U.S.C. 154(b) by 562 days.

(21) Appl. No.: 11/696,380

(22) Filed: Apr. 4, 2007

(65) Prior Publication Data

US 2007/0249805 A1 Oct. 25, 2007

Related U.S. Application Data

(60) Provisional application No. 60/790,149, filed on Apr. 6, 2006.

(51) Int. Cl.
*A61K 38/00* (2006.01)
*A61K 47/00* (2006.01)
*C09F 3/02* (2006.01)

(52) U.S. Cl. .......................... 514/2; 530/324; 530/227; 424/9.31

(58) Field of Classification Search ....................... None
See application file for complete search history.

(56) References Cited

U.S. PATENT DOCUMENTS

| | | | | |
|---|---|---|---|---|
| 6,057,429 | A * | 5/2000 | Bieniarz et al. | 530/402 |
| 2002/0098524 | A1 | 7/2002 | Murray et al. | |
| 2003/0148380 | A1 | 8/2003 | Belcher | |
| 2003/0185870 | A1 | 10/2003 | Grinstaff et al. | |
| 2005/0054752 | A1 | 3/2005 | O'Brien et al. | |
| 2006/0035223 | A1 | 2/2006 | Naik et al. | |
| 2006/0172282 | A1 | 8/2006 | Naik et al. | |

FOREIGN PATENT DOCUMENTS

| | | | |
|---|---|---|---|
| WO | WO 03/078451 | A2 | 9/2003 |
| WO | WO 03/102020 | A2 | 12/2003 |

OTHER PUBLICATIONS

Dashman, 1984, Soil Biol. Biochem., 16, 51-55.*
Fusi, 1989, Soil Biol. Biochem., 21, 911-920.*
Kalra, Sippy et al., Studies on the adsorption of peptides of glycine/alanine on montmorillonite clay with or without co-ordinated divalent cations, Colloids and Surfaces A: Physicochem. Eng. Aspects, 2003, p. 43-50, vol. 212, Elsevier Science B.V.
Bertrand, Marylene et al., Conformational Transition of Acidic Peptides Exposed to Minerals in Suspension, Chem. Eur. J., 2000, p. 3452-3455, vol. 6, No. 18, Wiley-VCH.
International Search Report, International Application No. PCT/US2007/008526, International Filing Date Apr. 5, 2007.
U.S. Appl. No. 10/453,415, filed Jun. 3, 2003, Anand Jagota et. al.
Adey et. al., Characterization of Phage That Bind Plastic From Phage-Displayed Random Peptide Libraries, Gene, 1995, vol. 156:27-31.
Whaley et. al., Selection of Peptides With Semiconductor Binding Specificity for Directed Nanocrystal Assembly, Nature, 2000, vol. 405:665-668.
Dashman et. al., Adsorption and Binding of Peptides on Homoionic Montmorillonite and Kaolinite, Soil. Biol. Biochem., 1984, vol. 16:51-55.
Fusi et. al., Adsorption and Binding of Protein on Clean (Homoionic) and Dirty (Coated With Fe Oxhydroxides) Montmorillonite, Illite and Kaolinite, Soil Biol. Biochem., 1989, vol. 21:911-920.

* cited by examiner

*Primary Examiner*—Andrew D Kosar
*Assistant Examiner*—Satyanarayana R Gudibande

(57) ABSTRACT

Combinatorially generated peptides are provided that have binding affinity for clay. The peptides may be used to deliver benefit agents to various clay surfaces.

55 Claims, 6 Drawing Sheets

SEQUENCE LISTING

<160> NUMBER OF SEQ ID NOS: 218

<210> SEQ ID NO 1
<211> LENGTH: 12
<212> TYPE: PRT
<213> ORGANISM: Artificial sequence
<220> FEATURE:
<223> OTHER INFORMATION: Polymethylmethacrylate binding peptides

<400> SEQUENCE: 1

Ile Pro Trp Trp Asn Ile Arg Ala Pro Leu Asn Ala
1 5 10

<210> SEQ ID NO 2
<211> LENGTH: 12
<212> TYPE: PRT
<213> ORGANISM: Artificial Sequence
<220> FEATURE:
<223> OTHER INFORMATION: Polymethylmethacrylate-binding peptide

<400> SEQUENCE: 2

Thr Ala Val Met Asn Val Val Asn Asn Gln Leu Ser
1 5 10

<210> SEQ ID NO 3
<211> LENGTH: 12
<212> TYPE: PRT
<213> ORGANISM: Artificial Sequence
<220> FEATURE:
<223> OTHER INFORMATION: Polymethylmethacrylate-binding peptide

<400> SEQUENCE: 3

Val Pro Trp Trp Ala Pro Ser Lys Leu Ser Met Gln
1 5 10

<210> SEQ ID NO 4
<211> LENGTH: 12
<212> TYPE: PRT
<213> ORGANISM: Artificial Sequence
<220> FEATURE:
<223> OTHER INFORMATION: Polymethylmethacrylate-binding peptide

<400> SEQUENCE: 4

Met Val Met Ala Pro His Thr Pro Arg Ala Arg Ser
1 5 10

<210> SEQ ID NO 5
<211> LENGTH: 12
<212> TYPE: PRT
<213> ORGANISM: Artificial Sequence
<220> FEATURE:
<223> OTHER INFORMATION: Polymethylmethacrylate-binding peptide

<400> SEQUENCE: 5

Thr Tyr Pro Asn Trp Ala His Leu Leu Ser His Tyr
1 5 10

<210> SEQ ID NO 6
<211> LENGTH: 7
<212> TYPE: PRT
<213> ORGANISM: Artificial Sequence
<220> FEATURE:
<223> OTHER INFORMATION: Polymethylmethacrylate-binding peptide

<400> SEQUENCE: 6

-continued

```
Thr Pro Trp Trp Arg Ile Thr
1               5


<210> SEQ ID NO 7
<211> LENGTH: 7
<212> TYPE: PRT
<213> ORGANISM: Artificial Sequence
<220> FEATURE:
<223> OTHER INFORMATION: Polymethylmethacrylate-binding peptide

<400> SEQUENCE: 7

Asp Leu Thr Leu Pro Phe His
1               5


<210> SEQ ID NO 8
<211> LENGTH: 7
<212> TYPE: PRT
<213> ORGANISM: Artificial Sequence
<220> FEATURE:
<223> OTHER INFORMATION: Polymethylmethacrylate-binding peptide

<400> SEQUENCE: 8

Gly Thr Ser Ile Pro Ala Met
1               5


<210> SEQ ID NO 9
<211> LENGTH: 7
<212> TYPE: PRT
<213> ORGANISM: Artificial Sequence
<220> FEATURE:
<223> OTHER INFORMATION: Polymethylmethacrylate-binding peptide

<400> SEQUENCE: 9

His His Lys His Val Val Ala
1               5


<210> SEQ ID NO 10
<211> LENGTH: 7
<212> TYPE: PRT
<213> ORGANISM: Artificial Sequence
<220> FEATURE:
<223> OTHER INFORMATION: Polymethylmethacrylate-binding peptide

<400> SEQUENCE: 10

His His His Lys His Phe Met
1               5


<210> SEQ ID NO 11
<211> LENGTH: 7
<212> TYPE: PRT
<213> ORGANISM: Artificial Sequence
<220> FEATURE:
<223> OTHER INFORMATION: Polymethylmethacrylate-binding peptide

<400> SEQUENCE: 11

His His His Arg His Gln Gly
1               5


<210> SEQ ID NO 12
<211> LENGTH: 7
<212> TYPE: PRT
<213> ORGANISM: Artificial Sequence
<220> FEATURE:
<223> OTHER INFORMATION: Polymethylmethacrylate-binding peptide

<400> SEQUENCE: 12

His His Trp His Ala Pro Arg
```

-continued 1 5

<210> SEQ ID NO 13
<211> LENGTH: 17
<212> TYPE: PRT
<213> ORGANISM: Artificial sequence
<220> FEATURE:
<223> OTHER INFORMATION: antimicrobial peptide sequence

<400> SEQUENCE: 13

Pro Lys Gly Leu Lys Lys Leu Leu Lys Gly Leu Lys Lys Leu Leu Lys
1 5 10 15

Leu

<210> SEQ ID NO 14
<211> LENGTH: 16
<212> TYPE: PRT
<213> ORGANISM: Artificial Sequence
<220> FEATURE:
<223> OTHER INFORMATION: Antimicrobial peptide sequence

<400> SEQUENCE: 14

Lys Gly Leu Lys Lys Leu Leu Lys Gly Leu Lys Lys Leu Leu Lys Leu
1 5 10 15

<210> SEQ ID NO 15
<211> LENGTH: 16
<212> TYPE: PRT
<213> ORGANISM: Artificial Sequence
<220> FEATURE:
<223> OTHER INFORMATION: Antimicrobial peptide sequence

<400> SEQUENCE: 15

Lys Gly Leu Lys Lys Leu Leu Lys Leu Leu Lys Lys Leu Leu Lys Leu
1 5 10 15

<210> SEQ ID NO 16
<211> LENGTH: 14
<212> TYPE: PRT
<213> ORGANISM: Artificial Sequence
<220> FEATURE:
<223> OTHER INFORMATION: Antimicrobial peptide sequence

<400> SEQUENCE: 16

Leu Lys Lys Leu Leu Lys Leu Leu Lys Lys Leu Leu Lys Leu
1 5 10

<210> SEQ ID NO 17
<211> LENGTH: 12
<212> TYPE: PRT
<213> ORGANISM: Artificial Sequence
<220> FEATURE:
<223> OTHER INFORMATION: Antimicrobial peptide sequence

<400> SEQUENCE: 17

Leu Lys Lys Leu Leu Lys Leu Leu Lys Lys Leu Leu
1 5 10

<210> SEQ ID NO 18
<211> LENGTH: 17
<212> TYPE: PRT
<213> ORGANISM: Artificial Sequence
<220> FEATURE:
<223> OTHER INFORMATION: Antimicrobial peptide sequences

<400> SEQUENCE: 18

-continued

```
Val Ala Lys Lys Leu Ala Lys Leu Ala Lys Lys Leu Ala Lys Leu Ala
1               5                   10                  15

Leu


<210> SEQ ID NO 19
<211> LENGTH: 13
<212> TYPE: PRT
<213> ORGANISM: Artificial Sequence
<220> FEATURE:
<223> OTHER INFORMATION: Antimicrobial peptide sequences

<400> SEQUENCE: 19

Phe Ala Lys Leu Leu Ala Lys Ala Leu Lys Lys Leu Leu
1               5                   10


<210> SEQ ID NO 20
<211> LENGTH: 16
<212> TYPE: PRT
<213> ORGANISM: Artificial Sequence
<220> FEATURE:
<223> OTHER INFORMATION: Antimicrobial peptide sequence

<400> SEQUENCE: 20

Lys Gly Leu Lys Lys Gly Leu Lys Leu Leu Lys Lys Leu Leu Lys Leu
1               5                   10                  15


<210> SEQ ID NO 21
<211> LENGTH: 16
<212> TYPE: PRT
<213> ORGANISM: Artificial Sequence
<220> FEATURE:
<223> OTHER INFORMATION: Antimicrobial peptide sequence

<400> SEQUENCE: 21

Lys Gly Leu Lys Lys Leu Leu Lys Leu Gly Lys Lys Leu Leu Lys Leu
1               5                   10                  15


<210> SEQ ID NO 22
<211> LENGTH: 16
<212> TYPE: PRT
<213> ORGANISM: Artificial Sequence
<220> FEATURE:
<223> OTHER INFORMATION: Antimicrobial peptide sequence

<400> SEQUENCE: 22

Lys Gly Leu Lys Lys Leu Gly Lys Leu Leu Lys Lys Leu Leu Lys Leu
1               5                   10                  15


<210> SEQ ID NO 23
<211> LENGTH: 16
<212> TYPE: PRT
<213> ORGANISM: Artificial Sequence
<220> FEATURE:
<223> OTHER INFORMATION: Antimicrobial peptide sequence

<400> SEQUENCE: 23

Lys Gly Leu Lys Lys Leu Leu Lys Leu Leu Lys Lys Gly Leu Lys Leu
1               5                   10                  15


<210> SEQ ID NO 24
<211> LENGTH: 16
<212> TYPE: PRT
<213> ORGANISM: Artificial Sequence
<220> FEATURE:
<223> OTHER INFORMATION: Antimicrobial peptide sequence

<400> SEQUENCE: 24
```

Lys Gly Leu Lys Lys Leu Leu Lys Leu Leu Lys Lys Leu Gly Lys Leu
1 5 10 15

<210> SEQ ID NO 25
<211> LENGTH: 19
<212> TYPE: PRT
<213> ORGANISM: Artificial Sequence
<220> FEATURE:
<223> OTHER INFORMATION: Antimicrobial peptide sequences

<400> SEQUENCE: 25

Phe Ala Leu Ala Leu Lys Ala Leu Lys Lys Leu Lys Lys Ala Leu Lys
1 5 10 15

Lys Ala Leu

<210> SEQ ID NO 26
<211> LENGTH: 17
<212> TYPE: PRT
<213> ORGANISM: Artificial Sequence
<220> FEATURE:
<223> OTHER INFORMATION: Antimicrobial peptide sequence

<400> SEQUENCE: 26

Phe Ala Lys Lys Leu Ala Lys Leu Ala Lys Lys Leu Ala Lys Leu Ala
1 5 10 15

Leu

<210> SEQ ID NO 27
<211> LENGTH: 13
<212> TYPE: PRT
<213> ORGANISM: Artificial Sequence
<220> FEATURE:
<223> OTHER INFORMATION: Antimicrobial peptide sequences

<400> SEQUENCE: 27

Phe Ala Lys Leu Leu Ala Lys Leu Ala Lys Lys Leu Leu
1 5 10

<210> SEQ ID NO 28
<211> LENGTH: 15
<212> TYPE: PRT
<213> ORGANISM: Artificial Sequence
<220> FEATURE:
<223> OTHER INFORMATION: Antimicrobial peptide sequences

<400> SEQUENCE: 28

Phe Ala Lys Lys Leu Ala Lys Leu Ala Leu Lys Leu Ala Lys Leu
1 5 10 15

<210> SEQ ID NO 29
<211> LENGTH: 10
<212> TYPE: PRT
<213> ORGANISM: Artificial Sequence
<220> FEATURE:
<223> OTHER INFORMATION: Antimicrobial peptide sequences

<400> SEQUENCE: 29

Phe Ala Lys Lys Leu Ala Lys Lys Leu Leu
1 5 10

<210> SEQ ID NO 30
<211> LENGTH: 13
<212> TYPE: PRT
<213> ORGANISM: Artificial Sequence
<220> FEATURE:

-continued

<223> OTHER INFORMATION: Antimicrobial peptide sequence

<400> SEQUENCE: 30

Phe Ala Lys Leu Leu Ala Lys Leu Ala Lys Lys Val Leu
1 5 10

<210> SEQ ID NO 31
<211> LENGTH: 13
<212> TYPE: PRT
<213> ORGANISM: Artificial Sequence
<220> FEATURE:
<223> OTHER INFORMATION: Antimicrobial peptide sequences

<400> SEQUENCE: 31

Lys Tyr Lys Lys Ala Leu Lys Lys Leu Ala Lys Leu Leu
1 5 10

<210> SEQ ID NO 32
<211> LENGTH: 12
<212> TYPE: PRT
<213> ORGANISM: Artificial Sequence
<220> FEATURE:
<223> OTHER INFORMATION: Antimicrobial peptide sequences

<400> SEQUENCE: 32

Phe Ala Leu Leu Lys Ala Leu Leu Lys Lys Ala Leu
1 5 10

<210> SEQ ID NO 33
<211> LENGTH: 14
<212> TYPE: PRT
<213> ORGANISM: Artificial Sequence
<220> FEATURE:
<223> OTHER INFORMATION: Antimicrobial peptide sequence

<400> SEQUENCE: 33

Lys Arg Leu Phe Lys Lys Leu Lys Phe Ser Leu Arg Lys Tyr
1 5 10

<210> SEQ ID NO 34
<211> LENGTH: 14
<212> TYPE: PRT
<213> ORGANISM: Artificial Sequence
<220> FEATURE:
<223> OTHER INFORMATION: Antimicrobial peptide sequence

<400> SEQUENCE: 34

Lys Arg Leu Phe Lys Lys Leu Leu Phe Ser Leu Arg Lys Tyr
1 5 10

<210> SEQ ID NO 35
<211> LENGTH: 14
<212> TYPE: PRT
<213> ORGANISM: Artificial Sequence
<220> FEATURE:
<223> OTHER INFORMATION: Antimicrobial peptide sequence

<400> SEQUENCE: 35

Leu Leu Leu Phe Leu Leu Lys Lys Arg Lys Lys Arg Lys Tyr
1 5 10

<210> SEQ ID NO 36
<211> LENGTH: 36
<212> TYPE: PRT
<213> ORGANISM: Hyalophora cecropia

<400> SEQUENCE: 36

-continued

Lys Trp Lys Leu Phe Lys Lys Ile Glu Lys Val Gly Gln Asn Ile Arg
1               5                   10                  15

Asp Gly Ile Ile Lys Ala Gly Pro Ala Val Ala Trp Gly Gln Ala Thr
            20                  25                  30

Gln Ile Ala Lys
        35

<210> SEQ ID NO 37
<211> LENGTH: 23
<212> TYPE: PRT
<213> ORGANISM: Xenopus sp.

<400> SEQUENCE: 37

Gly Ile Gly Lys Phe Leu His Ser Ala Lys Lys Phe Gly Lys Ala Phe
1               5                   10                  15

Val Gly Glu Ile Met Asn Ser
            20

<210> SEQ ID NO 38
<211> LENGTH: 22
<212> TYPE: PRT
<213> ORGANISM: Xenopus sp.

<400> SEQUENCE: 38

Gly Ile Gly Lys Phe Leu Lys Lys Ala Lys Lys Phe Gly Lys Ala Phe
1               5                   10                  15

Val Lys Ile Leu Lys Lys
            20

<210> SEQ ID NO 39
<211> LENGTH: 12
<212> TYPE: PRT
<213> ORGANISM: Bos taurus

<400> SEQUENCE: 39

Arg Leu Cys Arg Ile Val Val Ile Arg Val Cys Arg
1               5                   10

<210> SEQ ID NO 40
<211> LENGTH: 13
<212> TYPE: PRT
<213> ORGANISM: Bos sp.

<400> SEQUENCE: 40

Ile Leu Pro Trp Lys Trp Pro Trp Trp Pro Trp Arg Arg
1               5                   10

<210> SEQ ID NO 41
<211> LENGTH: 24
<212> TYPE: PRT
<213> ORGANISM: Homo sapiens

<400> SEQUENCE: 41

Asp Ser His Ala Lys Arg His His Gly Tyr Lys Arg Lys Phe His Glu
1               5                   10                  15

Lys His His Ser His Arg Gly Tyr
            20

<210> SEQ ID NO 42
<211> LENGTH: 7
<212> TYPE: PRT
<213> ORGANISM: Artificial Sequence -continued
<220> FEATURE:
<223> OTHER INFORMATION: Pigment binding peptide sequence

<400> SEQUENCE: 42

Met Pro Pro Pro Leu Met Gln
1 5

<210> SEQ ID NO 43
<211> LENGTH: 7
<212> TYPE: PRT
<213> ORGANISM: Artificial Sequence
<220> FEATURE:
<223> OTHER INFORMATION: Pigment binding peptide sequences

<400> SEQUENCE: 43

Phe His Glu Asn Trp Pro Ser
1 5

<210> SEQ ID NO 44
<211> LENGTH: 12
<212> TYPE: PRT
<213> ORGANISM: Artificial Sequence
<220> FEATURE:
<223> OTHER INFORMATION: Pigment binding peptide sequence

<400> SEQUENCE: 44

Arg Thr Ala Pro Thr Thr Pro Leu Leu Leu Ser Leu
1 5 10

<210> SEQ ID NO 45
<211> LENGTH: 12
<212> TYPE: PRT
<213> ORGANISM: Artificial Sequence
<220> FEATURE:
<223> OTHER INFORMATION: Pigment binding peptide sequence

<400> SEQUENCE: 45

Trp His Leu Ser Trp Ser Pro Val Pro Leu Pro Thr
1 5 10

<210> SEQ ID NO 46
<211> LENGTH: 7
<212> TYPE: PRT
<213> ORGANISM: Artificial Sequence
<220> FEATURE:
<223> OTHER INFORMATION: Pigment binding peptide sequence

<400> SEQUENCE: 46

Pro His Ala Arg Leu Val Gly
1 5

<210> SEQ ID NO 47
<211> LENGTH: 7
<212> TYPE: PRT
<213> ORGANISM: Artificial Sequence
<220> FEATURE:
<223> OTHER INFORMATION: Pigment binding peptide sequence

<400> SEQUENCE: 47

Asn Ile Pro Tyr His His Pro
1 5

<210> SEQ ID NO 48
<211> LENGTH: 7
<212> TYPE: PRT
<213> ORGANISM: Artificial Sequence
<220> FEATURE:

-continued

<223> OTHER INFORMATION: Pigment binding peptide sequences

<400> SEQUENCE: 48

Thr Thr Met Pro Ala Ile Pro
1 5

<210> SEQ ID NO 49
<211> LENGTH: 7
<212> TYPE: PRT
<213> ORGANISM: Artificial Sequence
<220> FEATURE:
<223> OTHER INFORMATION: Pigment binding peptide sequence

<400> SEQUENCE: 49

His Asn Leu Pro Pro Arg Ser
1 5

<210> SEQ ID NO 50
<211> LENGTH: 12
<212> TYPE: PRT
<213> ORGANISM: Artificial Sequence
<220> FEATURE:
<223> OTHER INFORMATION: Pigment binding peptide sequences

<400> SEQUENCE: 50

Ala His Lys Thr Gln Met Gly Val Arg Gln Pro Ala
1 5 10

<210> SEQ ID NO 51
<211> LENGTH: 12
<212> TYPE: PRT
<213> ORGANISM: Artificial Sequence
<220> FEATURE:
<223> OTHER INFORMATION: Pigment binding peptide sequence

<400> SEQUENCE: 51

Ala Asp Asn Val Gln Met Gly Val Ser His Thr Pro
1 5 10

<210> SEQ ID NO 52
<211> LENGTH: 12
<212> TYPE: PRT
<213> ORGANISM: Artificial Sequence
<220> FEATURE:
<223> OTHER INFORMATION: Pigment binding peptide sequences

<400> SEQUENCE: 52

Ala His Asn Ala Gln Met Gly Val Ser His Pro Pro
1 5 10

<210> SEQ ID NO 53
<211> LENGTH: 12
<212> TYPE: PRT
<213> ORGANISM: Artificial Sequence
<220> FEATURE:
<223> OTHER INFORMATION: Pigment binding peptide sequence

<400> SEQUENCE: 53

Ala Asp Tyr Val Gly Met Gly Val Ser His Arg Pro
1 5 10

<210> SEQ ID NO 54
<211> LENGTH: 12
<212> TYPE: PRT
<213> ORGANISM: Artificial Sequence
<220> FEATURE:
<223> OTHER INFORMATION: Pigment binding peptide sequence -continued

<400> SEQUENCE: 54

Ser Val Ser Val Gly Met Lys Pro Ser Pro Arg Pro
1 5 10

<210> SEQ ID NO 55
<211> LENGTH: 7
<212> TYPE: PRT
<213> ORGANISM: Artificial Sequence
<220> FEATURE:
<223> OTHER INFORMATION: Pigment binding peptide sequence

<400> SEQUENCE: 55

Tyr Pro Asn Thr Ala Leu Val
1 5

<210> SEQ ID NO 56
<211> LENGTH: 7
<212> TYPE: PRT
<213> ORGANISM: Artificial Sequence
<220> FEATURE:
<223> OTHER INFORMATION: Pigment binding peptide sequences

<400> SEQUENCE: 56

Val Ala Thr Arg Ile Val Ser
1 5

<210> SEQ ID NO 57
<211> LENGTH: 12
<212> TYPE: PRT
<213> ORGANISM: Artificial Sequence
<220> FEATURE:
<223> OTHER INFORMATION: Pigment binding peptide sequences

<400> SEQUENCE: 57

His Ser Leu Lys Asn Ser Met Leu Thr Val Met Ala
1 5 10

<210> SEQ ID NO 58
<211> LENGTH: 7
<212> TYPE: PRT
<213> ORGANISM: Artificial Sequence
<220> FEATURE:
<223> OTHER INFORMATION: Pigment binding peptide sequences

<400> SEQUENCE: 58

Asn Tyr Pro Thr Gln Ala Pro
1 5

<210> SEQ ID NO 59
<211> LENGTH: 7
<212> TYPE: PRT
<213> ORGANISM: Artificial Sequence
<220> FEATURE:
<223> OTHER INFORMATION: Pigment binding peptide sequences

<400> SEQUENCE: 59

Lys Cys Cys Tyr Ser Val Gly
1 5

<210> SEQ ID NO 60
<211> LENGTH: 12
<212> TYPE: PRT
<213> ORGANISM: Artificial Sequence
<220> FEATURE:
<223> OTHER INFORMATION: Pigment binding peptide sequences

<400> SEQUENCE: 60

Arg His Asp Leu Asn Thr Trp Leu Pro Pro Val Lys
1 5 10

<210> SEQ ID NO 61
<211> LENGTH: 12
<212> TYPE: PRT
<213> ORGANISM: Artificial Sequence
<220> FEATURE:
<223> OTHER INFORMATION: Pigment binding peptide sequence

<400> SEQUENCE: 61

Glu Ile Ser Leu Pro Ala Lys Leu Pro Ser Ala Ser
1 5 10

<210> SEQ ID NO 62
<211> LENGTH: 12
<212> TYPE: PRT
<213> ORGANISM: Artificial Sequence
<220> FEATURE:
<223> OTHER INFORMATION: Pigment binding peptide sequence

<400> SEQUENCE: 62

Ser Asp Tyr Val Gly Met Arg Pro Ser Pro Arg His
1 5 10

<210> SEQ ID NO 63
<211> LENGTH: 12
<212> TYPE: PRT
<213> ORGANISM: Artificial Sequence
<220> FEATURE:
<223> OTHER INFORMATION: Pigment binding peptide sequences

<400> SEQUENCE: 63

Ser Asp Tyr Val Gly Met Arg Leu Ser Pro Ser Gln
1 5 10

<210> SEQ ID NO 64
<211> LENGTH: 12
<212> TYPE: PRT
<213> ORGANISM: Artificial Sequence
<220> FEATURE:
<223> OTHER INFORMATION: Pigment binding peptide sequences

<400> SEQUENCE: 64

Ser Val Ser Val Gly Ile Gln Pro Ser Pro Arg Pro
1 5 10

<210> SEQ ID NO 65
<211> LENGTH: 12
<212> TYPE: PRT
<213> ORGANISM: Artificial Sequence
<220> FEATURE:
<223> OTHER INFORMATION: Pigment binding peptide sequence

<400> SEQUENCE: 65

Tyr Val Ser Val Gly Ile Lys Pro Ser Pro Arg Pro
1 5 10

<210> SEQ ID NO 66
<211> LENGTH: 12
<212> TYPE: PRT
<213> ORGANISM: Artificial Sequence
<220> FEATURE:
<223> OTHER INFORMATION: Pigment binding peptide sequences

<400> SEQUENCE: 66

-continued

Tyr Val Cys Glu Gly Ile His Pro Cys Pro Arg Pro
1 5 10

<210> SEQ ID NO 67
<211> LENGTH: 7
<212> TYPE: PRT
<213> ORGANISM: Artificial Sequence
<220> FEATURE:
<223> OTHER INFORMATION: Print Medium-Binding Peptide

<400> SEQUENCE: 67

Ser Ile Leu Pro Tyr Pro Tyr
1 5

<210> SEQ ID NO 68
<211> LENGTH: 7
<212> TYPE: PRT
<213> ORGANISM: Artificial Sequence
<220> FEATURE:
<223> OTHER INFORMATION: Print Medium-Binding Peptide

<400> SEQUENCE: 68

Ser Thr Ala Ser Tyr Thr Arg
1 5

<210> SEQ ID NO 69
<211> LENGTH: 7
<212> TYPE: PRT
<213> ORGANISM: Artificial Sequence
<220> FEATURE:
<223> OTHER INFORMATION: Print Medium-Binding Peptide

<400> SEQUENCE: 69

Leu Pro Val Arg Pro Trp Thr
1 5

<210> SEQ ID NO 70
<211> LENGTH: 7
<212> TYPE: PRT
<213> ORGANISM: Artificial Sequence
<220> FEATURE:
<223> OTHER INFORMATION: Print Medium-Binding Peptide

<400> SEQUENCE: 70

Gly Asn Thr Pro Ser Arg Ala
1 5

<210> SEQ ID NO 71
<211> LENGTH: 7
<212> TYPE: PRT
<213> ORGANISM: Artificial Sequence
<220> FEATURE:
<223> OTHER INFORMATION: Print Medium-Binding Peptides

<400> SEQUENCE: 71

His Ala Ile Tyr Pro Arg His
1 5

<210> SEQ ID NO 72
<211> LENGTH: 7
<212> TYPE: PRT
<213> ORGANISM: Artificial Sequence
<220> FEATURE:
<223> OTHER INFORMATION: Print Medium-Binding Peptides

<400> SEQUENCE: 72

-continued

```
Tyr Gln Asp Ser Ala Lys Thr
1               5


<210> SEQ ID NO 73
<211> LENGTH: 7
<212> TYPE: PRT
<213> ORGANISM: Artificial Sequence
<220> FEATURE:
<223> OTHER INFORMATION: Cellulose Binding Peptide

<400> SEQUENCE: 73

Val Pro Arg Val Thr Ser Ile
1               5


<210> SEQ ID NO 74
<211> LENGTH: 7
<212> TYPE: PRT
<213> ORGANISM: Artificial Sequence
<220> FEATURE:
<223> OTHER INFORMATION: Cellulose-Binding Peptide

<400> SEQUENCE: 74

Met Ala Asn His Asn Leu Ser
1               5


<210> SEQ ID NO 75
<211> LENGTH: 7
<212> TYPE: PRT
<213> ORGANISM: Artificial Sequence
<220> FEATURE:
<223> OTHER INFORMATION: Cellulose-Binding Peptide

<400> SEQUENCE: 75

Phe His Glu Asn Trp Pro Ser
1               5


<210> SEQ ID NO 76
<211> LENGTH: 12
<212> TYPE: PRT
<213> ORGANISM: Artificial sequence
<220> FEATURE:
<223> OTHER INFORMATION: Cellulose-Binding Peptide

<400> SEQUENCE: 76

Thr His Lys Thr Ser Thr Gln Arg Leu Leu Ala Ala
1               5                   10


<210> SEQ ID NO 77
<211> LENGTH: 12
<212> TYPE: PRT
<213> ORGANISM: Artificial sequence
<220> FEATURE:
<223> OTHER INFORMATION: Cellulose-Binding Peptide

<400> SEQUENCE: 77

Lys Cys Cys Tyr Val Asn Val Gly Ser Val Phe Ser
1               5                   10


<210> SEQ ID NO 78
<211> LENGTH: 12
<212> TYPE: PRT
<213> ORGANISM: Artificial sequence
<220> FEATURE:
<223> OTHER INFORMATION: Cellulose-Binding Peptide

<400> SEQUENCE: 78

Ala His Met Gln Phe Arg Thr Ser Leu Thr Pro His
```

-continued 1 5 10

<210> SEQ ID NO 79
<211> LENGTH: 12
<212> TYPE: PRT
<213> ORGANISM: Artificial sequence
<220> FEATURE:
<223> OTHER INFORMATION: Poly(ethylene terephthalate)-Binding Peptide

<400> SEQUENCE: 79

Gly Thr Ser Asp His Met Ile Met Pro Phe Phe Asn
1 5 10

<210> SEQ ID NO 80
<211> LENGTH: 7
<212> TYPE: PRT
<213> ORGANISM: Artificial sequence
<220> FEATURE:
<223> OTHER INFORMATION: Skin Binding Peptide Domain

<400> SEQUENCE: 80

Phe Thr Gln Ser Leu Pro Arg
1 5

<210> SEQ ID NO 81
<211> LENGTH: 12
<212> TYPE: PRT
<213> ORGANISM: Artificial Sequence
<220> FEATURE:
<223> OTHER INFORMATION: Skin Binding Peptide Domain

<400> SEQUENCE: 81

Thr Pro Phe His Ser Pro Glu Asn Ala Pro Gly Ser
1 5 10

<210> SEQ ID NO 82
<211> LENGTH: 12
<212> TYPE: PRT
<213> ORGANISM: Artificial Sequence
<220> FEATURE:
<223> OTHER INFORMATION: Skin Binding Peptide Domain

<400> SEQUENCE: 82

Lys Gln Ala Thr Phe Pro Pro Asn Pro Thr Ala Tyr
1 5 10

<210> SEQ ID NO 83
<211> LENGTH: 12
<212> TYPE: PRT
<213> ORGANISM: Artificial Sequence
<220> FEATURE:
<223> OTHER INFORMATION: Skin Binding Peptide Domain

<400> SEQUENCE: 83

His Gly His Met Val Ser Thr Ser Gln Leu Ser Ile
1 5 10

<210> SEQ ID NO 84
<211> LENGTH: 7
<212> TYPE: PRT
<213> ORGANISM: Artificial Sequence
<220> FEATURE:
<223> OTHER INFORMATION: Skin Binding Peptide Domain

<400> SEQUENCE: 84

Leu Ser Pro Ser Arg Met Lys
1 5

-continued

<210> SEQ ID NO 85
<211> LENGTH: 7
<212> TYPE: PRT
<213> ORGANISM: Artificial Sequence
<220> FEATURE:
<223> OTHER INFORMATION: Skin Binding Peptide Domain

<400> SEQUENCE: 85

Leu Pro Ile Pro Arg Met Lys
1 5

<210> SEQ ID NO 86
<211> LENGTH: 7
<212> TYPE: PRT
<213> ORGANISM: Artificial Sequence
<220> FEATURE:
<223> OTHER INFORMATION: Skin Binding Peptide Domain

<400> SEQUENCE: 86

His Gln Arg Pro Tyr Leu Thr
1 5

<210> SEQ ID NO 87
<211> LENGTH: 7
<212> TYPE: PRT
<213> ORGANISM: Artificial Sequence
<220> FEATURE:
<223> OTHER INFORMATION: Skin Binding Peptide Domain

<400> SEQUENCE: 87

Phe Pro Pro Leu Leu Arg Leu
1 5

<210> SEQ ID NO 88
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 88

Ala Leu Pro Arg Ile Ala Asn Thr Trp Ser Pro Ser
1 5 10

<210> SEQ ID NO 89
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 89

Tyr Pro Ser Phe Ser Pro Thr Tyr Arg Pro Ala Phe
1 5 10

<210> SEQ ID NO 90
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 90

Tyr Pro Ser Phe Ser Pro Thr Tyr Arg Pro Ala Phe
1 5 10

-continued

<210> SEQ ID NO 91
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 91

Ala Leu Pro Arg Ile Ala Asn Thr Trp Ser Pro Ser
1 5 10

<210> SEQ ID NO 92
<211> LENGTH: 8
<212> TYPE: PRT
<213> ORGANISM: Artificial Sequence
<220> FEATURE:
<223> OTHER INFORMATION: Hair Binding Peptide Domain

<400> SEQUENCE: 92

Leu Glu Ser Thr Pro Lys Met Lys
1 5

<210> SEQ ID NO 93
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 93

Ser Val Ser Val Gly Met Lys Pro Ser Pro Arg Pro
1 5 10

<210> SEQ ID NO 94
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 94

Leu Asp Val Glu Ser Tyr Lys Gly Thr Ser Met Pro
1 5 10

<210> SEQ ID NO 95
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 95

Arg Val Pro Asn Lys Thr Val Thr Val Asp Gly Ala
1 5 10

<210> SEQ ID NO 96
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 96

Asp Arg His Lys Ser Lys Tyr Ser Ser Thr Lys Ser
1 5 10

-continued

<210> SEQ ID NO 97
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 97

Lys Asn Phe Pro Gln Gln Lys Glu Phe Pro Leu Ser
1 5 10

<210> SEQ ID NO 98
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 98

Gln Arg Asn Ser Pro Pro Ala Met Ser Arg Arg Asp
1 5 10

<210> SEQ ID NO 99
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 99

Thr Arg Lys Pro Asn Met Pro His Gly Gln Tyr Leu
1 5 10

<210> SEQ ID NO 100
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 100

Lys Pro Pro His Leu Ala Lys Leu Pro Phe Thr Thr
1 5 10

<210> SEQ ID NO 101
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 101

Asn Lys Arg Pro Pro Thr Ser His Arg Ile His Ala
1 5 10

<210> SEQ ID NO 102
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 102

Asn Leu Pro Arg Tyr Gln Pro Pro Cys Lys Pro Leu
1 5 10

<210> SEQ ID NO 103

-continued

<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 103

Arg Pro Pro Trp Lys Lys Pro Ile Pro Pro Ser Glu
1 5 10

<210> SEQ ID NO 104
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 104

Arg Gln Arg Pro Lys Asp His Phe Phe Ser Arg Pro
1 5 10

<210> SEQ ID NO 105
<211> LENGTH: 12
<212> TYPE: PRT
<213> ORGANISM: Artificial Sequence
<220> FEATURE:
<223> OTHER INFORMATION: Hair Binding Peptide Domain
<220> FEATURE:
<221> NAME/KEY: MISC_FEATURE
<222> LOCATION: (6)..(6)
<223> OTHER INFORMATION: X= T or P
<220> FEATURE:
<221> NAME/KEY: MISC_FEATURE
<222> LOCATION: (12)..(12)
<223> OTHER INFORMATION: X= E or A

<400> SEQUENCE: 105

Ser Val Pro Asn Lys Xaa Val Thr Val Asp Gly Xaa
1 5 10

<210> SEQ ID NO 106
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 106

Thr Thr Lys Trp Arg His Arg Ala Pro Val Ser Pro
1 5 10

<210> SEQ ID NO 107
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 107

Trp Leu Gly Lys Asn Arg Ile Lys Pro Arg Ala Ser
1 5 10

<210> SEQ ID NO 108
<211> LENGTH: 12
<212> TYPE: PRT
<213> ORGANISM: Artificial Sequence
<220> FEATURE:
<223> OTHER INFORMATION: Hair Binding Peptide Domain -continued

<400> SEQUENCE: 108

Ser Asn Phe Lys Thr Pro Leu Pro Leu Thr Gln Ser
1 5 10

<210> SEQ ID NO 109
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 109

Lys Glu Leu Gln Thr Arg Asn Val Val Gln Arg Glu
1 5 10

<210> SEQ ID NO 110
<211> LENGTH: 12
<212> TYPE: PRT
<213> ORGANISM: Artificial Sequence
<220> FEATURE:
<223> OTHER INFORMATION: Hair-binding peptide

<400> SEQUENCE: 110

Gly Met Pro Ala Met His Trp Ile His Pro Phe Ala
1 5 10

<210> SEQ ID NO 111
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 111

Thr Pro Thr Ala Asn Gln Phe Thr Gln Ser Val Pro
1 5 10

<210> SEQ ID NO 112
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 112

Ala Ala Gly Leu Ser Gln Lys His Glu Arg Asn Arg
1 5 10

<210> SEQ ID NO 113
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 113

Glu Thr Val His Gln Thr Pro Leu Ser Asp Arg Pro
1 5 10

<210> SEQ ID NO 114
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 114

-continued

```
Leu Pro Ala Leu His Ile Gln Arg His Pro Arg Met
1               5                   10


<210> SEQ ID NO 115
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 115

Gln Pro Ser His Ser Gln Ser His Asn Leu Arg Ser
1               5                   10


<210> SEQ ID NO 116
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 116

Arg Gly Ser Gln Lys Ser Lys Pro Pro Arg Pro Pro
1               5                   10


<210> SEQ ID NO 117
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 117

Thr His Thr Gln Lys Thr Pro Leu Leu Tyr Tyr His
1               5                   10


<210> SEQ ID NO 118
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 118

Thr Lys Gly Ser Ser Gln Ala Ile Leu Lys Ser Thr
1               5                   10


<210> SEQ ID NO 119
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 119

Asp Leu His Thr Val Tyr His
1               5


<210> SEQ ID NO 120
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 120
```

-continued

His Ile Lys Pro Pro Thr Arg
1 5

<210> SEQ ID NO 121
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 121

His Pro Val Trp Pro Ala Ile
1 5

<210> SEQ ID NO 122
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 122

Met Pro Leu Tyr Tyr Leu Gln
1 5

<210> SEQ ID NO 123
<211> LENGTH: 26
<212> TYPE: PRT
<213> ORGANISM: Artificial Sequence
<220> FEATURE:
<223> OTHER INFORMATION: Hair Binding Peptide Domain

<400> SEQUENCE: 123

His Leu Thr Val Pro Trp Arg Gly Gly Gly Ser Ala Val Pro Phe Tyr
1 5 10 15

Ser His Ser Gln Ile Thr Leu Pro Asn His
20 25

<210> SEQ ID NO 124
<211> LENGTH: 41
<212> TYPE: PRT
<213> ORGANISM: Artificial Sequence
<220> FEATURE:
<223> OTHER INFORMATION: Hair Binding Peptide Domain

<400> SEQUENCE: 124

Gly Pro His Asp Thr Ser Ser Gly Gly Val Arg Pro Asn Leu His His
1 5 10 15

Thr Ser Lys Lys Glu Lys Arg Glu Asn Arg Lys Val Pro Phe Tyr Ser
20 25 30

His Ser Val Thr Ser Arg Gly Asn Val
35 40

<210> SEQ ID NO 125
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 125

Lys His Pro Thr Tyr Arg Gln
1 5

<210> SEQ ID NO 126

-continued

<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 126

His Pro Met Ser Ala Pro Arg
1 5

<210> SEQ ID NO 127
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 127

Met Pro Lys Tyr Tyr Leu Gln
1 5

<210> SEQ ID NO 128
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 128

Met His Ala His Ser Ile Ala
1 5

<210> SEQ ID NO 129
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 129

Thr Ala Ala Thr Thr Ser Pro
1 5

<210> SEQ ID NO 130
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 130

Leu Gly Ile Pro Gln Asn Leu
1 5

<210> SEQ ID NO 131
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 131

Ala Lys Pro Ile Ser Gln His Leu Gln Arg Gly Ser
1 5 10

<210> SEQ ID NO 132
<211> LENGTH: 12

-continued

<212> TYPE: PRT
<213> ORGANISM: Artificial Sequence
<220> FEATURE:
<223> OTHER INFORMATION: Hair Binding Peptide Domain

<400> SEQUENCE: 132

Ala Pro Pro Thr Pro Ala Ala Ala Ser Ala Thr Thr
1 5 10

<210> SEQ ID NO 133
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 133

Asp Pro Thr Glu Gly Ala Arg Arg Thr Ile Met Thr
1 5 10

<210> SEQ ID NO 134
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 134

Glu Gln Ile Ser Gly Ser Leu Val Ala Ala Pro Trp
1 5 10

<210> SEQ ID NO 135
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 135

Leu Asp Thr Ser Phe Pro Pro Val Pro Phe His Ala
1 5 10

<210> SEQ ID NO 136
<211> LENGTH: 11
<212> TYPE: PRT
<213> ORGANISM: Artificial Sequence
<220> FEATURE:
<223> OTHER INFORMATION: Hair Binding Peptide Domain

<400> SEQUENCE: 136

Leu Pro Arg Ile Ala Asn Thr Trp Ser Pro Ser
1 5 10

<210> SEQ ID NO 137
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 137

Arg Thr Asn Ala Ala Asp His Pro Ala Ala Val Thr
1 5 10

<210> SEQ ID NO 138
<211> LENGTH: 12
<212> TYPE: PRT

-continued

<213> ORGANISM: Artificial Sequence
<220> FEATURE:
<223> OTHER INFORMATION: HairBinding Peptide Domain

<400> SEQUENCE: 138

Ser Leu Asn Trp Val Thr Ile Pro Gly Pro Lys Ile
1 5 10

<210> SEQ ID NO 139
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 139

Thr Asp Met Gln Ala Pro Thr Lys Ser Tyr Ser Asn
1 5 10

<210> SEQ ID NO 140
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 140

Thr Ile Met Thr Lys Ser Pro Ser Leu Ser Cys Gly
1 5 10

<210> SEQ ID NO 141
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 141

Thr Pro Ala Leu Asp Gly Leu Arg Gln Pro Leu Arg
1 5 10

<210> SEQ ID NO 142
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 142

Thr Tyr Pro Ala Ser Arg Leu Pro Leu Leu Ala Pro
1 5 10

<210> SEQ ID NO 143
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 143

Thr Tyr Pro Ala Ser Arg Leu Pro Leu Leu Ala Pro
1 5 10

<210> SEQ ID NO 144
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 144

Thr Asp Pro Thr Pro Phe Ser Ile Ser Pro Glu Arg
1 5 10

<210> SEQ ID NO 145
<211> LENGTH: 20
<212> TYPE: PRT
<213> ORGANISM: Artificial Sequence
<220> FEATURE:
<223> OTHER INFORMATION: Hair Binding Peptide Domain

<400> SEQUENCE: 145

Cys Ala Ala Gly Cys Cys Thr Cys Ala Gly Cys Gly Ala Cys Cys Gly
1 5 10 15

Ala Ala Thr Ala
20

<210> SEQ ID NO 146
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 146

Trp His Asp Lys Pro Gln Asn Ser Ser Lys Ser Thr
1 5 10

<210> SEQ ID NO 147
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 147

Asn Glu Val Pro Ala Arg Asn Ala Pro Trp Leu Val
1 5 10

<210> SEQ ID NO 148
<211> LENGTH: 13
<212> TYPE: PRT
<213> ORGANISM: Artificial Sequence
<220> FEATURE:
<223> OTHER INFORMATION: Hair Binding Peptide Domain

<400> SEQUENCE: 148

Asn Ser Pro Gly Tyr Gln Ala Asp Ser Val Ala Ile Gly
1 5 10

<210> SEQ ID NO 149
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 149

Thr Gln Asp Ser Ala Gln Lys Ser Pro Ser Pro Leu
1 5 10

<210> SEQ ID NO 150
<211> LENGTH: 12

-continued

<212> TYPE: PRT
<213> ORGANISM: Artificial Sequence
<220> FEATURE:
<223> OTHER INFORMATION: Hair Binding Peptide Domain

<400> SEQUENCE: 150

Thr Pro Pro Glu Leu Leu His Gly Asp Pro Arg Ser
1 5 10

<210> SEQ ID NO 151
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 151

Thr Pro Pro Thr Asn Val Leu Met Leu Ala Thr Lys
1 5 10

<210> SEQ ID NO 152
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 152

Asn Thr Ser Gln Leu Ser Thr
1 5

<210> SEQ ID NO 153
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 153

Asn Thr Pro Lys Glu Asn Trp
1 5

<210> SEQ ID NO 154
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 154

Asn Thr Pro Ala Ser Asn Arg
1 5

<210> SEQ ID NO 155
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 155

Pro Arg Gly Met Leu Ser Thr
1 5

<210> SEQ ID NO 156
<211> LENGTH: 7
<212> TYPE: PRT

-continued

<213> ORGANISM: Artificial Sequence
<220> FEATURE:
<223> OTHER INFORMATION: Hair Binding Peptide Domain

<400> SEQUENCE: 156

Pro Pro Thr Tyr Leu Ser Thr
1 5

<210> SEQ ID NO 157
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 157

Thr Ile Pro Thr His Arg Gln His Asp Tyr Arg Ser
1 5 10

<210> SEQ ID NO 158
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 158

Thr Pro Pro Thr His Arg Leu
1 5

<210> SEQ ID NO 159
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 159

Leu Pro Thr Met Ser Thr Pro
1 5

<210> SEQ ID NO 160
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 160

Leu Gly Thr Asn Ser Thr Pro
1 5

<210> SEQ ID NO 161
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 161

Thr Pro Leu Thr Gly Ser Thr Asn Leu Leu Ser Ser
1 5 10

<210> SEQ ID NO 162
<211> LENGTH: 7
<212> TYPE: PRT
<213> ORGANISM: Artificial Sequence -continued
<220> FEATURE:
<223> OTHER INFORMATION: Hair Binding Peptide Domain

<400> SEQUENCE: 162

Thr Pro Leu Thr Lys Glu Thr
1 5

<210> SEQ ID NO 163
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 163

Gln Gln Ser His Asn Pro Pro
1 5

<210> SEQ ID NO 164
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 164

Thr Gln Pro His Asn Pro Pro
1 5

<210> SEQ ID NO 165
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 165

Ser Thr Asn Leu Leu Arg Thr Ser Thr Val His Pro
1 5 10

<210> SEQ ID NO 166
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 166

His Thr Gln Pro Ser Tyr Ser Ser Thr Asn Leu Phe
1 5 10

<210> SEQ ID NO 167
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 167

Ser Leu Leu Ser Ser His Ala
1 5

<210> SEQ ID NO 168
<211> LENGTH: 12
<212> TYPE: PRT
<213> ORGANISM: Artificial Sequence
<220> FEATURE:

-continued

<223> OTHER INFORMATION: Hair Binding Peptide Domain

<400> SEQUENCE: 168

Gln Gln Ser Ser Ile Ser Leu Ser Ser His Ala Val
1 5 10

<210> SEQ ID NO 169
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 169

Asn Ala Ser Pro Ser Ser Leu
1 5

<210> SEQ ID NO 170
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 170

His Ser Pro Ser Ser Leu Arg
1 5

<210> SEQ ID NO 171
<211> LENGTH: 7
<212> TYPE: PRT
<213> ORGANISM: Artificial Sequence
<220> FEATURE:
<223> OTHER INFORMATION: Hair Binding Peptide Domain
<220> FEATURE:
<221> NAME/KEY: MISC_FEATURE
<222> LOCATION: (2)..(2)
<223> OTHER INFORMATION: X= H, R or N

<400> SEQUENCE: 171

Lys Xaa Ser His His Thr His
1 5

<210> SEQ ID NO 172
<211> LENGTH: 7
<212> TYPE: PRT
<213> ORGANISM: Artificial Sequence
<220> FEATURE:
<223> OTHER INFORMATION: Hair Binding Peptide Domain
<220> FEATURE:
<221> NAME/KEY: MISC_FEATURE
<222> LOCATION: (2)..(2)
<223> OTHER INFORMATION: X=H or Ror N
<220> FEATURE:
<221> NAME/KEY: MISC_FEATURE
<222> LOCATION: (2)..(2)
<223> OTHER INFORMATION: X= H, R, or N

<400> SEQUENCE: 172

Glu Xaa Ser His His Thr His
1 5

<210> SEQ ID NO 173
<211> LENGTH: 7
<212> TYPE: PRT
<213> ORGANISM: Artificial Sequence
<220> FEATURE:
<223> OTHER INFORMATION: Hair Binding Peptide Domain -continued

<400> SEQUENCE: 173

Leu Glu Ser Thr Ser Leu Leu
1 5

<210> SEQ ID NO 174
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 174

Thr Pro Leu Thr Lys Glu Thr
1 5

<210> SEQ ID NO 175
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 175

Lys Gln Ser His Asn Pro Pro
1 5

<210> SEQ ID NO 176
<211> LENGTH: 8
<212> TYPE: PRT
<213> ORGANISM: Artificial Sequence
<220> FEATURE:
<223> OTHER INFORMATION: Linker Peptide

<400> SEQUENCE: 176

Leu Glu Ser Gly Asp Glu Val Asp
1 5

<210> SEQ ID NO 177
<211> LENGTH: 37
<212> TYPE: PRT
<213> ORGANISM: Artificial Sequence
<220> FEATURE:
<223> OTHER INFORMATION: Linker peptide

<400> SEQUENCE: 177

Thr Ser Thr Ser Lys Ala Ser Thr Thr Thr Thr Ser Ser Lys Thr Thr
1 5 10 15

Thr Thr Ser Ser Lys Thr Thr Thr Thr Thr Ser Lys Thr Ser Thr Thr
20 25 30

Ser Ser Ser Ser Thr
35

<210> SEQ ID NO 178
<211> LENGTH: 22
<212> TYPE: PRT
<213> ORGANISM: Artificial Sequence
<220> FEATURE:
<223> OTHER INFORMATION: Linker peptide

<400> SEQUENCE: 178

Gly Gln Gly Gly Tyr Gly Gly Leu Gly Ser Gln Gly Ala Gly Arg Gly
1 5 10 15

Gly Leu Gly Gly Gln Gly
20

-continued

<210> SEQ ID NO 179
<211> LENGTH: 10
<212> TYPE: PRT
<213> ORGANISM: Artificial Sequence
<220> FEATURE:
<223> OTHER INFORMATION: Linker peptide

<400> SEQUENCE: 179

Gly Pro Gly Gly Tyr Gly Pro Gly Gln Gln
1               5                   10

<210> SEQ ID NO 180
<211> LENGTH: 7
<212> TYPE: PRT
<213> ORGANISM: Artificial Sequence
<220> FEATURE:
<223> OTHER INFORMATION: Nylon-Binding Peptide

<400> SEQUENCE: 180

Lys Thr Pro Pro Thr Arg Pro
1               5

<210> SEQ ID NO 181
<211> LENGTH: 7
<212> TYPE: PRT
<213> ORGANISM: Artificial Sequence
<220> FEATURE:
<223> OTHER INFORMATION: Nylon-Binding Peptide

<400> SEQUENCE: 181

Val Ile Asn Pro Asn Leu Asp
1               5

<210> SEQ ID NO 182
<211> LENGTH: 7
<212> TYPE: PRT
<213> ORGANISM: Artificial Sequence
<220> FEATURE:
<223> OTHER INFORMATION: Nylon-Binding Peptide

<400> SEQUENCE: 182

Lys Val Trp Ile Val Ser Thr
1               5

<210> SEQ ID NO 183
<211> LENGTH: 7
<212> TYPE: PRT
<213> ORGANISM: Artificial Sequence
<220> FEATURE:
<223> OTHER INFORMATION: Nylon-Binding  Peptide

<400> SEQUENCE: 183

Ala Glu Pro Val Ala Met Leu
1               5

<210> SEQ ID NO 184
<211> LENGTH: 7
<212> TYPE: PRT
<213> ORGANISM: Artificial Sequence
<220> FEATURE:
<223> OTHER INFORMATION: Nylon-Binding Peptide

<400> SEQUENCE: 184

Ala Glu Leu Val Ala Met Leu
1               5

-continued

<210> SEQ ID NO 185
<211> LENGTH: 7
<212> TYPE: PRT
<213> ORGANISM: Artificial Sequence
<220> FEATURE:
<223> OTHER INFORMATION: Nylon-Binding Peptide

<400> SEQUENCE: 185

His Ser Leu Arg Leu Asp Trp
1 5

<210> SEQ ID NO 186
<211> LENGTH: 12
<212> TYPE: PRT
<213> ORGANISM: Artificial Sequence
<220> FEATURE:
<223> OTHER INFORMATION: Poly(tetrafluoroethylene)-Binding Peptide

<400> SEQUENCE: 186

Glu Ser Ser Tyr Ser Trp Ser Pro Ala Arg Leu Ser
1 5 10

<210> SEQ ID NO 187
<211> LENGTH: 12
<212> TYPE: PRT
<213> ORGANISM: Artificial Sequence
<220> FEATURE:
<223> OTHER INFORMATION: Poly(tetrafluoroethylene)-Binding Peptide

<400> SEQUENCE: 187

Gly Pro Leu Lys Leu Leu His Ala Trp Trp Gln Pro
1 5 10

<210> SEQ ID NO 188
<211> LENGTH: 7
<212> TYPE: PRT
<213> ORGANISM: Artificial Sequence
<220> FEATURE:
<223> OTHER INFORMATION: Poly(tetrafluoroethylene)-Binding Peptide

<400> SEQUENCE: 188

Asn Ala Leu Thr Arg Pro Val
1 5

<210> SEQ ID NO 189
<211> LENGTH: 7
<212> TYPE: PRT
<213> ORGANISM: Artificial Sequence
<220> FEATURE:
<223> OTHER INFORMATION: Poly(tetrafluoroethylene)-Binding Peptide

<400> SEQUENCE: 189

Ser Ala Pro Ser Ser Lys Asn
1 5

<210> SEQ ID NO 190
<211> LENGTH: 12
<212> TYPE: PRT
<213> ORGANISM: Artificial Sequence
<220> FEATURE:
<223> OTHER INFORMATION: Poly(tetrafluoroethylene)-Binding Peptide

<400> SEQUENCE: 190

Ser Val Ser Val Gly Met Lys Pro Ser Pro Arg Pro
1 5 10

<210> SEQ ID NO 191

-continued

<211> LENGTH: 12
<212> TYPE: PRT
<213> ORGANISM: Artificial Sequence
<220> FEATURE:
<223> OTHER INFORMATION: Poly(tetrafluoroethylene)-Binding Peptide

<400> SEQUENCE: 191

Ser Tyr Tyr Ser Leu Pro Pro Ile Phe His Ile Pro
1 5 10

<210> SEQ ID NO 192
<211> LENGTH: 12
<212> TYPE: PRT
<213> ORGANISM: Artificial Sequence
<220> FEATURE:
<223> OTHER INFORMATION: Poly(tetrafluoroethylene)-Binding Peptide

<400> SEQUENCE: 192

Thr Phe Thr Pro Tyr Ser Ile Thr His Ala Leu Leu
1 5 10

<210> SEQ ID NO 193
<211> LENGTH: 12
<212> TYPE: PRT
<213> ORGANISM: Artificial Sequence
<220> FEATURE:
<223> OTHER INFORMATION: Poly(tetrafluoroethylene)-Binding Peptide

<400> SEQUENCE: 193

Thr Met Gly Phe Thr Ala Pro Arg Phe Pro His Tyr
1 5 10

<210> SEQ ID NO 194
<211> LENGTH: 12
<212> TYPE: PRT
<213> ORGANISM: Artificial Sequence
<220> FEATURE:
<223> OTHER INFORMATION: Poly(tetrafluoroethylene)-Binding Peptide

<400> SEQUENCE: 194

Thr Asn Pro Phe Pro Pro Pro Pro Ser Ser Pro Ala
1 5 10

<210> SEQ ID NO 195
<211> LENGTH: 15
<212> TYPE: PRT
<213> ORGANISM: Artificial Sequence
<220> FEATURE:
<223> OTHER INFORMATION: Hair-binding peptide

<400> SEQUENCE: 195

Ser Thr Leu His Lys Tyr Lys Ser Gln Asp Pro Thr Pro His His
1 5 10 15

<210> SEQ ID NO 196
<211> LENGTH: 15
<212> TYPE: PRT
<213> ORGANISM: Artificial Sequence
<220> FEATURE:
<223> OTHER INFORMATION: Hair-binding peptide

<400> SEQUENCE: 196

His Asp His Lys Asn Gln Lys Glu Thr His Gln Arg His Ala Ala
1 5 10 15

<210> SEQ ID NO 197
<211> LENGTH: 20

-continued

<212> TYPE: PRT
<213> ORGANISM: Artificial Sequence
<220> FEATURE:
<223> OTHER INFORMATION: Hair-binding peptide

<400> SEQUENCE: 197

His Asn His Met Gln Glu Arg Tyr Thr Asp Pro Gln His Ser Pro Ser
1 5 10 15

Val Asn Gly Leu
20

<210> SEQ ID NO 198
<211> LENGTH: 20
<212> TYPE: PRT
<213> ORGANISM: Artificial Sequence
<220> FEATURE:
<223> OTHER INFORMATION: Hair-binding peptide

<400> SEQUENCE: 198

Thr Ala Glu Ile Asp Ser Ser Lys Asn Pro Asn Pro His Pro Gln Arg
1 5 10 15

Ser Trp Thr Asn
20

<210> SEQ ID NO 199
<211> LENGTH: 17
<212> TYPE: PRT
<213> ORGANISM: artificial sequence
<220> FEATURE:
<223> OTHER INFORMATION: N terminal constant region

<400> SEQUENCE: 199

Met His His His His His His Ser Gly Ser Ser Ser Gly Ser Gly Ser
1 5 10 15

Gly

<210> SEQ ID NO 200
<211> LENGTH: 16
<212> TYPE: PRT
<213> ORGANISM: artificial sequence
<220> FEATURE:
<223> OTHER INFORMATION: C terminal constant region

<400> SEQUENCE: 200

Thr Ser Gly Gly Ser Ser Gly Ser Ser Leu Gly Val Ala Ser Ala Ile
1 5 10 15

<210> SEQ ID NO 201
<211> LENGTH: 28
<212> TYPE: RNA
<213> ORGANISM: artificial sequence
<220> FEATURE:
<223> OTHER INFORMATION: Synthetic oligonucleotide linker
<220> FEATURE:
<221> NAME/KEY: misc_feature
<222> LOCATION: (1)..(10)
<223> OTHER INFORMATION: 2'-O-methylation

<400> SEQUENCE: 201
uagcggaugc aaaaaaaaaa aaaaaaaa 28

<210> SEQ ID NO 202
<211> LENGTH: 42
<212> TYPE: DNA
<213> ORGANISM: artificial sequence
<220> FEATURE:

-continued

```
<223> OTHER INFORMATION: primer

<400> SEQUENCE: 202

taatacgact catagggaca attactattt acaattacaa tg                        42


<210> SEQ ID NO 203
<211> LENGTH: 39
<212> TYPE: DNA
<213> ORGANISM: artificial sequence
<220> FEATURE:
<223> OTHER INFORMATION: primer

<400> SEQUENCE: 203

aattaaatag cggatgctac accaagacta gaaccgctg                            39


<210> SEQ ID NO 204
<211> LENGTH: 27
<212> TYPE: PRT
<213> ORGANISM: artificial sequence
<220> FEATURE:
<223> OTHER INFORMATION: Clay-binding peptide

<400> SEQUENCE: 204

Gly His Gly Ser Pro Ser Asn Ser His His Gly Ser Lys Lys Cys Asp
1               5                   10                  15

Met Gly Asn Ser Arg Ala Lys Cys Lys Arg Leu
            20                  25


<210> SEQ ID NO 205
<211> LENGTH: 27
<212> TYPE: PRT
<213> ORGANISM: artificial sequence
<220> FEATURE:
<223> OTHER INFORMATION: Clay-binding peptide

<400> SEQUENCE: 205

Ser Asp Arg His Asn Leu Arg Asn Ser Trp Ser Ile Ser Arg His Cys
1               5                   10                  15

Arg Arg Lys Gln Gly Arg Cys Leu Pro Ala His
            20                  25


<210> SEQ ID NO 206
<211> LENGTH: 27
<212> TYPE: PRT
<213> ORGANISM: artificial sequence
<220> FEATURE:
<223> OTHER INFORMATION: Clay-binding peptide

<400> SEQUENCE: 206

Lys Lys Ser Asn Lys Gly His His Pro Ser Ser Lys Gly Lys Gly Pro
1               5                   10                  15

Pro Trp Ser Glu Trp Asp Lys Lys Asn Gly Pro
            20                  25


<210> SEQ ID NO 207
<211> LENGTH: 27
<212> TYPE: PRT
<213> ORGANISM: artificial sequence
<220> FEATURE:
<223> OTHER INFORMATION: Clay-binding peptide

<400> SEQUENCE: 207

Lys Lys Ser Asn Lys Gly Pro His Pro Ser Ser Lys Gly Lys Gly Pro
1               5                   10                  15
```

-continued

```
Pro Trp Ser Glu Trp Asp Lys Lys Asn Gly Pro
            20                  25
```

<210> SEQ ID NO 208
<211> LENGTH: 22
<212> TYPE: PRT
<213> ORGANISM: artificial sequence
<220> FEATURE:
<223> OTHER INFORMATION: Clay-binding peptide

<400> SEQUENCE: 208

```
Val Gly Arg His His Ser Lys Ala Lys Gln Lys Arg Pro His Gly Gly
1               5                   10                  15

Lys Gly Gln Asn Lys Asn
            20
```

<210> SEQ ID NO 209
<211> LENGTH: 22
<212> TYPE: PRT
<213> ORGANISM: artificial sequence
<220> FEATURE:
<223> OTHER INFORMATION: Clay-binding peptide

<400> SEQUENCE: 209

```
Val Gly Arg His His Pro Lys Ala Lys Gln Lys Arg Pro His Gly Gly
1               5                   10                  15

Lys Gly Gln Asn Lys Asn
            20
```

<210> SEQ ID NO 210
<211> LENGTH: 17
<212> TYPE: PRT
<213> ORGANISM: artificial sequence
<220> FEATURE:
<223> OTHER INFORMATION: Clay-binding peptide

<400> SEQUENCE: 210

```
Gly Arg Arg Pro Arg Ala Arg Gly Arg Ser Arg Arg Gly Ser Thr Lys
1               5                   10                  15

Thr
```

<210> SEQ ID NO 211
<211> LENGTH: 19
<212> TYPE: PRT
<213> ORGANISM: artificial sequence
<220> FEATURE:
<223> OTHER INFORMATION: Clay-binding peptide

<400> SEQUENCE: 211

```
Leu Gly Val Ile Arg Asn His Val Val Arg Gly Arg Arg His His Gln
1               5                   10                  15

His Val Arg
```

<210> SEQ ID NO 212
<211> LENGTH: 27
<212> TYPE: PRT
<213> ORGANISM: artificial sequence
<220> FEATURE:
<223> OTHER INFORMATION: Clay-binding peptide

<400> SEQUENCE: 212

```
Gln Pro Gly Arg Pro Thr Glu Val His Pro Glu Leu Val Arg Lys Ser
1               5                   10                  15

Ala Tyr Leu Val Asn Pro Ser Glu Asp Ile Arg
```

-continued

```
            20                  25


<210> SEQ ID NO 213
<211> LENGTH: 27
<212> TYPE: PRT
<213> ORGANISM: artificial sequence
<220> FEATURE:
<223> OTHER INFORMATION: Clay-binding peptide

<400> SEQUENCE: 213

His Arg Ser Glu Lys Pro Lys Asn Val Lys Tyr Lys Arg Gly Tyr Trp
1               5                   10                  15

Glu Arg Gly Asn Gln Lys Lys His Gly Pro Gly
            20                  25


<210> SEQ ID NO 214
<211> LENGTH: 27
<212> TYPE: PRT
<213> ORGANISM: artificial sequence
<220> FEATURE:
<223> OTHER INFORMATION: Clay-binding peptide

<400> SEQUENCE: 214

Gly Ser His Lys Arg Arg Gly Ser Tyr Ala Leu Leu Arg Thr Arg Gly
1               5                   10                  15

Val Gly Arg Gln Ala Glu Leu Glu His Leu Leu
            20                  25


<210> SEQ ID NO 215
<211> LENGTH: 27
<212> TYPE: PRT
<213> ORGANISM: artificial sequence
<220> FEATURE:
<223> OTHER INFORMATION: Clay-binding peptide

<400> SEQUENCE: 215

Val Gly Glu Lys Pro Arg Arg Lys Ser Lys Gly Ala Lys Ala Lys Lys
1               5                   10                  15

Ala Arg Thr Lys Glu Glu Lys Leu Pro Lys Asn
            20                  25


<210> SEQ ID NO 216
<211> LENGTH: 27
<212> TYPE: PRT
<213> ORGANISM: artificial sequence
<220> FEATURE:
<223> OTHER INFORMATION: Clay-binding peptide

<400> SEQUENCE: 216

Asn Lys Gly His Lys Gln Ser Gly Ser Pro Arg His Ser Asn Lys Lys
1               5                   10                  15

Glu Lys Lys Thr Gln Gln Lys Arg Gly Gln Pro
            20                  25


<210> SEQ ID NO 217
<211> LENGTH: 27
<212> TYPE: PRT
<213> ORGANISM: artificial sequence
<220> FEATURE:
<223> OTHER INFORMATION: Clay-binding peptide

<400> SEQUENCE: 217

His Trp Gly Ser Gln His Lys Thr Gly Leu Arg Asn His Lys Arg Ser
1               5                   10                  15
```

-continued

```
Arg Arg Asp Ser Leu Gly Lys Arg Gly Thr Asp
            20                  25


<210> SEQ ID NO 218
<211> LENGTH: 27
<212> TYPE: PRT
<213> ORGANISM: artificial sequence
<220> FEATURE:
<223> OTHER INFORMATION: Clay-binding peptide

<400> SEQUENCE: 218

Lys Gly Trp Gly Ser Ser Ser Gly Pro Pro Gly Leu Thr Gly Lys Ala
1               5                   10                  15

Leu Gly Lys Gly Arg Leu Lys Pro Lys Lys Lys
            20                  25
```

CLAY-BINDING PEPTIDES AND METHODS OF USE

This application claims the benefit of U.S. Provisional Application No. 60/790,149 filed Apr. 6, 2006.

FIELD

Disclosed herein are peptide-based reagents having binding affinity for specific surfaces of clay minerals and their use for various applications, such as papermaking, printing, and personal care.

BACKGROUND

The ubiquitous use of clays in industry makes them prime material candidates for a variety of applications where the modification of the clay surface increases desirable physical traits. One of the drawbacks to using clays as surfaces is that materials that bind to clays are generally not specific and lack specificity as binding agents. So for example where a new coating for a clay is desired, a new search for a clay-binding molecule with the desired property must be conducted. The resulting search is costly in both time and resources and not guaranteed to be successful. A system that is specific to mineral types and can be easily tailored for a variety of applications where the clay is to be used in a variety of applications is needed. The use of peptides as linkers or binders to clays offers some potential in this regard.

Peptides having a binding affinity to polymer and semiconductor surfaces are known. For example, Adey et al., (*Gene* 156:27-31 (1995)) describe peptides that bind to polystyrene and polyvinyl chloride surfaces. Peptides that bind to polyurethane (Murray et al., U.S. Patent Application Publication No. 2002/0098524), polyethylene terephthalate (O'Brien et al., copending and commonly owned U.S. Patent Application Publication No. 2005/0054752), and polystyrene, polyurethane, polycarbonate, and nylon (Grinstaff et al., U.S. Patent Application Publication No. 2003/0185870) have been reported. Additionally, Whaley et al. (*Nature* 405:665-668 (2000)) and Belcher (U.S. Patent Application Publication No. 2003/0148380) disclose the use of phage display screening to identify peptide sequences that can bind specifically to different crystallographic forms of inorganic semiconductor substrates. The use of phage display to identify peptides that specifically bind carbon-based nanostructures is described by Jagota et al. (copending and commonly owned U.S. patent application Ser. No. 10/453,415; WO 03/102020).

Although clays are known to adsorb amino acids, peptides, and proteins (see for example, Dashman et al., *Soil Biol. Biochem.* 19(1):51-55 (1984); and Fusi et al., *Soil Biol. Biochem* 21(7):911-920 (1989)), the use of such biological molecules to target and modify clay surfaces has not been described.

There remains a need therefore for a peptide-based reagent that binds clay and offers flexibility in bringing a wide variety of materials to the clay surface with minimum investment in redesign. Applicants have addressed the stated problem by providing clay-binding peptide (CLAYBP) reagents comprising at least one clay-binding peptide domain (CLAYBD). The clay-binding peptides disclosed herein may further comprise other functional or binding peptide domains allowing for the delivery of benefit agents to the clay surface or for the use of the reagents to adhere clay-containing surfaces.

SUMMARY

Disclosed herein are clay-binding peptide domains that may be incorporated into clay-binding peptide reagents, useful for delivering functional compounds to a clay surface. The clay-binding peptides may comprise active domains that have linker or other functionality or target binding domains that bind various benefit agents that are delivered to the clay surface.

Accordingly, one embodiment disclosed herein provides a peptide reagent having a general structure selected from the group consisting of:

a) $(CLAYBD)_n$;
b) $(CLAYBD_x\text{-}BA_p)_n$;
c) $(CLAYBD_x\text{-}AD_y)_n$;
d) $(CLAYBD_x\text{-}TBD_y)_n$;
e) $[(CLAYBD_x\text{-}L_s)_q\text{-}(TBD_y\text{-}L_t)_r]_n$;
f) $[(CLAYBD_x\text{-}L_s)_q\text{-}(CLAYBD_y\text{-}L_t)_r]_n$;
g) $(CLAYBD_x\text{-}L\text{-}BA)_n$; and
h) $[(CLAYBD)_q\text{-}L_x\text{-}(CLAYBD)_r]_n\text{-}L\text{-}BA$;

wherein:

i) CLAYBD is a clay-binding domain incorporated into a clay-binding peptide;
ii) BA is at least one benefit agent;
iii) AD is at least one active domain incorporated into a clay-binding peptide;
iv) TBD is at least one target-binding domain incorporated into a clay-binding peptide;
v) L is a linker molecule;
vi) n, p, x, y, q, and r independently range from 1-20; and
vii) s and t are each independently 0 or 1, provided that both s and t may not be 0.

Another embodiment disclosed herein provides an affinity complex between a clay and a peptide reagent having a general structure selected from the group consisting of:

a) $clay_m\text{-}(CLAYBD)_n$;
b) $clay_m\text{-}(CLAYBD_x\text{-}BA_p)_n$;
c) $clay_m\text{-}(CLAYBD_x\text{-}AD_y)_n$;
d) $clay_m\text{-}(CLAYBD_x\text{-}TBD_y)_n$;
e) $clay_m\text{-}[(CLAYBD_x\text{-}L_s)_q\text{-}(TBD_y\text{-}L_t)_r]_n$;
e) $clay_m\text{-}[(CLAYBD_x\text{-}L_s)_q\text{-}(CLAYBD_y\text{-}L_t)_r]_n$;
g) $clay_m\text{-}(CLAYBD_x\text{-}L\text{-}BA)_n$; and
h) $clay_m\text{-}[(CLAYBD)_q\text{-}L_x\text{-}(CLAYBD)_r]_n\text{-}L\text{-}BA$;

wherein:

i) clay is a clay moiety;
ii) CLAYBD is a clay-binding domain incorporated into a clay-binding peptide;
iii) BA is at least one benefit agent;
iv) AD is at least one active domain incorporated into a clay-binding peptide;
v) TBD is at least one target binding domain incorporated into a clay-binding peptide;
vi) L is a linker molecule;
vii) m=the number of clay moieties available for binding;
viii) n=is less than or equal to m;
ix) p, x, y, q, and r independently range from 1-20; and
x) s and t are each independently 0 or 1, provided that both s and t may not be 0.

Another embodiment also provides a process of making paper containing a clay comprising:

a) providing an aqueous thickstock suspension comprising cellulosic fibers, and a specific clay in water;
b) diluting the aqueous thickstock suspension of step (a) with water to form an aqueous thinstock suspension;

c) draining the water from the thinstock suspension to form a sheet;

d) drying the sheet;

e) providing a peptide reagent according to of the invention and having a general structure:

$(CLAYBD_x\text{-}TBD_y)_n$ or $[(CLAYBD_x\text{-}L_s)_q\text{-}(TBD_y\text{-}L_t)_r]_n$ where CLAYBD has specific binding affinity for the clay used in step (a) and TBD has specific binding affinity for cellulose;

f) adding the peptide reagent of (e) to any of the following:

i) the clay of (a);

ii) the thickstock of (a);

iii) the thinstock of (b);

whereby paper containing clay is produced.

Another embodiment provides a process for producing a beneficiated and dewatered clay comprising:

(a) providing a clay for which beneficiation is desired;

(b) forming an aqueous suspension of said clay;

(c) deflocculating said aqueous suspension;

(d) adding one or more peptide reagents having the general structure:

$(CLAYBD)_n$ or $[(CLAYBD_x\text{-}L_s)_q\text{-}(CLAYBD_y\text{-}L_t)_r]_n$ where CLAYBD is specific to the clay used in step (a) to produce a flocculated clay product in the suspension; and (e) separating said flocculated clay product from the suspension wherein a beneficiated and dewatered clay is produced.

Another embodiment provides a process for producing a clay-coated paper or paperboard comprising the steps of:

a) forming a base stock;

b) preparing a coating formulation comprising a clay and one or more peptide reagents having the general structure $(CLAYBD_x\text{-}TBD_y)_n$ or $[(CLAYBD_x\text{-}L_s)_q\text{-}(TBD_y\text{-}L_t)_r]_n$, in water;

c) coating at least one side of the base stock with the coating formulation; and d) passing the coated base stock through a calender device wherein a clay-coated paper or paperboard is produced.

Another embodiment provides a method of producing an intercalated clay comprising: contacting a clay, having adjacent clay platelets, with a composition comprising one or more peptide reagents described above to achieve intercalation of said peptide reagent between said adjacent clay platelets in an amount sufficient to space said adjacent clay platelets a distance of at least about 10 Å; wherein the peptide reagent comprises a clay-binding domain specific for the clay and the composition comprises at least about 2% by weight of the peptide reagent, Yet another embodiment provides a method of producing an exfoliated clay comprising:

a) contacting a clay, having adjacent clay platelets, with a composition comprising one or more peptide reagents as described above to achieve intercalation of said peptide reagent between said adjacent clay platelets in an amount sufficient to space said adjacent clay platelets a distance of at least about 10 Å; and b) separating the platelets of the intercalated clay;

wherein the peptide reagent comprises a clay-binding domain specific for the clay and the composition comprises at least about 2% by weight of the peptide reagent, Other embodiments also provide processes for identifying peptides that bind selectively to an edge of clay platelets, to both the faces and edges of clay platelets, and to the face of clay platelets.

In a preferred embodiment peptides of the present invention comprise cDNA-RNA-peptide complexes and are generated combinatorially by a method comprising the steps of:

a) providing a library of DNA molecules encoding a peptide;

b) transcribing, in vitro, the DNA to the corresponding RNA molecule;

c) fusing an oligonucleotide linker to the RNA transcribed RNA molecule of (b);

d) translating the RNA molecule to the corresponding peptide wherein an RNA-peptide complex is formed through the linker; and e) reverse transcribing the RNA portion of the RNA-peptide complex to generate the corresponding cDNA to form cDNA-RNA-peptide complex.

In another embodiment the invention provides a clay binding peptide selected from the group consisting of SEQ ID NO:204-218.

Additionally, other embodiments provide methods for binding a substrate comprising at least one clay moiety to a target, for delivering a benefit agent to a substrate comprising clay or a clay moiety, and for adhering two surfaces.

BRIEF DESCRIPTION OF THE FIGURES, BIOLOGICAL DEPOSITS AND SEQUENCE DESCRIPTIONS

The various embodiments of the invention can be more fully understood from the following detailed description, figures and the accompanying sequence descriptions, which form a part of this application.

Figure 1A:
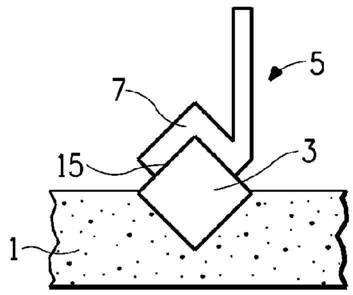
FIG. 1 is a set of panels A-E which depict some embodiments disclosed herein as they are bound to a surface containing, in whole or in part, clay particles.
Figure 1B:
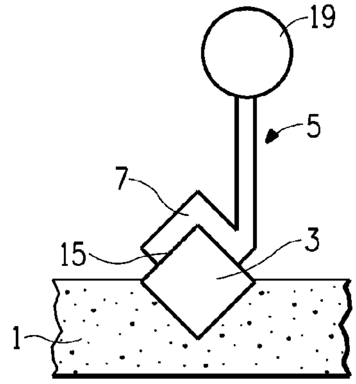
Figure 1C:
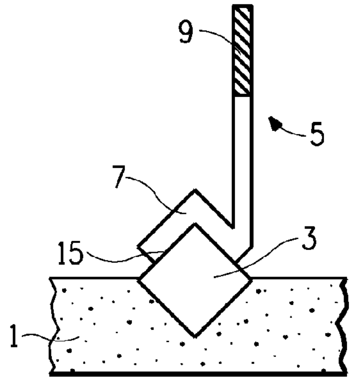
Figure 1D:
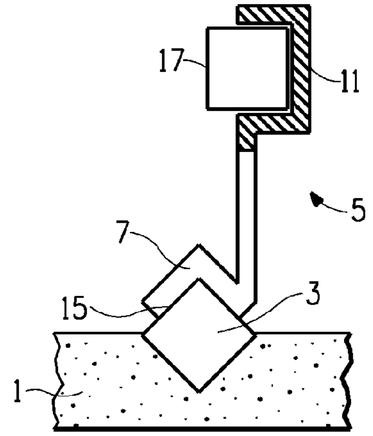
Figure 1E:
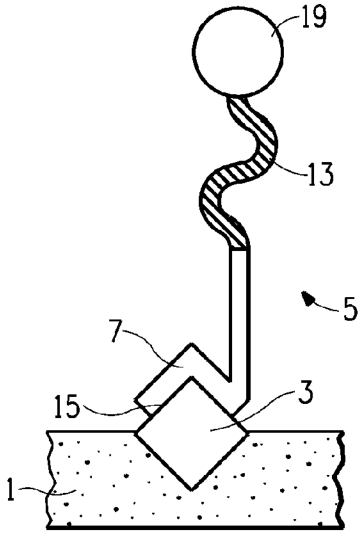

The following sequences conform with 37 C.F.R. 1.821-1.825 ("Requirements for Patent Applications Containing Nucleotide Sequences and/or Amino Acid Sequence Disclosures—the Sequence Rules") and consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NOs: 1-12 are poly(methyl methacrylate) (PMMA) binding peptide sequences.

SEQ ID NOs:13-41 are antimicrobial peptide sequences.

SEQ ID NOs: 42-66 are pigment binding peptide sequences.

SEQ ID NOs: 67-79 are print media binding peptide sequences, SEQ ID NOs: 67 and 68 bind to cotton fabric, SEQ ID NOs: 67 and 69 bind to polyester/cotton fabric, SEQ ID NOs: 67, and 70-72 bind to HAMERMILL® paper, SEQ ID NOs: 73-78 bind to cellulose, and SEQ ID NO: 79 binds to poly(ethylene terephthalate).

SEQ ID NOs: 80-175, and 195-198 are body surface binding peptide sequences, SEQ ID NOs: 80-87 are skin-binding peptide sequences, SEQ ID NOs: 88-175, and 195-198 are hair binding peptide sequences and SEQ ID NOs: 88 and 89 bind nails as well as hair.

SEQ ID NO:176 is the amino acid sequence of the Caspase 3 cleavage site that may be used as a peptide linker domain.

SEQ ID NOs: 177-179 are amino acid sequences of peptide linker domains.

SEQ ID NOs: 180-185 are the amino acid sequences of nylon-binding peptides.

SEQ ID NOs: 186-194 are the amino acid sequences of poly(tetrafluoroethylene)-binding peptides.

SEQ ID NO: 199 is the amino acid sequence of the N-terminal constant region used in the present display library.

SEQ ID NO: 200 is the amino acid sequence of the C-terminal constant region used in the present display library.

SEQ ID NO: 201 is the nucleic acid sequence of the oligonucleotide portion of the MHA-oligonucleotide linker used in preparing the fusion molecules.

SEQ ID NOs: 202 and 203 are primers.

SEQ ID NOs: 204-218 are the amino acid sequences of clay binding peptides (CLAYBP) identified by biopanning.

DETAILED DESCRIPTION

Disclosed herein are variable coatings for clay substrates and surfaces. More specifically, peptide sequences that bind clay with a high affinity are described. These peptides can be bound covalently or otherwise to known substances to adapt clay for a variety of uses. Additionally, methods to develop, produce, and use such peptides are disclosed.

The following definitions and abbreviations are to be used for the interpretation of the claims and the specification.

As used herein, the term "comprising" means the presence of the stated features, integers, steps, or components as referred to in the claims, but that it does not preclude the presence or addition of one or more other features, integers, steps, components or groups thereof.

As used herein, the term "about" means modifying the quantity of an ingredient or reactant of the invention or employed and refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", the claims include equivalents to the quantities.

As used herein, "BA" means benefit agent.

As used herein, "CLAY" or "clay" means a clay mineral.

As used herein, "CLAYBP" means clay-binding peptide. A clay-binding peptide is a peptide having specific affinity for a specific clay. Clay-binding peptides of the present invention are single chain peptides no more than 200 amino acids in length. As such, the present clay-binding peptides specifically exclude $F_{ab}$ fragments and single chain fused variable (scFv) antibody molecules. Clay-binding peptides may comprise various subdomains including but not limited to active domains, target domains and linker domains. Within any given clay binding peptide there resides a "clay binding domain" (CLAYBD) having affinity to clay. In one embodiment, the claying-binding peptides are no more than 100 amino acids in length, preferably about 7 to about 100 amino acids in length, more preferably about 7 to about 60 amino acids in length, even more preferably about 7 to about 30 amino acids in length, and most preferably about 15 to about 30 amino acids in length. In another embodiment, the clay-binding peptide is selected from the group consisting of SEQ NOs: 204, 205, 206, 207, 208, 209, 210, 211, 212, 213, 214, 215, 216, 217, and 218.

As used herein, "CLAYBD" means clay-binding domain. The clay binding domain ranges from about 7 to about 100 amino acids in length, preferably about 7 to about 60 amino acids in length, and more preferably about 7 to about 30 amino acids in length, and most preferably 15 to about 30 amino acids in length. Any given clay-binding peptide may contain only the clay binding domain or may contain this domain in conjunction with active or target domains having different functionality.

The term "peptide" refers to a single chain polymer of two or more amino acids joined to each other by peptide bonds or modified peptide bonds.

The term "body surface" will mean any surface of the human body that may serve as a substrate for the binding of a peptide carrying a benefit agent. Typical body surfaces include but are not limited to hair, skin, nails, and teeth.

The term "benefit agent" is a general term applying to a compound or substance that may be coupled with a complex of clay and clay-binding peptide in order to provide a desirable characteristic of the benefit agent to the complex. In the most general sense a benefit agent may be any element, molecule or compound that is not a clay-binding peptide. Benefit agents typically include colorants such as pigments and dyes as well as pharmaceuticals, markers, conditioners, and fragrances. Clay itself may be a benefit agent because it may act as a pigment or a skin conditioning agent.

The term "hair" as used herein refers to human hair, eyebrows, and eyelashes.

The term "skin" as used herein refers to human skin, or substitutes for human skin, such as pig skin, Vitro-Skin® and EpiDerm™. Skin as used herein as a body surface will generally comprise a layer of epithelial cells and may additionally comprise a layer of endothelial cells.

The term "nails" as used herein refers to human fingernails and toenails.

The terms "coupling" and "coupled" as used herein refer to any chemical association and includes both covalent and non-covalent interactions.

The term "pigment" refers to an insoluble, organic or inorganic colorant.

The term "print medium" refers to any substrate suitable for printing.

The term "dispersant" as used herein refers to a substance that stabilizes the formation of a colloidal solution of solid pigment particles in a liquid medium.

The term "active domain" as used herein applies to a subsequence of amino acids within a clay binding peptide. An active domain is a portion of the clay binding peptide that is not responsible for clay binding but provides additional functionality or benefit. In one embodiment for example an active domain may have antimicrobial functionality. In another embodiment the active domain may have a linker function between two other domains or between the peptide and a benefit agent. In another embodiment the active domain may serve to bind a specific target analyte (target domain).

The term "linking domain" or "linker domain" as used herein applies to a particular type of active domain that is used to either link two domains together, as a separator between two domains, or a domain and a terminal end. Linking domains may have a function beyond joining or separating two domains of a peptide.

The term "target binding domain" as used herein applies to a particular type of peptide active domain that binds a target molecule, element, compound, or complex. The binding substrate for the target binding domain is referred to herein as the "target". Typical targets will include but are not limited to biological analytes, (cells, cell membrane fractions, viral proteins, proteins, antibodies, antibody fragments, nucleic acids and the like), plant fibers, synthetic fibers, as well as organic and inorganic target complexes that will typically be found on surfaces or in print media. All target binding domains are active domains. A "body surface binding domain" is a target domain that has specific affinity for a body surface such as hair, skin, nails, teeth and the like. Similarly a "print media binding domain" will function to bind the elements of print media such as paper and other ink receptive surfaces. Within the context of print media domains there may be those domains that bind cellulose or cotton or other plant fibers. Additionally the target domains disclosed herein may be selected to bind specific benefit agents such as colorants (pigments, dyes) and conditioners or any other organic or inorganic complex.

As used herein, the term "clay moiety" means a discrete substance comprising a specific clay that serves as a binding site for a clay-binding peptide. Clay moieties may make up a clay particle, or be comprised within various clay coatings on surfaces and substrates.

As used herein, the term "linker" or "spacer" or "linker molecule" or "spacer molecule" will be used interchangeably and will mean a molecule or compound used to bind a benefit agent to the clay-peptide complex. Any material that can bind said benefit agent to the complex can be used, including peptide based molecules. A linker molecule is distinct from a linker domain in that linker domains are inherently part of, or are proposed to be part of a peptide further comprising a clay-binding domain. A linker molecule, in whole or in part, may be identical to a linking domain, but a linking molecule does not contain a clay-binding domain.

As referred to herein a substance has "binding functionality" when it demonstrates specific affinity for a substance or target.

As referred to herein a substance has "catalytic functionality" when it demonstrates the ability to catalyze a chemical reaction.

As referred to herein a substance has "antimicrobial functionality" when it demonstrates the ability to kill microbial cell populations.

As used herein the term "surface" when used in conjunction with a clay moiety means the point of contact for the clay moiety. Surfaces disclosed herein may be coated with clay or will typically themselves comprise clay moieties. In some instances the surface disclosed herein may be layered or juxtaposed on a "secondary surface". A "secondary surface" will typically be coated or layered with the clay surfaces disclosed herein.

The term "affinity complex" refers to a complex between a clay and a clay-binding peptide reagent. The affinity complex may optionally comprise a benefit agent.

The term "stringency" as it is applied to the selection of clay-binding peptides, hair-binding, skin-binding, and nail-binding peptides disclosed herein, refers to the concentration of the eluting agent (usually detergent) used to elute peptides from the substrate to which they are bound or for which they have affinity. Higher concentrations of the eluting agent provide more stringent conditions.

The term "thinstock" refers to a dilute aqueous suspension of cellulosic fibers and filler used in making filled paper.

The term "thickstock" refers to a concentrated aqueous suspension of cellulosic fibers and filler used in making filled paper. The thickstock is diluted, typically with white water from the drainage stage, to prepare the thinstock.

The term "whitewater" refers to the filtrate water from the papermaking process. The terms thinstock, thickstock and whitewater are well known to those in the paper-making industry.

"Layered Material" refers to an inorganic material, such as a smectite clay mineral, that is in the form of a plurality of adjacent, bound layers and has a maximum thickness, for each layer, of about 100 Å.

"Platelets" refers to individual layers of the Layered Material.

"Intercalate" or "Intercalated" refers to a Layered Material that includes oligomer and/or polymer molecules disposed between adjacent platelets of the Layered Material to increase the interlayer spacing between the adjacent platelets to at least 10 Å.

"Intercalation" refers to a process for forming an Intercalate.

"Exfoliate" or "Exfoliated" refers to individual platelets of an Intercalated Layered Material so that adjacent platelets of the Intercalated Layered Material can be dispersed individually throughout a carrier material, such as a matrix polymer.

"Exfoliation" refers to a process for forming an Exfoliate from an Intercalate.

"Nanocomposite" refers to an oligomer, polymer or copolymer having dispersed therein a plurality of individual platelets obtained from an Exfoliated, Intercalated Layered Material.

"Matrix Polymer" refers to a thermoplastic or thermosetting polymer in which the Exfoliate is dispersed to form a Nanocomposite.

"Intercalant Polymer" or "Intercalant" refers to an oligomer or polymer that is sorbed between Platelets of the Layered Material to form an Intercalant.

The term, to "blunge" refers to the process of amalgamating or blending; to beat up or mix in water, as clay.

The term "amino acid" refers to the basic chemical structural unit of a protein or polypeptide. The following abbreviations are used herein to identify specific amino acids:

| Amino Acid | Three-Letter Abbreviation | One-Letter Abbreviation |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |

-continued

| Amino Acid | Three-Letter Abbreviation | One-Letter Abbreviation |
|---|---|---|
| Proline | Pro | P |
| Serine | Ser | S |
| Threonine | Thr | T |
| Tryptophan | Trp | W |
| Tyrosine | Tyr | Y |
| Valine | Val | V |
| Any amino acid | Xaa | X |

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. A "foreign" gene refers to a gene not normally found in the host organism, but that is introduced into the host organism by gene transfer. Foreign genes can comprise native genes inserted into a non-native organism, or chimeric genes.

"Synthetic genes" can be assembled from oligonucleotide building blocks that are chemically synthesized using procedures known to those skilled in the art. These building blocks are ligated and annealed to form gene segments which are then enzymatically assembled to construct the entire gene. "Chemically synthesized", as related to a sequence of DNA, means that the component nucleotides were assembled in vitro. Manual chemical synthesis of DNA may be accomplished using well-established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing site, effector binding site and stem-loop structure.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The term "expression", as used herein, refers to the process by which a gene's coded information is converted into the structures present and operating in the cell. Expressed genes include those that are transcribed into mRNA and then translated into protein and those that are transcribed into RNA but not translated into protein (e.g., transfer and ribosomal RNAS). Expression may also refer to translation of mRNA into a polypeptide.

The term "transformation" refers to the transfer of a nucleic acid fragment into the genome of a host organism, resulting in genetically stable inheritance. Host organisms containing the transformed nucleic acid fragments are referred to as "transgenic" or "recombinant" or "transformed" organisms.

The term "host cell" refers to cell which has been transformed or transfected, or is capable of transformation or transfection by an exogenous polynucleotide sequence.

The terms "plasmid", "vector" and "cassette" refer to an extra chromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitate transformation of a particular host cell. "Expression cassette" refers to a specific vector containing a foreign gene and having elements in addition to the foreign gene that allow for enhanced expression of that gene in a foreign host.

The term "phage" or "bacteriophage" refers to a virus that infects bacteria. Altered forms may be used for the purposes disclosed herein. The preferred bacteriophage is derived from the "wild" phage, called M13. The M13 system can grow inside a bacterium, so that it does not destroy the cell it infects but causes it to make new phages continuously. It is a single-stranded DNA phage.

The term "phage display" refers to the display of functional foreign peptides or small proteins on the surface of bacteriophage or phagemid particles. Genetically engineered phage may be used to present peptides as segments of their native surface proteins. Peptide libraries may be produced by populations of phage with different gene sequences.

The term "mRNA display" is an in vitro selection technique used to obtain from libraries of diverse sequences peptides and proteins that have an affinity for a target ligand/material (U.S. Pat. No. 6,258,558). The process relies on mRNA-protein fusion molecules, which consist of peptide or protein sequences covalently linked via their C-termini to the 3' end of their own mRNA (these molecules are commercially referred to as PROfusion™ molecules; Adnexus Therapeutics, Weltham, Mass.). The library of PROfusion™ molecules is preferably subjected to reverse transcription (i.e. transcribed into a library of cDNA/RNA-protein fusion molecules) prior affinity selection. The library of fusion molecules is subjected to repetitive rounds of in vitro selection in the presence of target (typically a solid or immobilized on a solid support). A series of washing steps are used to select the fusion molecules exhibiting an affinity for the target material. The stringency of the washing is adjusted to select the fusion molecules those with the highest affinity (the affinity of the fusion molecule for the target material is attributed to the specific peptide sequence displayed). Selected fusion molecules are then subsequently subjected to PCR amplification. The end result is a pool of nucleotide sequences encoding peptides which have an affinity for the target ligand. The process is typically repeated for several cycles and may also include mutagenesis (e.g. error prone PCR) to evolve and identify proteins having improved affinity for the target ligand.

Standard recombinant DNA and molecular cloning techniques used herein are well known in the art and are described by Sambrook, J. and Russell, D., *Molecular Cloning: A Laboratory Manual*, Third Edition, Cold Spring Harbor Laboratory Press, Cold Spring Harbor, N.Y. (2001); and by Silhavy, T. J., Bennan, M. L. and Enquist, L. W., *Experiments with Gene Fusions*, Cold Spring Harbor Laboratory Cold Press Spring Harbor, N.Y. (1984); and by Ausubel, F. M. et. al., *Short Protocols in Molecular Biology,* $5^{th}$ Ed. Current Protocols and John Wiley and Sons, Inc., N.Y., 2002.

The disclosures herein relate to peptides and peptide reagents that have specific binding affinity to clay in various conformations including complexes of the clay-binding peptides linked to benefit agents, and optionally where the clay-binding peptides comprise active peptide domains or target binding domains having binding or other functionality for other substances or surfaces. The peptide reagents disclosed herein may take a variety of forms including, but not limited to, those represented by the following structures:

a) $(CLAYBD)_n$;
b) $(CLAYBD_x\text{-}BA_p)_n$;
c) $(CLAYBD_x\text{-}AD_y)_n$;
d) $(CLAYBD_x\text{-}TBD_y)_n$;
e) $[(CLAYBD_x\text{-}L_s)_q\text{-}(TBD_y\text{-}L_t)_r]_n$;
f) $[(CLAYBD_x\text{-}L_s)_q\text{-}(CLAYBD_y\text{-}L_t)_r]_n$;
g) $(CLAYBD_x\text{-}L\text{-}BA)_n$; and
h) $[(CLAYBD)_q\text{-}L_x\text{-}(CLAYBD)_r]_n\text{-}L\text{-}BA$;

wherein:

i) CLAYBD is a clay-binding domain incorporated into a clay-binding peptide;
ii) BA is at least one benefit agent;
iii) AD is at least one active domain incorporated into a clay-binding peptide;
iv) TBD is at least one target binding domain incorporated into a clay-binding peptide;
v) L is a linker molecule;
vi) n, p, x, y, q, and r independently range from 1-20; and
vii) s and t are each independently 0 or 1, provided that both s and t may not be 0.

Alternatively the clay-binding peptide reagents disclosed herein may be part of an affinity complex between a clay and a peptide reagent represented by the general structures:

a) $clay_m\text{-}(CLAYBD)_n$;
b) $clay_m\text{-}(CLAYBD_x\text{-}BA_p)_n$;
c) $clay_m\text{-}(CLAYBD_x\text{-}AD_y)_n$;
d) $clay_m\text{-}(CLAYBD_x\text{-}TBD_y)_n$;
e) $clay_m\text{-}[(CLAYBD_x\text{-}L_s)_q\text{-}(TBD_y\text{-}L_t)_r]_n$;
f) $clay_m\text{-}[(CLAYBD_x\text{-}L_s)_q\text{-}(CLAYBD_y\text{-}L_t)_r]_n$;
g) $clay_m\text{-}(CLAYBD_x\text{-}L\text{-}BA)_n$; and
h) $clay_m\text{-}[(CLAYBD)_q\text{-}L_x\text{-}(CLAYBD)_r]_n\text{-}L\text{-}BA$;

wherein:

i) clay is a clay moiety;
ii) CLAYBD is a clay-binding domain incorporated into a clay-binding peptide;
iii) BA is at least one benefit agent;
iv) AD is at least one active domain incorporated into a clay-binding peptide;
v) TBD is at least one target binding domain incorporated into a clay-binding peptide;
vi) L is a linker molecule;
vii) m=the number of clay moieties available for binding;
viii) n=is less than or equal to m;
ix) p, x, y, q, and r independently range from 1-20; and
x) s and t are each independently 0 or 1, provided that both s and t may not be 0.

Clay Moieties

A clay moiety, as defined herein, is the binding site of a clay-binding peptide on a surface. The clay moiety may be incorporated into a surface in various ways. For example, the surface may be the surface of a clay substrate. Alternatively, the clay moiety may be imbedded into the surface of another material, such as a polymer, or coated on the surface of another material, such as a metal, polymer, glass, cloth, and the like. The term "clay", as used and defined herein, refers to clay minerals which are comprised of certain groups of hydrous aluminum, magnesium, and iron silicates that may contain sodium, calcium, potassium, and other ions. Suitable clays for use in the embodiments disclosed herein include, but are not limited to, the kaolinite group: kaolinite, dickite, nacrite, halloysite, hisingerite; the montmorillonite/smectite group: beidellite, pyrophyllite, talc, vermiculite, sauconite, saponite, nontronite and montmorillonite; the illite (or the clay-mica) group: muscovite, illite; and the chlorite group: amesite, baileychlore, chamosite, clinochlore, kaemmererite, cookeite, corundophilite, daphnite, delessite, gonyerite, nimite, odinite, orthochamosite, penninite, pannantite, rhipidolite, prochlore, sudoite, thuringite. Other clay minerals include albites, phillipsites, analcites, and gibbsites. Additionally, the term "clay" as used herein, includes the broader class of minerals termed phyllosilicates. Phyllosilicates are sheet silicates in that they form parallel sheets of silicate tetrahedra with a composition of $Si_2O_5$ or a 2:5 ratio of silicon to oxygen. They include the serpentine group of antigorite and chrysotile; the clay mineral group (as described above, the mica group which includes muscovite, phlogopite, biotite, lepidolite, and margarite; the chlorite group; the apophyllite group; and the prehnite group. Various types of clays are available commercially from companies such as Thiele Kaolin Co. (Sandersville, Ga.), Imerys (Roswell, Ga.), Dry Branch Kaolin Co. (Dry Branch, Ga.), Millennium Inorganic Chemicals (Baltimore, Md.), and Minerals Technology Inc. (Specialty Minerals, Bethlehem, Pa.).

In one embodiment, the clay is coated onto another surface, such as metal, polymer, glass, cloth, paper, cardboard and the like, using methods known in the art, such as spraying, brushing, dip coating and casting. For example, kaolin is widely used in the paper industry as a coating and as a filler. The object of coating paper or cardboard with clays such as kaolin is to smooth over the fine structure of the base paper to enable high quality ink transfer. The use of clays in the paper industry is described in more detail below.

In another embodiment, the clay is imbedded into the surface of another material, such as polymers, ceramics, rubbers, inks, catalysts, paints, and fiberglass. This may be done by adding particles, beads, or fragments of clay material into the other material as it is prepared.

Identification of Clay-Binding Peptide Domains

Peptides having affinity for clay, referred to herein as clay-binding peptides (CLAYBP), are peptide sequences that bind strongly to a clay moiety. The clay-binding peptides comprise at least one clay binding domain (CLAYBD) and may further comprises various subdomains, including but not limited to active domains, target domains, and linker domains, as described above. Any given clay-binding peptide may contain only the clay binding domain or may contain the clay binding domain in conjunction with one or more subdomains. The clay-binding domain is the segment of the clay-binding peptide that has a high binding affinity for a particular clay. The clay-binding domains are from about 7 amino acids to about 100 amino acids, more preferably, from about 7 amino acids to about 60 amino acids, even more preferably from about 7 to about 30 amino acids, and most preferably about 15 to about 30 amino acids in length. Suitable clay-binding domains may be selected using methods that are well known in the art.

The clay-binding domains may be generated randomly and then selected against a clay substrate based upon their binding affinity for clay, using the methods described by O'Brien et al. (copending and commonly owned U.S. Patent Application Publication No. 2005/0054752), Adey et al., (*Gene* 156:27-31, (1995)), Murray et al. (U.S. Patent Application Publication No. 2002/0098524) and Grinstaff et al. (U.S. Patent Application Publication No. 2003/0185870), all of which are incorporated herein by reference. The generation of random libraries of peptides is well known and may be accomplished by a variety of techniques including, bacterial display (Kemp, D. J.; *Proc. Natl. Acad. Sci. USA* 78(7):4520-4524 (1981), and Helfman et al., *Proc. Natl. Acad. Sci. USA* 80(1):31-35, (1983)), yeast display (Chien et al., *Proc Natl Acad Sci USA* 88(21):9578-82 (1991)), combinatorial solid phase peptide synthesis (U.S. Pat. No. 5,449,754, U.S. Pat. No. 5,480,971, U.S. Pat. No. 5,585,275, U.S. Pat. No. 5,639,603), phage display technology (U.S. Pat. No. 5,223,409, U.S. Pat. No. 5,403,484, U.S. Pat. No. 5,571,698, U.S. Pat. No. 5,837,500), ribosome display technology (U.S. Pat. No. 5,643,768; U.S. Pat. No. 5,658,754; and U.S. Pat. No. 7,074,557), and mRNA display technology (U.S. Pat. No. 6,258,558; U.S. Pat. No. 6,518,018; U.S. Pat. No. 6,281,344; U.S. Pat. No. 6,214,553; U.S. Pat. No. 6,261,804; U.S. Pat. No. 6,207,446; U.S. Pat. No. 6,846,655; U.S. Pat. No. 6,312,927; U.S. Pat. No. 6,602,685; U.S. Pat. No. 6,416,950; U.S. Pat. No. 6,429,300; U.S. Pat. No. 7,078,197; U.S. Pat. No. 6,436,665; U.S. Pat. No. 6,361,943; and U.S. Pat. No. 6,228,994). The combination of technologies described above will be referred to herein generally for convenience as "combinatorial" peptide generation.

Phage Display

Phage display is an in vitro selection technique in which a peptide or protein is genetically fused to a coat protein of a bacteriophage, resulting in display of fused peptide on the exterior of the phage virion, while the DNA encoding the fusion resides within the virion. This physical linkage between the displayed peptide and the DNA encoding it allows screening of vast numbers of variants of peptides, each linked to a corresponding DNA sequence, by a simple in vitro selection procedure called "biopanning". As used herein, "biopanning" may be used to describe any in vitro selection procedure (phage display, ribosome display, mRNA-display, etc.) where a library of displayed peptides a library of displayed peptides is panned against a specified target material (e.g. clay). In its simplest form, phage display biopanning is carried out by incubating the pool of phage-displayed variants with a target of interest that has been immobilized on a plate or bead, washing away unbound phage, and eluting specifically bound phage by disrupting the binding interactions between the phage and the target. The eluted phage is then amplified in vivo and the process is repeated, resulting in a stepwise enrichment of the phage pool in favor of the tightest binding sequences. After 3 or more rounds of selection/amplification, individual clones are characterized by DNA sequencing.

Specifically, the clay-binding domains may be selected using the following method. A suitable library of phage-peptides is generated using the methods described above or the library is purchased from a commercial supplier. After the library of phage-peptides has been generated, they are then contacted with an appropriate amount of the clay substrate. The library of phage-peptides is dissolved in a suitable solution for contacting the substrate. The test substrate may be suspended in the solution or may be immobilized on a plate or bead. A preferred solution is a buffered aqueous saline solution containing a surfactant. A suitable solution is Tris-buffered saline (TBS) with 0.5% TWEEN® 20. The solution may additionally be agitated by any means in order to increase the mass transfer rate of the peptides to the clay substrate, thereby shortening the time required to attain maximum binding.

Upon contact, a number of the randomly generated phage-peptides will bind to the clay substrate to form a phage-peptide-substrate complex. Unbound phage-peptide may be removed by washing. After all unbound material is removed, phage-peptides having varying degrees of binding affinities for the clay substrate may be fractionated by selected washings in buffers having varying stringencies. Increasing the stringency of the buffer used increases the required strength of the bond between the phage-peptide and clay substrate in the phage-peptide-substrate complex.

A number of substances may be used to vary the stringency of the buffer solution in peptide selection including, but not limited to, acidic pH (1.5-3.0); basic pH (10-12.5); high salt concentrations such as $MgCl_2$ (3-5 M) and LiCl (5-10 M); water; ethylene glycol (25-50%); dioxane (5-20%); thiocyanate (1-5 M); guanidine (2-5 M); urea (2-8 M); and various concentrations of different surfactants such as SDS (sodium dodecyl sulfate), DOC (sodium deoxycholate), Nonidet P-40, Triton X-100, TWEEN® 20, wherein TWEEN® 20 is preferred. These substances may be prepared in buffer solutions including, but not limited to, Tris-HCl, Tris-buffered saline, Tris-borate, Tris-acetic acid, triethylamine, phosphate buffer, and glycine-HCl, wherein Tris-buffered saline solution is preferred.

It will be appreciated that phage-peptides having increasing binding affinities for the clay substrate may be eluted by repeating the selection process using buffers with increasing stringencies. The eluted phage-peptides can be identified and sequenced by any means known in the art.

In one embodiment, the following method for generating the clay-binding peptides disclosed herein may be used. A library of combinatorially generated phage-peptides is contacted with a clay substrate to form phage peptide-substrate complexes. The phage-peptide-substrate complex is separated from uncomplexed peptides and unbound substrate, and the bound phage-peptides from the phage-peptide-substrate complexes are eluted from the complex, preferably by acid treatment. Then, the eluted phage-peptides are identified and sequenced. To identify peptide sequences that bind to clay but not to other substrates, a subtractive panning step may be added. Specifically, the library of combinatorially generated phage-peptides is first contacted with the non-target to remove phage-peptides that bind to it. Then, the non-binding phage-peptides are contacted with clay and the above process is followed. Alternatively, the library of combinatorially generated phage-peptides may be contacted with the non-target and clay simultaneously. Then, the phage-peptide-substrate complexes are separated from the phage-peptide-non-target complexes and the method described above is followed for the desired phage-substrate complexes.

Alternatively, a modified phage display screening method for isolating peptides with a higher affinity for clay substrates may be used. In the modified method, the phage-peptide-substrate complexes are formed as described above. Then, these complexes are treated with an elution buffer. Any of the elution buffers described above may be used. Preferably, the elution buffer is an acidic solution. Then, the remaining, elution-resistant phage-peptide-substrate complexes are used to directly infect/transfect a bacterial host cell, such as *E. coli* ER2738. The infected host cells are grown in an appropriate growth medium, such as LB (Luria-Bertani) medium, and this culture is spread onto agar, containing a suitable growth medium, such as LB medium with IPTG (isopropyl β-D-thiogalactopyranoside) and S-Gal™. After growth, the plaques are picked for DNA isolation and sequencing to identify the peptide sequences with a high binding affinity for the substrate of interest. Alternatively, PCR may be used to identify the elution-resistant phage-peptides from the modified phage display screening method, described above, by directly carrying out PCR on the phage-peptide-substrate complexes using the appropriate primers, as described by Janssen et al. in U.S. Patent Application Publication No. 2003/0152976, which is incorporated herein by reference.

mRNA-Display

An in vitro method commonly used for identifying peptides having an affinity for a target material is mRNA-display (U.S. Pat. No. 6,258,558). Briefly, a random library of DNA molecules is generated wherein they encode a peptide of a desired length. The length of the peptide within the display library is may be to be up to 200 amino acids in length and is typically designed to range from about 7 to about 100 amino acids in length. In one embodiment, the library of peptides are designed to be about 7 to about 60 amino acids in length, preferably about 7 to about 30 amino acids in length, more preferably about 15 to about 30 amino acids in length, and most preferably about 27 amino acids in length (i.e. a "27-mer" library). Typically, the nucleic acid molecule encoding the peptide includes (in addition to the coding region) appropriate 5' and 3' regulatory regions necessary for efficient in vitro transcription and translation. The design of the nucleic acid constructs used for preparing the mRNA display library is well known to one of skill in the (see WO2005/051985). The nucleic acid molecules can be designed to optionally encode flexible linkers, cleavage sequences, fusion promoting sequences, and identification/purification tags (e.g., poly-A regions, His tags, etc.) to facility purification and/or processing in subsequence steps.

The library of random nucleic acid fragments is transcribed in vitro to produce an mRNA library. The mRNA is isolated and subsequently fused to a linker molecule (i.e. a puromycin-oligonucleotide linker or a puromycin derivative-oligonucleotide linker; i.e. derivatives such as 3'-[α-amino-p-methoxy-hydrocinnamido]-3'-deoxy-adenosine; a.k.a. "MHA") using techniques well-known in the art (U.S. Pat. No. 6,258,558; U.S. Pat. No. 6,228,994; and Kurz et al., *NAR,* 28(18):e83 i-v (2000)). In a preferred embodiment, the puromycin-oligonucleotide linker comprises psoralen for rapid and facile preparation of the mRNA-protein fusions (Kurtz et al., supra). The mRNA-puromycin fusion molecules are then translated in vitro whereby the nascent polypeptide is fused (via the puromycin-oligonucleotide linker) to the mRNA (PROFUSION™ molecules; Adnexus Therapeutics, Weltham, Mass.). In this way, the phenotype (peptide) is linked to the corresponding genotype (RNA).

The mRNA-peptide fusion molecules are typically reverse transcribed into a cDNA-mRNA-protein fusion molecules prior to affinity selection. The library (often comprising up to $10^{13}$ different sequences) is contacted with target ligand/material (typically an immobilized target and/or solid surface). The selection process is carried out in an aqueous medium wherein parameters such as time, temperature, pH, buffer, salt concentration, and detergent concentration may be varied according the stringency of the selection strategy employed. Typically, the temperature of the incubation period ranges from 0° C. to about 40° C. and the incubation time ranges from about 1 to about 24 hours. The selection process is carried out in an aqueous medium wherein additional parameters such as pH, buffer, salt concentration, and detergent concentration may be varied according the stringency of the selection strategy employed.

Several washing steps are typically used to remove the non-binding/low affinity fusion molecules. The stringency of the washing conditions is adjusted to select those fusion molecules having the highest affinity for the target material (e.g. clay). The high affinity fusion molecules are isolated and then PCR-amplified in order to obtain the nucleic acid sequences encoding the clay-binding peptides. In one embodiment, the cDNA is isolated from the target material prior to PCR amplification as the material may adversely impact PCR efficiency). The mRNA display selection cycle is typically repeated for 3 to 10 cycles (or more) in order to select/enrich those fusion molecules comprising peptide sequences exhibiting the highest affinity for the target material.

Error prone PCR may optionally be incorporated into mRNA display selection process whereby mutants derived from a previously selected high affinity sequence are used. The process is typically repeated for several cycles in order to obtain the peptides having improved affinity for the target material (e.g. clay). In one embodiment, the clay-binding peptide is selected from the group consisting of SEQ NOs: 204, 205, 206, 207, 208, 209, 210, 211, 212, 213, 214, 215, 216, 217, and 218.

Optionally, any clay-binding peptide sequence identified using mRNA display is verified using the free peptide. Typically, the nucleic acid molecule encoding the clay-binding peptide is cloned and recombinantly expressed in an appropriate microbial host cell, such as *E. coli*. The free peptide is then isolated and assayed against the targeted material to validate the binding affinity of the peptide sequence.

Binding Affinity

The present clay-binding peptides exhibit a strong affinity for clay. The affinity of the peptide for the clay material can be expressed in terms of the dissociation constant $K_d$. $K_d$ (expressed as molar concentration) corresponds to the concentration of peptide at which the binding site on the target is half occupied, i.e., when the concentration of target with peptide bound (bound target material) equals the concentration of target with no peptide bound. The smaller the dissociation constant, the more tightly bound the peptide is; for example, a peptide with a nanomolar (nM) dissociation constant binds more tightly than a peptide with a micromolar (μM) dissociation constant. In one embodiment, the present clay-binding peptides have a $K_d$ of $10^{-3}$ M or less, preferably $10^{-4}$ M or less, more preferably $10^{-5}$ M or less, even more preferably $10^{-6}$ M or less, yet even more preferably $10^{-7}$ M or less, and most preferably $10^{-8}$ M or less.

Alternatively, one of skill in the art can also use an ELISA-based assay to calculate a relative affinity of the peptide for the target material (reported as an $MB_{50}$ value; see present Example 4 and co-owned U.S. Patent Application Publication 2005/022683, herein incorporated by reference). As used herein, the term "$MB_{50}$" refers to the concentration of the binding peptide that gives a signal that is 50% of the maximum signal obtained in an ELISA-based binding assay. The $MB_{50}$ provides an indication of the strength of the binding interaction or affinity of the components of the complex. The lower the value of $MB_{50}$, the stronger the interaction of the peptide with its corresponding substrate. In one embodiment, the $MB_{50}$ value (reported in terms of molar concentration) for the clay-binding peptide is $10^{-5}$ M or less, preferably $10^{-6}$ M or less, more preferably $10^{-7}$ M or less, and most preferably $10^{-8}$ M or less.

Peptide Binding to Non-exfoliated Clay

If the methods described above are applied to non-exfoliated clay, the clay-binding peptides identified will bind selectively to both the face and the edges of the clay platelets. The methods described above may also be used to identify clay-binding peptide domains that bind selectively to the face of clay platelets. In this embodiment, the sample used in the biopanning process is a totally exfoliated clay.

Clays are layered silicoaluminate materials in which the layers are anionic and held together by cationic metal ions between the layers. The layers may be "exfoliated" into individual layers by substitution of the metal ions with organic cationic surfactants. To achieve intercalation of the surfactants, solvent, or peptides into the stacked layers, the mixture is subjected to energy through high-shear mixing or ultrasound. Suitable clays to provide compatibility to the peptides include chemically modified organophilic, cation-exchanged smectite type clays and synthetic clays having hydroxyl functional groups on the edges and/or elsewhere on the surfaces of the particles. The degree of exfoliation is dependent upon the amount of energy employed and the ratio and efficacy of the organic surfactants.

The methods described above may also be used to identify clay-binding peptide domains that bind selectively to the edges of clay platelets. In this embodiment, the method comprises the following steps: (a) using the biopanning process on totally exfoliated clays to identify clay-binding peptides that have been exposed only to clay faces; (b) applying those face-selective clay-binding peptides to non-exfoliated clays to cover the faces of the particles; and (c) using the biopanning process on the resulting face-protected clay particles to identify clay-binding peptides that are selective for the remaining edges.

Clay-binding peptide domains that bind selectively to the edges of clay platelets may also be identified by a method comprising the following steps: (a) applying the clay-binding peptides that bind to both the face and edges of clay platelets (identified by the process described above) to clay particles that have been totally exfoliated; (b) washing off those clay-binding peptides that do not bind to the exfoliated clay particles; and (c) identifying clay-binding peptides that were bound selectively to the remaining edges using the methods described above.

Active Domains

As noted above active domains are peptide portions of the clay binding peptide that convey various additional functionality to the peptide. Any sequence of amino acids may be used as an active domain, including, but not limited to those functioning as a linker, those having binding functionality, having catalytic functionality and those having antimicrobial functionality.

An antimicrobial active domain may be particularly desirable if the clay moiety part of the affinity complex was for instance part of a kitchen countertop surface. Such antimicrobial sequences are well known in the art. Any peptide based antimicrobial sequence could be used as an active domain in the above embodiment. As non-limiting examples Table 1 provides possible antimicrobial active domain sequences.

TABLE 1

Antimicrobial Active Domain Sequences

| Species of origin | SEQ ID NO. | Sequence |
|---|---|---|
| Artificial | 13 | PKGLKKLLKGLKKLLKL |
| Artificial | 14 | KGLKKLLKGLKKLLKL |
| Artificial | 15 | KGLKKLLKLLKKLLKL |
| Artificial | 16 | LKKLLKLLKKLLKL |
| Artificial | 17 | LKKLLKLLKKLL |
| Artificial | 18 | VAKKLAKLAKKLAKLAL |
| Artificial | 19 | FAKLLAKALKKLL |
| Artificial | 20 | KGLKKGLKLLKKLLKL |
| Artificial | 21 | KGLKKLLKLGKKLLKL |
| Artificial | 22 | KGLKKLGKLLKKLLKL |
| Artificial | 23 | KGLKKLLKLLKKGLKL |
| Artificial | 24 | KGLKKLLKLLKKLGKL |
| Artificial | 25 | FALALKALKKLKKALKKAL |
| Artificial | 26 | FAKKLAKLAKKLAKLAL |
| Artificial | 27 | FAKLLAKLAKKLL |
| Artificial | 28 | FAKKLAKLALKLAKL |
| Artificial | 29 | FAKKLAKKLL |
| Artificial | 30 | FAKLLAKLAKKVL |
| Artificial | 31 | KYKKALKKLAKLL |
| Artificial | 32 | FALLKALLKKAL |
| Artificial | 33 | KRLFKKLKFSLRKY |
| Artificial | 34 | KRLFKKLLFSLRKY |
| Artificial | 35 | LLLFLLKKRKKRKY |
| *H. cecropia* | 36 | KWKLFKKIEKVGQNIRDGIIKAGPAVAWGQAT QIAK |
| *Xenopus sp.* | 37 | GIGKFLHSAKKFGKAFVGEIMNS |
| *Xenopus sp.* | 38 | GIGKFLKKAKKFGKAFVKILKK |
| *Bos Taurus* | 39 | RLCRIVVIRVCR |
| *Bos sp.* | 40 | ILPWKWPWWPWRR |
| *H. sapiens* | 41 | DSHAKRHHGYKRKFHEKHHSHRGY |

Two sub-types of active domains, target binding domains and linking domains, have been given specific names in the discussion disclosed herein. A target binding domain is an active domain that specifically binds to a known target. Target binding sequences are known in the art and can be developed using known techniques as well as techniques described herein. Non-limiting examples of targets to which target binding domains will bind include, pigments, dyes, chemical functional groups, print media, body surfaces (hair, skin, nails, teeth etc.) and biological analytes (cells, receptors, proteins, nucleic acids, viral particles, prions, etc.) (see FIGS. 4, 5 and 6 panel D).

Linking Domains

A linking domain is an active domain that is specifically used to separate two domains or a domain from a terminal end. Any sequence of amino acids that does not contain a clay-binding site can be used as a linking domain. A linking domain can have activity beyond just separating two domains of a peptide. A linking domain may provide a specific structure to the separating portion of the peptide. Conversely, a linking domain may also be selected to provide flexibility to the separating portion of the peptide. Additionally the linking domain may be created to specifically change the rheology of the medium the peptide is immersed in. Also the linking domain may be constructed so that it can be cleaved by, or act as the binding site for, a cleaving molecule or enzyme, for the purpose of releasing a portion of the peptide and/or the clay from the complex.

Preferred peptide linker domains are composed of the amino acids proline, lysine, glycine, alanine, and serine, and mixtures thereof. In addition, the linker domain may contain a specific enzyme cleavage site, such as the protease Caspase 3 site, given by SEQ ID NO:176, which allows for the enzymatic removal of a portion of the peptide and/or the clay from the complex. The peptide linker may be from 1 to about 50 amino acids, preferably from 1 to about 20 amino acids in length. Examples of peptide linkers include, but are not limited to, SEQ ID NOs:176 to 179. These peptide linkers may be linked to the binding peptide sequence by any method know in the art. For example, the peptide reagent may be prepared using the standard peptide synthesis methods described below. In addition, the binding peptide and peptide linker domains may be combined using carbodiimide coupling agents (see for example, Hermanson, *Bioconjugate Techniques*, Academic Press, New York (1996)), diacid chlorides, diisocyanates and other difunctional coupling reagents that are reactive to terminal amine and/or carboxylic acid groups on the peptides. Alternatively, the entire peptide reagent may be prepared using the recombinant DNA and molecular cloning techniques described below. The linker may also be a combination of a peptide linker and an organic linker molecule (described below), which may be prepared using the methods described above. Examples of specific linker peptides are given in Table 2.

TABLE 2

Linker Peptides

| Species of origin | SEQ ID NO. | Sequence |
|---|---|---|
| Artificial | 176 | LESGDEVD |
| Artificial | 177 | TSTSKASTTT TSSKTTTTSS KTTTTTSKTS TTSSSST |
| Artificial | 178 | GQGGYGGLGS QGAGRGGLGG QG |
| Artificial | 179 | GPGGYGPGQQ |

Target Domains

Target domains disclosed herein are another type of active domain comprised within the clay binding peptide. Target domains will have binding affinity for various substance such as benefit agents (pigments, dyes, etc.), print media, biological analytes, body surfaces (hair, skin, nails, teeth, etc.), and the like.

Pigment binding domains are target domains that bind various pigments and colorants. Such pigments have application in the personal care as well as the printing industries. Similarly print media binding domains are target binding domains having specific affinity for various types of print media. Typically the print media will comprise cotton or cellulose targets or may be coated with a polymer such as nylon or clay giving rise to cotton, cellulose or polymer binding domains as part of the clay-binding peptide.

Target domains may be uni-functional having binding affinity for a single target species or multifunctional, having affinity for a variety of targets. For example it may be desirable to combine a pigment binding domain or a print medium binding domain or both into the peptide part of the clay-peptide complex disclosed herein. Such an embodiment that includes a print-medium binding domain may be particularly desirable if the complex already contains a benefit agent that is a colorant or dye. Pigment-binding peptides and print medium-binding peptides have been identified (See tables 3, 4, and 5, and O'Brien et al., supra, hereby incorporated by reference). The pigment-binding peptides typically comprise at least about 40 mole % of the amino acids: glycine, alanine, valine, leucine, isoleucine, methionine, proline, phenylalanine, and tryptophan Specifically, binding peptides were isolated that have a high affinity for the pigments carbon black, given as SEQ ID NOs: 42-45, CROMOPHTHAL® Yellow, given as SEQ ID NOs: 46-53, SUNFAST® Magenta, given as SEQ ID NOs: 55-57, and SUNFAST® Blue, given as SEQ ID NOs: 54, 58-66. The cellulose-binding peptides disclosed herein comprise at least about 14 mole % of the amino acids: serine, threonine and tyrosine. Binding peptides having a high binding affinity for cellulose (a major component of cotton) include SEQ ID NOs: 73-78. The polyester-binding peptides disclosed herein comprise at least about 20 mole % of the amino acids: phenylalanine, tryptophan, and tyrosine. Binding peptides having a high affinity for polyester (poly (ethylene terephthalate)) include SEQ ID NO: 79. Additionally, binding peptides were isolated that have a binding affinity for the following print media: cotton, given as SEQ ID NOs: 67 and 68, polyester/cotton, given as SEQ ID NOs: 67 and 69, and printing paper, given as SEQ ID NOs: 67, and 70-72.

TABLE 3

Pigment-Binding Peptides

| Pigment | Designated Name | Peptide Sequence | SEQ ID NO: |
|---|---|---|---|
| Carbon Black | CB-71 | MPPPLMQ | 42 |
| | CB-72 | FHENWPS | 43 |
| | CB-121 | RTAPTTPLLLSL | 44 |
| | CB-122 | WHLSWSPVPLPT | 45 |
| Cromophtal ® Yellow | CY-71 | PHARLVG | 46 |
| | CY-72 | NIPYHHP | 47 |
| | CY-73 | TTMPAIP | 48 |
| | CY-74 | HNLPPRS | 49 |
| | CY-121 | AHKTQMGVRQPA | 50 |
| | CY-122* | ADNVQMGVSHTP | 51 |
| | CY-123* | AHNAQMGVSHPP | 52 |

TABLE 3-continued

Pigment-Binding Peptides

| Pigment | Designated Name | Peptide Sequence | SEQ ID NO: |
|---|---|---|---|
| | CY-124* | ADYVGMGVSHRP | 53 |
| | CY-125 | SVSVGMKPSPRP | 54 |
| Sunfast ® Magenta | SM-71 | YPNTALV | 55 |
| | SM-72 | VATRIVS | 56 |
| | SM-121 | HSLKNSMLTVMA | 57 |
| Sunfast ® Blue | SB-71 | NYPTQAP | 58 |
| | SB-72 | KCCYSVG | 59 |
| | SB-121 | RHDLNTWLPPVK | 60 |
| | SB-122 | EISLPAKLPSAS | 61 |
| | SB-123 | SVSVGMKPSPRP | 54 |
| | SB-124** | SDYVGMRPSPRH | 62 |
| | SB-125** | SDYVGMRLSPSQ | 63 |
| | SB-126** | SVSVGIQPSPRP | 64 |
| | SB-127** | YVSVGIKPSPRP | 65 |
| | SB-128** | YVCEGIHPCPRP | 66 |

* These sequences are analogs of CY-121.
** These sequences are either analogs of SB-123 or are similar to the analogs of SB-123.

TABLE 4

Print Medium-Binding Peptides

| Print Medium | Designated Name | Peptide Sequence | SEQ ID NO: |
|---|---|---|---|
| Cotton fabric | COT-71* | SILPYPY | 67 |
| | COT-72 | STASYTR | 68 |
| Polyester/cotton fabric | P/C-71 | LPVRPWT | 69 |
| | P/C-72* | SILPYPY | 67 |
| Hammermill ® paper | HCP-71 | GNTPSRA | 70 |
| | HCP-72 | HAIYPRH | 71 |
| | HCP-73 | YQDSAKT | 72 |
| | HCP-74* | SILPYPY | 67 |

* These sequences are identical.

TABLE 5

Cellulose and Poly(ethylene terephthalate)-Binding Peptides

| Print Medium Ingredient | Designated Name | Peptide Sequence | SEQ ID NO: |
|---|---|---|---|
| Cellulose | CEL-71 | VPRVTSI | 73 |
| | CEL-72 | MANHNLS | 74 |
| | CEL-73 | FHENWPS | 75 |
| | CEL-121 | THKTSTQRLLAA | 76 |
| | CEL-122 | KCCYVNVGSVFS | 77 |
| | CEL-123 | AHMQFRTSLTPH | 78 |
| Poly(ethylene terephthalate) | PET-121 | GTSDHMIMPFFN | 79 |

Target domains that have binding affinity for body surfaces are particularly useful for the production of personal care compositions comprising colorants, and conditioners with specific binding affinity for the body surface. For example, it may be desirable to attach a clay-peptide complex disclosed herein to a body surface such as hair or skin. One method to achieve such a result is to incorporate a target binding domain into the peptide part disclosed herein that binds hair, skin or another body surface. Alternatively, a clay-binding peptide comprising a clay-binding domain and a body surface-binding domain may be used to deliver a clay, which serves as a benefit agent (e.g., a pigment or conditioner), to a body surface. Both hair and skin binding domains can be produced by the methods described here, in the co-pending, commonly owned U.S. Ser. No. 10/935,642 (U.S. Patent Application Publication No. 2005/0050656) hereby incorporated by reference and in co-pending, commonly owned U.S. Ser. No. 11/074,473 (U.S. Patent Application Publication No. 2005/0226839) also hereby incorporated by reference. Examples of hair and skin binding domains are shown in Table 6.

TABLE 6

Body Surface Binding Peptide Domains

| Body Surface | SEQ ID NO | Sequence |
|---|---|---|
| Skin | 80 | FTQSLPR |
| Skin | 81 | TPFHSPENAPGS |
| Skin | 82 | KQATFPPNPTAY |
| Skin | 83 | HGHMVSTSQLSI |
| Skin | 84 | LSPSRMK |
| Skin | 85 | LPIPRMK |
| Skin | 86 | HQRPYLT |
| Skin | 87 | FPPLLRL |
| Nail | 88 | ALPRIANTWSPS |
| Nail | 89 | YPSFSPTYRPAF |
| Hair | 90 | YPSFSPTYRPAF |
| Hair | 91 | ALPRIANTWSPS |
| Hair | 92 | LESTPKMK |
| Hair | 93 | SVSVGMKPSPRP |
| Hair | 94 | LDVESYKGTSMP |
| Hair | 95 | RVPNKTVTVDGA |
| Hair | 96 | DRHKSKYSSTKS |
| Hair | 97 | KNFPQQKEFPLS |
| Hair | 98 | QRNSPPAMSRRD |
| Hair | 99 | TRKPNMPHGQYL |
| Hair | 100 | KPPHLAKLPFTT |
| Hair | 101 | NKRPPTSHRIHA |
| Hair | 102 | NLPRYQPPCKPL |
| Hair | 103 | RPPWKKPIPPSE |
| Hair | 104 | RQRPKDHFFSRP |
| Hair | 105 | SVPNK(T or P)VTVDG(E or A) |
| Hair | 106 | TTKWRHRAPVSP |
| Hair | 107 | WLGKNRIKPRAS |
| Hair | 108 | SNFKTPLPLTQS |
| Hair | 109 | KELQTRNVVQRE |

TABLE 6-continued

Body Surface Binding Peptide Domains

| Body Surface | SEQ ID NO | Sequence |
|---|---|---|
| Hair | 110 | GMPAMHWIHPFA |
| Hair | 111 | TPTANQFTQSVP |
| Hair | 112 | AAGLSQKHERNR |
| Hair | 113 | ETVHQTPLSDRP |
| Hair | 114 | LPALHIQRHPRM |
| Hair | 115 | QPSHSQSHNLRS |
| Hair | 116 | RGSQKSKPPRPP |
| Hair | 117 | THTQKTPLLYYH |
| Hair | 118 | TKGSSQAILKST |
| Hair | 119 | DLHTVYH |
| Hair | 120 | HIKPPTR |
| Hair | 121 | HPVWPAI |
| Hair | 122 | MPLYYLQ |
| Hair | 123 | HLTVPWRGGGSAVPFYSHSQITLPNH |
| Hair | 124 | GPHDTSSGGVRPNLHHTSKKEKRENRKVPFYSHSVT SRGNV |
| Hair | 125 | KHPTYRQ |
| Hair | 126 | HPMSAPR |
| Hair | 127 | MPKYYLQ |
| Hair | 128 | MHAHSIA |
| Hair | 129 | TAATTSP |
| Hair | 130 | LGIPQNL |
| Hair | 131 | AKPISQHLQRGS |
| Hair | 132 | APPTPAAASATT |
| Hair | 133 | DPTEGARRTIMT |
| Hair | 134 | EQISGSLVAAPW |
| Hair | 135 | LDTSFPPVPFHA |
| Hair | 136 | LPRIANTWSPS |
| Hair | 137 | RTNAADHPAAVT |
| Hair | 138 | SLNWVTIPGPKI |
| Hair | 139 | TDMQAPTKSYSN |
| Hair | 140 | TIMTKSPSLSCG |
| Hair | 141 | TPALDGLRQPLR |
| Hair | 142 | TYPASRLPLLAP |
| Hair | 143 | AKTHKHPAPSYS |
| Hair | 144 | TDPTPFSISPER |
| Hair | 145 | CAAGCCTCAGCGACCGAATA |
| Hair | 146 | WHDKPQNSSKST |
| Hair | 147 | NEVPARNAPWLV |
| Hair | 148 | NSPGYQADSVAIG |
| Hair | 149 | TQDSAQKSPSPL |
| Hair | 150 | TPPELLHGDPRS |
| Hair | 151 | TPPTNVLMLATK |
| Hair | 152 | NTSQLST |
| Hair | 153 | NTPKENW |
| Hair | 154 | NTPASNR |
| Hair | 155 | PRGMLST |
| Hair | 156 | PPTYLST |
| Hair | 157 | TIPTHRQHDYRS |
| Hair | 158 | TPPTHRL |
| Hair | 159 | LPTMSTP |
| Hair | 160 | LGTNSTP |
| Hair | 161 | TPLTGSTNLLSS |
| Hair | 162 | TPLTKET |
| Hair | 163 | QQSHNPP |
| Hair | 164 | TQPHNPP |
| Hair | 165 | STNLLRTSTVHP |
| Hair | 166 | HTQPSYSSTNLF |
| Hair | 167 | SLLSSHA |
| Hair | 168 | QQSSISLSSHAV |
| Hair | 169 | NASPSSL |
| Hair | 170 | HSPSSLR |
| Hair | 171 | K(H, R or N)SHHTH |
| Hair | 172 | E(H, R, or N)SHHTH |
| Hair | 173 | LESTSLL |
| Hair | 174 | TPLTKET |
| Hair | 175 | KQSHNPP |
| Hair | 195 | STLHKYKSQDPTPHH |
| Hair | 196 | HDHKNQKETHQRHAA |
| Hair | 197 | HNHMQERYTDPQHSPSVNGL |
| Hair | 198 | TAEIDSSKNPNPHPQRSWTN |

Table 7 presents amino acid sequences displaying high affinity binding to poly(methyl methacrylate) (PMMA) that will find utility as described below.

TABLE 7

Amino Acid Sequences of High Affinity PMMA-Binding Peptides

| Clone ID | Amino Acid Sequence | SEQ ID NO: |
|---|---|---|
| A09 | IPWWNIRAPLNA | 1 |
| D09 | TAVMNVVNNQLS | 2 |
| A03 | VPWWAPSKLSMQ | 3 |
| A06 | MVMAPHTPRARS | 4 |
| B04 | TYPNWAHLLSHY | 5 |
| B09 | TPWWRIT | 6 |
| B01 | DLTLPFH | 7 |
| PB411 | GTSIPAM | 8 |
| P307 | HHKHVVA | 9 |
| P410 | HHHKHFM | 10 |
| P202 | HHHRHQG | 11 |
| PNM407 | HHWHAPR | 12 |

Using similar methods, target-binding domains having an affinity for cellulosic materials, lignin materials, and ligno-cellulosic materials may be identified. Suitable cellulosic materials, lignin materials, and ligno-cellulosic materials include, but are not limited to, wood pulp fibers; non-woody paper-making fibers from cotton; straws and grasses, including rice and esparto; canes and reeds, including bagasse; bamboos; stalks with bast fibers, including jute, flax, kenaf, cannabis, linen and ramie; and leaf fibers, including abaca and sisal; paper or polymer-coated paper and recycled paper. The cellulosic materials may be obtained from one or more soft-wood or hardwood wood sources, including pines, spruces, firs, oaks, maples, eucalyptuses, poplars, beeches, and aspens. The cellulosic material may be in the form of sawdust, wood chips, or wood flour.

Target domains may also be identified using the methods described above for polymers such as poly(methyl methacrylate) (see Table 7), other acrylates and urethanes for use in automotive finishes or other paint products; natural or synthetic rubbers for use in rubber products; silicone materials for use in sealant products; and other polymers such as nylons (see Table 8), polyesters (see Table 5), polycarbonates, polyolefins, polyhydroxyalkanoates, and fluoropolymers (see Table 9). For additional examples of target domains, see Grinstaff et al. (U.S. Patent Application Publication No. 2003/0185870). Additionally, target domains may be identified for benefit agents used in personal care including, but not limited to, chelating agents, coloring agents, dispersants, emollients, emulsifiers, fragrances, humectants, opacifying agents, preservatives, skin conditioner, and thickeners for use in personal care products.

TABLE 8

Amino Acid Sequences of High Affinity Nylon-Binding Peptides

| Amino Acid Sequence | SEQ ID NO: |
|---|---|
| KTPPTRP | 180 |
| VINPNLD | 181 |
| KVWIVST | 182 |
| AEPVAML | 183 |
| AELVAML | 184 |
| HSLRLDW | 185 |

TABLE 9

Amino Acid Sequences of High Affinity Poly(tetrafluoroethylene)-Binding Peptides

| Amino Acid Sequence | SEQ ID NO: |
|---|---|
| ESSYSWSPARLS | 186 |
| GPLKLLHAWWQP | 187 |
| NALTRPV | 188 |
| SAPSSKN | 189 |
| SVSVGMKPSPRP | 190 |
| SYYSLPPIFHIP | 191 |
| TFTPYSITHALL | 192 |
| TMGFTAPRFPHY | 193 |
| TNPFPPPPSSPA | 194 |

Production of Clay-Binding Peptides

The clay-binding peptides disclosed herein may be prepared using standard peptide synthesis methods, which are well known in the art (see for example Stewart et al., *Solid Phase Peptide Synthesis*, Pierce Chemical Co., Rockford, Ill., 1984; Bodanszky, *Principles of Peptide Synthesis*, Springer-Verlag, New York, 1984; and Pennington et al., *Peptide Synthesis Protocols*, Humana Press, Totowa, N.J., 1994). Additionally, many companies offer custom peptide synthesis services.

Alternatively, the clay-binding peptides disclosed herein may be prepared using recombinant DNA and molecular cloning techniques. Genes encoding the clay-binding peptides may be produced in heterologous host cells, particularly in the cells of microbial hosts, as described by Huang et al. (U.S. Patent Application Publication No. 2005/0050656) and O'Brien et al., supra.

Preferred heterologous host cells for expression of the binding peptides disclosed herein are microbial hosts that can be found broadly within the fungal or bacterial families and which grow over a wide range of temperature, pH values, and solvent tolerances. Because transcription, translation, and the protein biosynthetic apparatus are the same irrespective of the cellular feedstock, functional genes are expressed irrespective of carbon feedstock used to generate cellular biomass. Examples of host strains include, but are not limited to, fungal or yeast species such as *Aspergillus, Trichoderma, Saccharomyces, Pichia, Candida, Hansenula*, or bacterial species such as *Salmonella, Bacillus, Acinetobacter, Rhodococcus, Streptomyces, Escherichia, Pseudomonas, Methylomonas, Methy-*

*lobacter, Alcaligenes, Synechocystis, Anabaena, Thiobacillus, Methanobacterium* and *Klebsiella.*

A variety of expression systems can be used to produce the peptides disclosed herein. Such vectors include, but are not limited to, chromosomal, episomal and virus-derived vectors, e.g., vectors derived from bacterial plasmids, from bacteriophage, from transposons, from insertion elements, from yeast episoms, from viruses such as baculoviruses, retroviruses and vectors derived from combinations thereof such as those derived from plasmid and bacteriophage genetic elements, such as cosmids and phagemids. The expression system constructs may contain regulatory regions that regulate as well as engender expression. In general, any system or vector suitable to maintain, propagate or express polynucleotide or polypeptide in a host cell may be used for expression in this regard. Microbial expression systems and expression vectors contain regulatory sequences that direct high level expression of foreign proteins relative to the growth of the host cell. Regulatory sequences are well known to those skilled in the art and examples include, but are not limited to, those which cause the expression of a gene to be turned on or off in response to a chemical or physical stimulus, including the presence of regulatory elements in the vector, for example, enhancer sequences. Any of these can be used to construct chimeric genes for production of the any of the binding peptides disclosed herein. These chimeric genes can then be introduced into appropriate microorganisms via transformation to provide high level expression of the peptides.

Vectors or cassettes useful for the transformation of suitable host cells are well known in the art. Typically the vector or cassette contains sequences directing transcription and translation of the relevant gene, one or more selectable markers, and sequences allowing autonomous replication or chromosomal integration. Suitable vectors comprise a region 5' of the gene, which harbors transcriptional initiation controls and a region 3' of the DNA fragment which controls transcriptional termination. It is most preferred when both control regions are derived from genes homologous to the transformed host cell, although it is to be understood that such control regions need not be derived from the genes native to the specific species chosen as a production host. Selectable marker genes provide a phenotypic trait for selection of the transformed host cells such as tetracycline or ampicillin resistance in *E. coli.*

Initiation control regions or promoters which are useful to drive expression of the chimeric gene in the desired host cell are numerous and familiar to those skilled in the art. Virtually any promoter capable of driving the gene is suitable for producing the binding peptides disclosed herein including, but not limited to: CYC1, HIS3, GAL1, GAL10, ADH1, PGK, PHO5, GAPDH, ADC1, TRP1, URA3, LEU2, ENO, TPI (useful for expression in *Saccharomyces*); AOX1 (useful for expression in *Pichia*); and lac, ara, tet, trp, $IP_L$, $IP_R$, T7, tac, and trc (useful for expression in *Escherichia coli*) as well as the amy, apr, npr promoters and various phage promoters useful for expression in *Bacillus.*

Termination control regions may also be derived from various genes native to the preferred hosts. Optionally, a termination site may be unnecessary, however, it is most preferred if included.

The vector containing the appropriate DNA sequence as described supra, as well as an appropriate promoter or control sequence, may be employed to transform an appropriate host to permit the host to express the peptides disclosed herein. Cell-free translation systems can also be employed to produce such peptides using RNAs derived from the DNA constructs disclosed herein. Optionally, it may be desired to produce the instant gene product as a secretion product of the transformed host. Secretion of desired proteins into the growth media has the advantages of simplified and less costly purification procedures. It is well known in the art that secretion signal sequences are often useful in facilitating the active transport of expressible proteins across cell membranes. The creation of a transformed host capable of secretion may be accomplished by the incorporation of a DNA sequence that codes for a secretion signal which is functional in the production host. Methods for choosing appropriate signal sequences are well known in the art (see for example EP 546049 and WO 9324631). The secretion signal DNA or facilitator may be located between the expression-controlling DNA and the instant gene or gene fragment, and in the same reading frame with the latter.

Benefit Agents

Benefit agents are any material or substance that may be complexed with the clay-binding peptide in a manner so as to deliver a benefit at the point where the clay-binding peptide is attached. In the most general sense the benefit agent will be a component of an affinity complex comprising the clay binding peptide. Any complex, compound or element may be used with the materials described herein as a benefit agent. If a user disclosed herein desires to have the features of a benefit agent combined with clay then an affinity complex may be constructed to include the benefit agent in the formation with clay and a clay-binding peptide. A benefit agent may be selected for the purpose of adding the physical, chemical and/or biological properties of said agent to the clay-peptide complex disclosed herein. The result of this construct will be said benefit agent closely associated with clay and the activity of said benefit agent will be included within the affinity complex.

The affinity complex embodiment disclosed herein is composed of at least one member of each component but may also have multiple copies of identical or different members of one, two or all three components. Benefit agents can be used singularly or in a plurality. In some embodiments a plurality of peptide binding domains or a plurality of clay particles or a plurality of both components may be added to a single benefit agent or a number of benefit agents. For some small benefit agents, for non-limited example, those composed of an element, as many as 10,000 benefit agents could be added to a single clay-complex. For some large benefit agents, for non-limiting example, a dye embedded in a plastic bead as many as 100 clay complexes might be attached to a single benefit agent.

Benefit agents may be inorganic or organic in nature, this includes being polymer or peptide based. The clay itself may be a benefit agent which is delivered to another surface, such as a body surface. Some preferred embodiments include benefit agents that are pigments, pharmaceuticals, markers, conditioners, colorants, and fragrances.

Pharmaceuticals

A pharmaceutical generally means a substance dosed to an organism or thing to treat or prevent a disease or condition. A pharmaceutical benefit agent includes, in a non-limiting sense, the topical, internal or intracellular administration of a compound to an organism as a treatment or a prophylactic. A non-limiting example of this embodiment disclosed herein would be the attachment of an anti-acne medication to formulation disclosed herein designed to be a skin conditioner. A pharmaceutical benefit agent also includes a treatment to surface or item to prevent an infectious germ from being transmitted after contacting said surface or item. The addition of an antimicrobial compound to a construction disclosed herein to be used on countertops would be a non-limiting example of this embodiment. Suitable pharmaceuticals are well known in the art. An extensive list is given by Kabonov et al. in U.S. Pat. No. 6,696,089, which is incorporated herein by reference (in particular, columns 16 to 18). Examples include, but are not limited to, antibacterial agents, antiviral agents, antifungal agents, anti-cancer agents, vaccines, radiolabels, anti-inflammatories, anti-glaucomic agents, local anesthetics, anti-neoplastic agents, antibodies, hormones, and the like.

Markers

Markers as used and defined herein refer to a class of benefit agents that provide aid in detecting the presence of the clay-peptide complex to which they are, or were, attached. The marker benefit agent might be a dye, fluorescent label, radioactive element or some other signal. Radioactive $P^{32}$ is a non-limiting example of this type of marker benefit agent. Also the marker benefit agent might also be a substance that reacts with a dye, fluorescent label or other signal. Biotin used in connection with a labeled-streptavidin compound is a non-limiting example of this type of marker benefit agent. Additionally a marker benefit agent might also provide, or help to provide aid to detect, the presence or lack of presence of another specific chemical, compound, element or complex. By way of non-limiting example, the marker benefit agent might be a compound that is metabolized by a specific enzyme to produce a metabolite that reacts with a fluorescently labeled phosphine. The Staudinger ligation is a non-limiting example of this type of marker benefit agent.

Conditioners

Conditioner benefits agents as referred to in discussion disclosed herein generally mean benefit agents that provide an improvement to the appearance, texture or quality of the substance they are designed to condition. Conditioner benefit agents may be used with the materials described herein to condition any substance including but not limited to hair, skin, lips, leather, and upholstery. In the preferred embodiment described herein are used in combination with a benefit agent that provides a conditioning effect to hair and skin. In the most preferred embodiment said hair and skin are human hair and human skin.

Hair conditioning agents as herein defined are agents that improve the appearance, texture, and sheen of hair as well as increasing hair body or suppleness. In the peptide-based hair conditioners disclosed herein, any known hair conditioning agent may be used. Hair conditioning agents are well known in the art, see for example Green et al. (WO 0107009), incorporated herein by reference, and are available commercially from various sources. Suitable examples of hair conditioning agents include, but are not limited to, cationic polymers, such as cationized guar gum, diallyly quaternary ammonium salt/acrylamide copolymers, quaternized polyvinylpyrrolidone and derivatives thereof, and various polyquaternium-compounds; cationic surfactants, such as stearalkonium chloride, centrimonium chloride, and Sapamin hydrochloride; fatty alcohols, such as behenyl alcohol; fatty amines, such as stearyl amine; waxes; esters; nonionic polymers, such as polyvinylpyrrolidone, polyvinyl alcohol, and polyethylene glycol; silicones; siloxanes, such as decamethylcyclopentasiloxane; polymer emulsions, such as amodimethicone; and volumizing agents, such as nanoparticles (e.g., silica nanoparticles and polymer nanoparticles). The preferred hair conditioning agents disclosed herein contain amine or hydroxyl functional groups to facilitate coupling to the hair-binding peptides. Examples of preferred conditioning agents are octylamine (CAS No. 111-86-4), stearyl amine (CAS No. 124-30-1), behenyl alcohol (CAS No. 661-19-8, Cognis Corp., Cincinnati, Ohio), vinyl group terminated siloxanes, vinyl group terminated silicone (CAS No. 68083-19-2), vinyl group terminated methyl vinyl siloxanes, vinyl group terminated methyl vinyl silicone (CAS No. 68951-99-5), hydroxyl terminated siloxanes, hydroxyl terminated silicone (CAS No. 80801-30-5), amino-modified silicone derivatives, [(aminoethyl)amino]propyl hydroxyl dimethyl siloxanes, [(aminoethyl)amino]propyl hydroxyl dimethyl silicones, and alpha-tridecyl-omega-hydroxy-poly(oxy-1,2-ethanediyl) (CAS No. 24938-91-8).

Skin conditioning agents as herein defined include, but are not limited to astringents, which tighten skin; exfoliants, which remove dead skin cells; emollients, which help maintain a smooth, soft, pliable appearance; humectants, which increase the water content of the top layer of skin; occlusives, which retard evaporation of water from the skin's surface; and miscellaneous compounds that enhance the appearance of dry or damaged skin or reduce flaking and restore suppleness. In the peptide-based skin conditioners disclosed herein, any known skin conditioning agent may be used. Skin conditioning agents are well known in the art, see for example Green et al. supra, and are available commercially from various sources. Suitable examples of skin conditioning agents include, but are not limited to, alpha-hydroxy acids, beta-hydroxy acids, polyols, hyaluronic acid, D,L-panthenol, polysalicylates, vitamin A palmitate, vitamin E acetate, glycerin, sorbitol, silicones, silicone derivatives, lanolin, natural oils and triglyceride esters. The preferred skin conditioning agents disclosed herein are polysalicylates, propylene glycol (CAS No. 57-55-6, Dow Chemical, Midland, Mich.), glycerin (CAS No. 56-81-5, Proctor & Gamble Co., Cincinnati, Ohio), glycolic acid (CAS No. 79-14-1, DuPont Co., Wilmington, Del.), lactic acid (CAS No. 50-21-5, Alfa Aesar, Ward Hill, Mass.), malic acid (CAS No. 617-48-1, Alfa Aesar), citric acid (CAS No. 77-92-9, Alfa Aesar), tartaric acid (CAS NO. 133-37-9, Alfa Aesar), glucaric acid (CAS No. 87-73-0), galactaric acid (CAS No. 526-99-8), 3-hydroxyvaleric acid (CAS No. 10237-77-1), salicylic acid (CAS No. 69-72-7, Alfa Aesar), and 1,3 propanediol (CAS No. 504-63-2, DuPont Co., Wilmington, Del.). Polysalicylates may be prepared by the method described by White et al. in U.S. Pat. No. 4,855,483, incorporated herein by reference. Glucaric acid may be synthesized using the method described by Merbouh et al. (*Carbohydr. Res.* 336:75-78 (2001). The 3-hydroxyvaleric acid may be prepared as described by Bramucci in WO 02012530. Additionally, the clay may serve as a skin conditioning agent.

The clay may also serve as a conditioning agent for hair or skin. In this embodiment, the clay is attached to the body surface using a clay-binding peptide reagent comprising a clay-binding domain and a body surface-binding domain. The body surface-binding domain binds to the body surface while the clay-binding domain binds to the clay, thereby attaching the clay conditioning agent to the body surface. The clay can serve as the conditioning agent directly or can serve to carry bound conditioning agents.

Colorants

The term colorant generally refers to a coloring agent. Colorants may be chemically organic or inorganic and may include pigments, lakes, or dyes. The peptide-based colorants disclosed herein may be prepared by covalently attaching a specific clay-binding peptide to a coloring agent, either directly or via a linker, using any of the coupling methods known in the art (see for example, U.S. Patent Application Publication No. 2005/0226839).

Pigments are a particularly suitable benefit agent. Pigments generally means an insoluble colorant. A wide variety of organic and inorganic pigments alone or in combination may be used in the materials or methods described herein. Examples of organic pigments which are particularly useful for printing applications include, but are not limited to Cyan, Yellow, Red, Blue, Orange, Magenta, Black, Green, Violet, Light Cyan, and Light Magenta. Preferred organic pigments are carbon black, such as Carbon Black FW18, and colored pigments such as CROMOPHTHAL® Yellow 131AK (Ciba Specialty Chemicals), SUNFAST® Magenta 122 (Sun Chemical) and SUNFAST® Blue 15:3 (Sun Chemical). Examples of inorganic pigments which are particularly useful for printing applications include, but are not limited to finely divided metals, such as copper, iron, aluminum, and alloys thereof; and metal oxides, such as silica, alumina, and titania. Additional examples of suitable pigments are given by Ma et al. in U.S. Pat. No. 5,085,698, incorporated herein by reference.

The preferred coloring agents for use in the skin based applications disclosed herein include but are not limited to the following dyes: eosin derivatives such as D&C Red No. 21 and halogenated fluorescein derivatives such as D&C Red No. 27, D&C Red Orange No. 5 in combination with D&C Red No. 21 and D&C Orange No. 10, and the pigments: titanium dioxide, zinc oxide, D&C Red No. 36, D&C Red No. 30, D&C Orange No. 17, Green 3 Lake, Ext. Yellow 7 Lake, Orange 4 Lake, and Red 28 Lake; the calcium lakes of D&C Red Nos. 7, 11, 31 and 34, the barium lake of D&C Red Nos. 12, the strontium lake D&C Red No. 13, the aluminum lakes of FD&C Yellow No. 5, of FD&C Yellow No. 6, of FD&C No. 40, of D&C Red Nos. 21, 22, 27, and 28, of FD&C Blue No. 1, of D&C Orange No. 5, of D&C Yellow No. 10, the zirconium lake of D&C Red No. 33; iron oxides, calcium carbonate, aluminum hydroxide, calcium sulfate, kaolin, ferric ammonium ferrocyanide, magnesium carbonate, carmine, barium sulfate, mica, bismuth oxychloride, zinc stearate, manganese violet, chromium oxide, ultramarine blue, and carbon black.

The preferred coloring agents for use with the methods or materials described herein in the nail based applications include but are not limited to D&C Red Nos. 8, 10, 30 and 36, the barium lakes of D&C Red Nos. 6, 9 and 12, the calcium lakes of D&C Red Nos. 7, 11, 31 and 34, the strontium lake of D&C Red No. 30 and D&C Orange No. 17 and D&C Blue No. 6.

Suitable hair coloring agents for use with the methods or materials described herein include, but are not limited to dyes, such as 4-hydroxypropylamino-3-nitrophenol, 4-amino-3-nitrophenol, 2-amino-6-chloro-4-nitrophenol, 2-nitro-paraphenylenediamine, N,N-hydroxyethyl-2-nitro-phenylenediamine, 4-nitro-indole, Henna, HC Blue 1, HC Blue 2, HC Yellow 4, HC Red 3, HC Red 5, Disperse Violet 4, Disperse Black 9, HC Blue 7, HC Blue 12, HC Yellow 2, HC Yellow 6, HC Yellow 8, HC Yellow 12, HC Brown 2, D&C Yellow 1, D&C Yellow 3, D&C Blue 1, Disperse Blue 3, Disperse violet 1, eosin derivatives such as D&C Red No. 21 and halogenated fluorescein derivatives such as D&C Red No. 27, D&C Red Orange No. 5 in combination with D&C Red No. 21 and D&C Orange No. 10; and pigments, such as D&C Red No. 36, D&C Red No. 30, and D&C Orange No. 17, Green 3 Lake, Ext. Yellow 7 Lake, Orange 4 Lake, and Red 28 Lake; the calcium lakes of D&C Red Nos. 7, 11, 31 and 34, the barium lake of D&C Red No. 12, the strontium lake of D&C Red No. 13, the aluminum lakes of FD&C Yellow No. 5, of FD&C Yellow No. 6, of FD&C No. 40, of D&C Red Nos. 21, 22, 27, and 28, of FD&C Blue No. 1, of D&C Orange No. 5, of D&C Yellow No. 10, the zirconium lake of D&C Red No. 33; calcium carbonate, aluminum hydroxide, calcium sulfate, kaolin, ferric ammonium ferrocyanide, magnesium carbonate, carmine, barium sulfate, mica, bismuth oxychloride, zinc stearate, manganese violet, chromium oxide, titanium dioxide, iron oxides, zinc oxide, barium oxide, ultramarine blue, bismuth citrate, and carbon black particles.

The clay may also serve as a pigment because of its inherent color. Additionally, the clay may serve as a carrier for a dye, thus forming a lake pigment. For example, an assortment of colored clays is sold under the tradename Planocolors® by TNO (Delft, The Netherlands). In this embodiment, the clay pigment is attached to the body surface using a clay-binding peptide reagent comprising a clay-binding domain and a body surface-binding domain. The body surface-binding domain binds to the body surface while the clay-binding domain binds to the clay pigment, thereby attaching the colorant to the body surface.

Fragrances

A fragrance is a complex, compound or element that releases, a substance which may be perceived by the sense of olfaction or chemical detection in any organism, but preferably, in humans. The object sensed or detected may be a part of or the whole of the fragrance benefit agent. In the preferred embodiment the odor is perceived as desirable to humans. However, some uses may combine the methods or materials described herein with a fragrance benefit agent that is repellent to a class of organisms, including a class that contains or is humans. Any known fragrance or odor may be use as a benefit agent. It may be desirable to attach a fragrance benefit agent to the clay-peptide complex by a bond structure or linking molecule that allows the benefit agent to be released, in part or in whole, so that it may be perceived by a sensing organ or chemical detector.

Numerous fragrances, both natural and synthetic, are well known in the art. For example, Secondini (*Handbook of Perfumes and Flavors*, Chemical Publishing Co., Inc., New York, 1990), incorporated herein by reference, describes many of the natural and synthetic fragrances used in cosmetics. Suitable natural fragrances include, but are not limited, to jasmines, narcissus, rose, violet, lavender, mint, spice, vanilla, anise, amber, orange, pine, lemon, wintergreen, rosemary, basil, and spruce. Suitable synthetic fragrances include, but are no limited to, acetaldehyde, C7 to C16 alcohols, benzyl acetate, butyric acid, citric acid, isobutyl phenyl acetate, linalyl butyrate, malic acid, menthol, phenyl ethyl cinnamate, phenyl propyl formate, tannic acid, terpineol, vanillin, amyl salicylate, benzaldehyde, diphenyl ketone, indole, and the like.

Organic Linker Molecules

Figure 3:
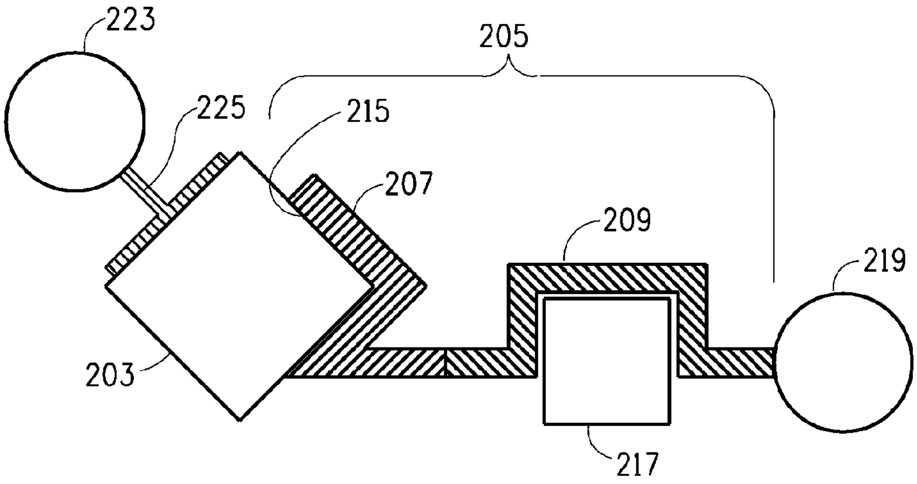
FIG. 3 depicts some embodiments disclosed herein as an affinity complex, optionally bound to a benefit agent at two different positions and/or a target molecule. Also depicted is the optional inclusion of a linker molecule and/or an active domain.

Organic linker molecules may optionally be used with some embodiments disclosed herein for the purpose of attaching the benefit agent to the clay-peptide complex (see FIG. 3, reference number 225). Additionally, the organic linker may be used instead of a peptide linker domain to couple the clay-binding domain to another active domain. Multiple copies of the clay-binding domain and the other active domain may be coupled through the linker molecule to enhance the strength of the interaction with the substrates. Any molecule, compound or complex that will attach the benefit agent to the complex or attach the two binding domains together can be used as a linking molecule provided the linking molecule does not contain clay or a clay-binding domain. The benefit agent may be attached to the complex to either the clay moiety or the peptide portion or in the case of a plurality of benefit agent possibly to both. The linking molecules may be designed to bond the benefit agent in a stable form or in the alternative they may be designed to break and release the benefit agent from the complex in a given circumstance. Such circumstances could be, for non-limiting example, a range of pH, a range of temperatures, a range of pressure, while immersed in a certain media, the presence of a particular element, molecule or compound at a certain range of concentration, after a given passage of time, or at a certain average rate for a population of linker molecules.

Specifically the organic linker may be any of a variety of organic molecules, such as alkyl chains, phenyl compounds, ethylene glycol, amides, esters and the like. Preferred linkers are hydrophilic and have a chain length from 1 to about 100 atoms, more preferably, from 2 to about 30 atoms. Examples of preferred linkers include, but are not limited to, ethanol amine, ethylene glycol, polyethylene with a chain length of 6 carbon atoms, polyethylene glycol with 3 to 6 repeating units, phenoxyethanol, propanolamide, butylene glycol, butyleneglycolamide, propyl phenyl, and ethyl, propyl, hexyl, steryl, cetyl, and palmitoyl alkyl chains. The linker may be covalently attached to the peptide and the benefit agent or the two binding domains using any of the coupling chemistries described above. In order to facilitate incorporation of the linker, a bifunctional cross-linking agent that contains a linker and reactive groups at both ends for coupling to the peptide and the benefit agent may be used. Suitable bifunctional cross-linking agents are well known in the art and include, but are not limited to diamines, such as 1,6-diaminohexane; dialdehydes, such as glutaraldehyde; bis N-hydroxysuccinimide esters, such as ethylene glycol-bis(succinic acid N-hydroxysuccinimide ester), disuccinimidyl glutarate, disuccinimidyl suberate, and ethylene glycol-bis(succinimidylsuccinate); diisocyantes, such as hexamethylenediisocyanate; bis oxiranes, such as 1,4 butanediyl diglycidyl ether; dicarboxylic acids, such as succinyldisalicylate; and the like. Heterobifunctional cross-linking agents, which contain a different reactive group at each end, may also be used.

Applications of Clay-Binding Peptides

It will be appreciated by the skilled person that clay-binding peptides comprising active and target domains having specific functionality may be used in a multiplicity of formats including as delivery means for delivering benefits agents, in assays for diagnostic applications as well as in materials applications for coating substrate surfaces, such as printing on paper. Additionally, aqueous slurries of fine particle size clays are used in a diverse range of end-use products. In many cases, the end-use performance is governed by the fineness of the particle size distribution. In turn, the maximum fineness of the particle size distribution is primarily determined by the efficiency of the dispersants used during the production process. The compositions described herein may be excellent dispersing agents and compatibilizers as a result of the high degree of stabilization achieved through biological selection of stabilizing affinity reagents. This may be utilized to produce more effective dispersant systems which provide added value, higher solids and finer particle size clay slurry products.

The following description of the figures presents a limited number of additional examples of the methods disclosed herein, but is by no means inclusive of all possible applications and formats.

Referring to FIG. 1 panel A, there is shown a surface 1 comprising, in whole or in part, a clay moiety 3. At least some of the clay moieties 3 are exposed in various orientations on the exterior of the surface. The clay-binding peptide 5 comprises at least one, but not limited to one, clay-binding domain 7. The clay-binding domain 7 further comprises at least one, but not limited to one, clay-binding site 15. Clay-binding peptides 5 will bind specifically to clay moieties 3, this binding will occur at the clay-binding site 15 of the clay domain 7 within the clay-binding peptide 5.

FIG. 1 panel B depicts another embodiment disclosed herein. In this embodiment, a clay-binding peptide 5 also binds to a surface 1 comprising, in whole or in part, clay moieties 3. A benefit agent 19 is coupled to the clay-binding peptide 5 covalently, ionically or otherwise as described elsewhere herein. Although bound to the clay-binding peptide 5, the benefit agent 19 generally retains the biological, chemical and physical properties that it exhibited before being coupled to the clay-binding peptide 5. The combination of the clay particle 3, the clay-binding peptide 5, and the benefit agent 19 forms an affinity complex. The proximity of the benefit agent 19 to the surface 1 after binding allows the benefit agent 19 to be active at that location, and provides the chemical property of the benefit agent 19 on the clay-containing surface 1. Non-limiting examples of the benefit agents 19 are colorants such as dyes and pigments, conditioners, fragrances, pharmaceuticals and the like.

FIG. 1 panel C depicts still another embodiment disclosed herein. The clay-binding peptide 5 binds to a surface 1 comprising clay moieties 3 as above. Panel C, as in panels A and B, shows the clay-binding peptide 5 comprising at least one, but not limited to one, clay-binding domain 7 within its structure. The clay-binding domain 7 comprises at least one, but not limited to one, clay-binding site 15. The clay-binding peptide 5 of panel C further comprises at least one, but not limited to one, active domain 9 different from the clay-binding domain 7, yet within the same clay-binding peptide 5. By having an active domain 9 within the peptide 5 and the peptide 5 being bound to a clay-containing surface 1 this embodiment disclosed herein allows the property of the active domain 9 to be transmitted to the surface 1. One non-limiting example of an active domain as exemplified here is a domain having antimicrobial properties.

FIG. 1 panel D depicts still another embodiment disclosed herein. The clay-binding peptide 5 binds to a surface 1 comprising clay moieties 3 as described above. In this embodiment, the clay-binding peptide 5 comprises a specific target-binding domain 11 targeting other molecules other than clay. In this embodiment, the clay-binding peptide 1 acts as an intermediary to bring the target molecules close to the surface 1. This may be used to provide the chemical, biologic or physical function of target molecule 17 on the surface 1. However, this embodiment may also be employed to isolate the target molecule 17 from the surrounding media. Another use may be to sample the surrounding media for the presence of the target molecule 17. Non-limiting examples of the other target molecules 17 include benefit agents such as colorants (e.g., dyes and pigments) and conditioners as well as biological analytes, (cells, membrane fractions, viral particles, proteins, nucleic acids and the like), body surfaces, (hair, skin, nails, teeth and the like) as well as other organic and inorganic target complexes.

FIG. 1 panel E depicts still another embodiment disclosed herein. The clay-binding peptide 5 binds to a surface 1 comprising clay moieties 3 as above. Panel E depicts a clay-binding peptide 5 that contains a linker domain 13 that serves to connect the clay-binding peptide 5 to a benefit agent 19. The linker domain 13 is a domain that selected to physically separate the benefit agent 19 from the clay-binding domain(s) 7. Alternatively, although not depicted in the FIG. 1, a single linker domain or many linker domains may be provided to separate various domains within the clay-binding peptide. For instance, it may be advantageous to separate the clay-binding domain from an active domain, or to separate two or more active domains, a linker could be utilized to achieve this separation. The linker domain 13 may simply provide a steric benefit. Although in some uses of this embodiment the linker provides a specific structure or orientation between the clay-binding peptide 5 and the benefit agent 19 or to limit the conformation of the benefit agent-clay-binding peptide-clay affinity complex. In other uses of this embodiment the linker 13 provides a flexible region so that the benefit agent-clay-binding peptide-clay affinity complex can form a particular conformation or a variety of different conformations. Still, in other uses of this embodiment the chemical and physical nature of the linker 13 may be used to change the rheology of the environment surrounding the surface 1 to which the peptide 5 is bound. Non-limiting examples of linker domains 13 that would alter the rheology of the surrounding surface include hydrophobic, hydrophilic, or charged molecules. Additionally a linker domain 13 may be employed to release a benefit agent 19 from the clay-binding peptide 5 under various circumstances. Such circumstances may include for example, a certain range of pH, or a certain range of temperatures, or a certain range of pressures. Such circumstances may also include response to shock, response to the presence of a particular molecule, especially a peptide cleaving molecule, or the passage of time.

Figure 2A:
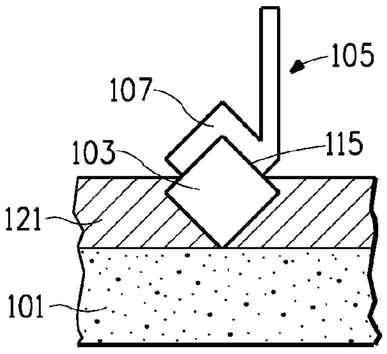
FIG. 2 is a set of panels A-C which depict some embodiments disclosed herein as they are bound to a clay coating containing, in whole or in part, clay particles, which is further bound to a surface.
Figure 2B:
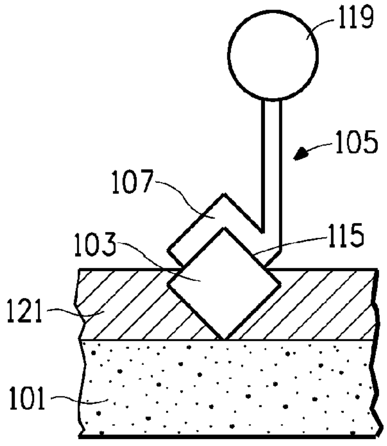
Figure 2C:
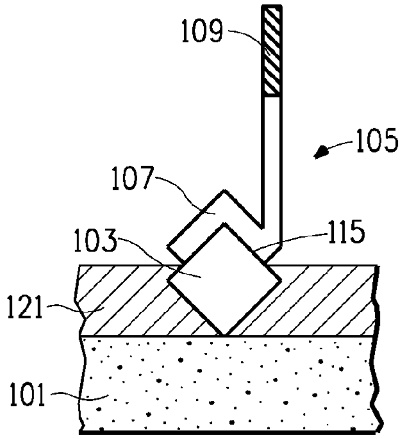

Referring to FIG. 2 panel A, a surface 101 is shown that could be comprised of any surface material. Non-limiting examples of such surfaces are metal, paper, glass, rubber and cloth. A coating 121 comprised of in whole or in part, clay moieties 103 have been applied to the surface 101 as shown. In this embodiment disclosed herein, a clay-binding peptide 105 is targeted to the coating. As in the above descriptions the clay-binding peptide 105 comprises, in whole or in part, at least one clay-binding domain 107, which itself comprises, in whole or in part, at least one clay-binding site 115. As described elsewhere herein the clay-binding site 115 binds specifically to clay moieties 103. In this embodiment the clay-binding site 115 binds to exposed portions of clay 103 in a clay coating 121 on attached to the surface 101. In this embodiment the clay-binding peptide 105 is useful to provide an additional coating to clay coating 103 already applied to the surface 101. Non-limiting examples of the uses for this embodiment include a sacrificial layer to protect the clay coating or in the case of multiple clay domains 107 and/or binding sites 115 to act as an adhesive between the clay coat 121 and other clay moieties 103 or surfaces 101.

Similar to Panel A, FIG. 2 Panel B depicts a clay-binding peptide 105 coupled to a clay coating 121 on a surface 101. The clay-binding peptide 105 depicted in panel B further comprises a benefit agent 119. In this embodiment disclosed herein, at least one, but not limited to one, benefit agent 119 is coupled to the clay-binding peptide 105 by a covalent, ionic or other interactive means. The clay-binding peptide-benefit agent affinity complex is in turn coupled to a clay moiety 103 within the clay coating 121 on the surface 101. As described elsewhere herein the benefit agent 119 has some activity or functionally that persists while it is bound to the clay-binding peptide 105 and the complex is bound to the clay coating 121. The active benefit agent 119 being brought to or near the coating 121 by the clay-binding peptide 105 conveys its activity to the coating modifies the coating or enhances the coating. In a similar embodiment, a plurality of different types of clay-binding peptides 105 may be used in combination so that the different benefit agents 119 corresponding to the different clay-binding peptides 105 may interact, or act in concert to produce a desirable result. A non-limiting example of a use for this embodiment is to deliver a pigment to a clay coating on paper for printing applications.

Similar to Panel A, FIG. 2 Panel C depicts a clay-binding peptide 105 bound to a clay coating 121 on a surface 101. The clay-binding peptide 105 comprises all of the features of the clay-binding peptide 105 depicted in Panel A, with the added feature that the peptide includes an active domain 109 separate from the clay-binding domain. This active domain 109, remains active as part of the clay-binding peptide 105, and further continues to be active when the clay-binding peptide 105 binds to clay moieties 103 within the clay coating 121. The active domain 109, by virtue of being part of the affinity complex containing the clay-binding peptide 105 and the clay coating 121, is active in the proximity of the coating 121. This allows the coating 121 to exhibit the activity of the active domain 109 contained in the clay-binding peptide 105 bound to the clay moieties 103 contained within the coating 121. Additionally, as in panel B, a benefit agent 119 may also be chemically attached to the functional domain containing clay-binding peptide 105 (not shown). As stated above, an additional embodiment would be the use of a plurality of different types of clay-binding peptides 105 to interact or act in concert to produce a desirable result.

Referring to FIG. 3, another embodiment disclosed herein is shown in which the clay is not bound to a larger surface. In this embodiment the clay exists as a clay moiety 203 which may be suspended in solution, such as cell growth media, air, water, oil, biological fluids, gels and the like. A clay-binding peptide 205 is depicted bound to the clay moiety 203. The clay-binding peptide 205 contains within its peptide structure at least one, but not limited to one clay-binding domain 207. The clay-binding domain 207 contains within its structure a clay-binding site 215. clay-binding domains 207 and clay-binding sites 215 bind clay moieties 203 specifically as described elsewhere herein. Binding of the clay-binding peptide 205 to the clay 203 occurs at the clay-binding site 215 with the clay-binding domain 207. The binding of clay moieties 203 to the clay-binding peptide 205 forms an affinity complex. A non-limiting example of this embodiment is the use of the clay-binding peptide as a dispersant to disperse clay particles in solution, as described above.

Other embodiments disclosed herein add additional elements to the affinity complex of clay moiety 203 and clay-binding peptide 205. One such embodiment, involves binding a benefit agent 219 to the clay-binding peptide 205. The benefit agent 219 may be coupled to the clay-binding peptide 205 by any known means, as described above. The function of benefit agents 219 is discussed in greater detail elsewhere herein.

Alternatively the benefit agent 223 may be attached to the clay moiety 203. In this format, the benefit agent 223 is attached to the clay moiety or bead 203 typically by chemical means or bonds 225. The bond may be part of the benefit agent 223 or may be an independent structure that is bound to the clay 203 for the purpose of binding the benefit agent 223. In the alternative, the bond structure 225 may be bound to the benefit agent 223 for the purpose of binding it to the clay 203. The binding structure 225 may be a permanent bond, but in some forms of the embodiment may be easily broken under certain conditions. In other forms of the embodiment, the bond 225 may allow the benefit agent 223 to be leached from the clay moiety or bead 203 under certain conditions. In still other forms of the embodiment, the bond 225 may allow the benefit agent 223 to be released over time at regular or specific time intervals. Alternatively, the bond 225, itself, may be in whole or in part be composed of clay. In this way, the clay moiety or bead 203 may be in whole or in part the binding structure 225. The benefit agent 223 may be partially or fully embedded with the clay moiety or bead 203.

In another embodiment described by FIG. 3, the clay-binding peptide 205 is bound the clay 203 as described above and the complex may optionally be bound to a benefit agent 219 and/or 223 by any method described elsewhere herein. The additional feature of this embodiment is at least one or a plurality of additional active peptide domains 209 within the clay-binding peptide 205. Any known peptide active domain 209 can be used in this embodiment. Alternatively, the active domain 209 may be a linker domain or may function as a target domain and bind a target 217. A non-limiting example of this embodiment is the attachment of clay particles to the surface of paper or other print medium using a clay-binding peptide that comprises a clay-binding domain and a print medium binding domain.

Figure 4:
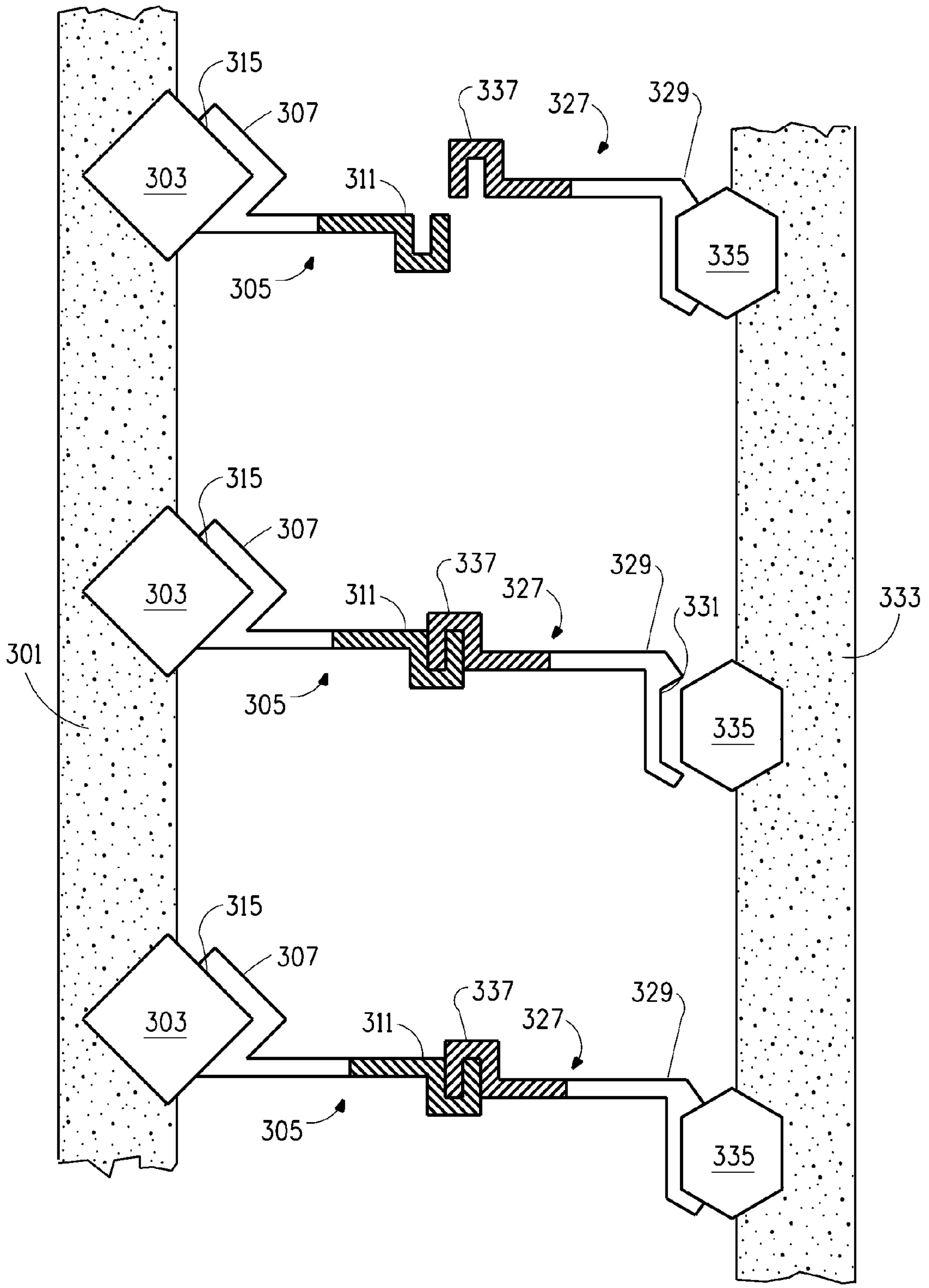
FIG. 4 depicts some embodiments disclosed herein used to bond a clay containing surface with another surface which may contain clay or another known target molecule.
Figure 5:
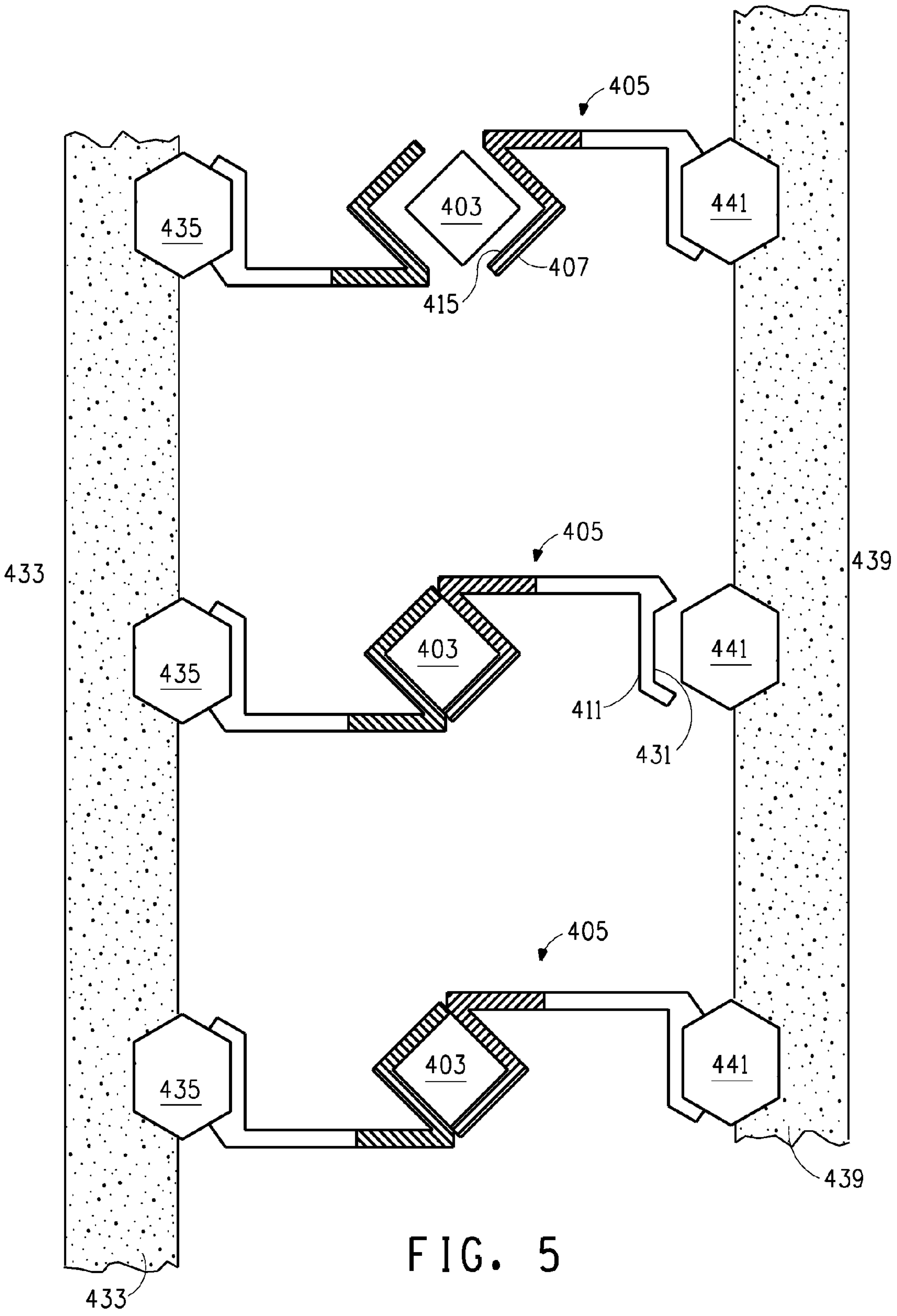
FIG. 5 depicts some embodiments disclosed herein used to bond two surfaces together wherein neither necessarily contains clay.
Figure 6A:
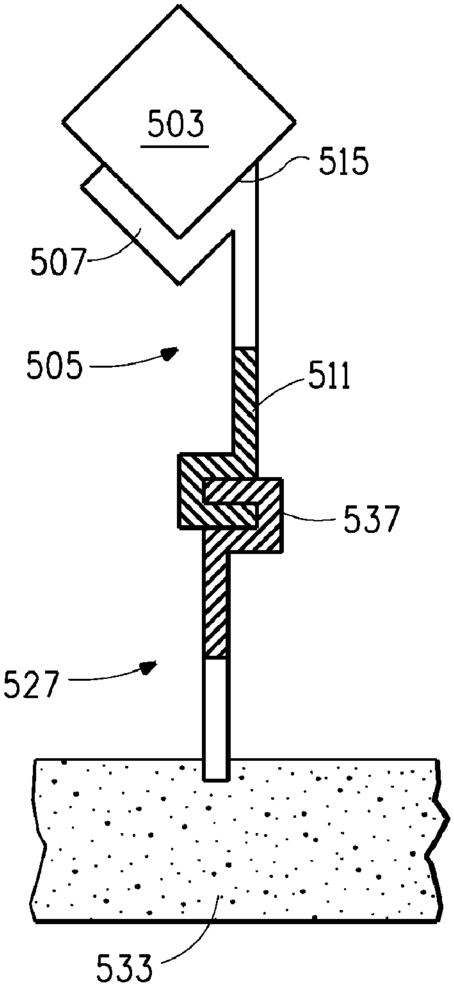
FIG. 6 is a set of panels A-D which depict some embodiments disclosed herein used to coat a surface with clay.
Figure 6B:
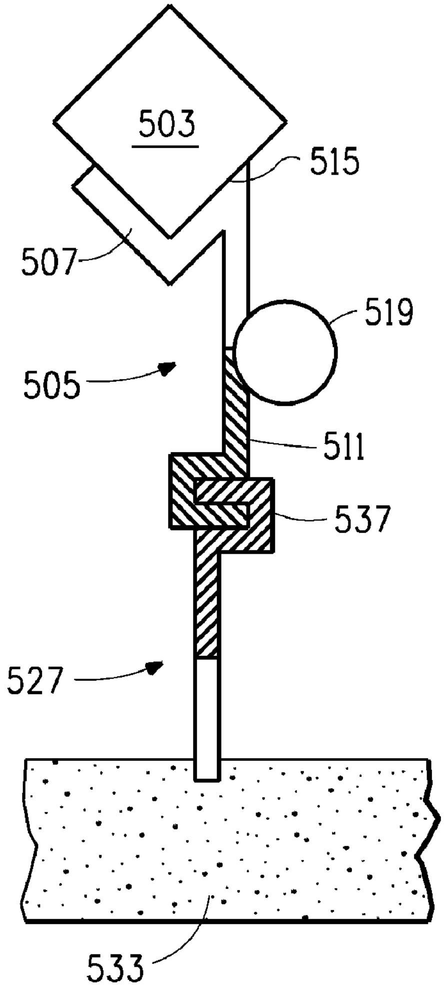
Figure 6C:
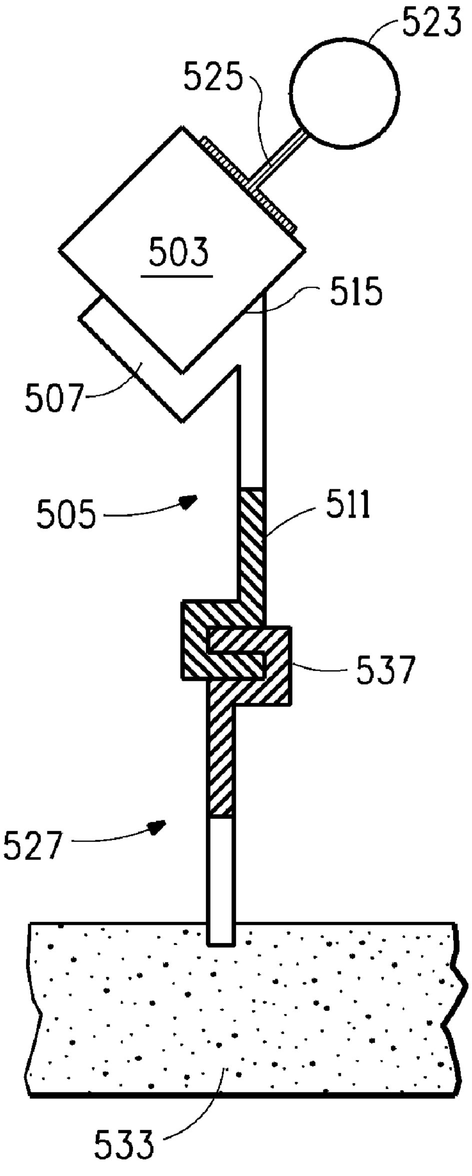
Figure 6D:
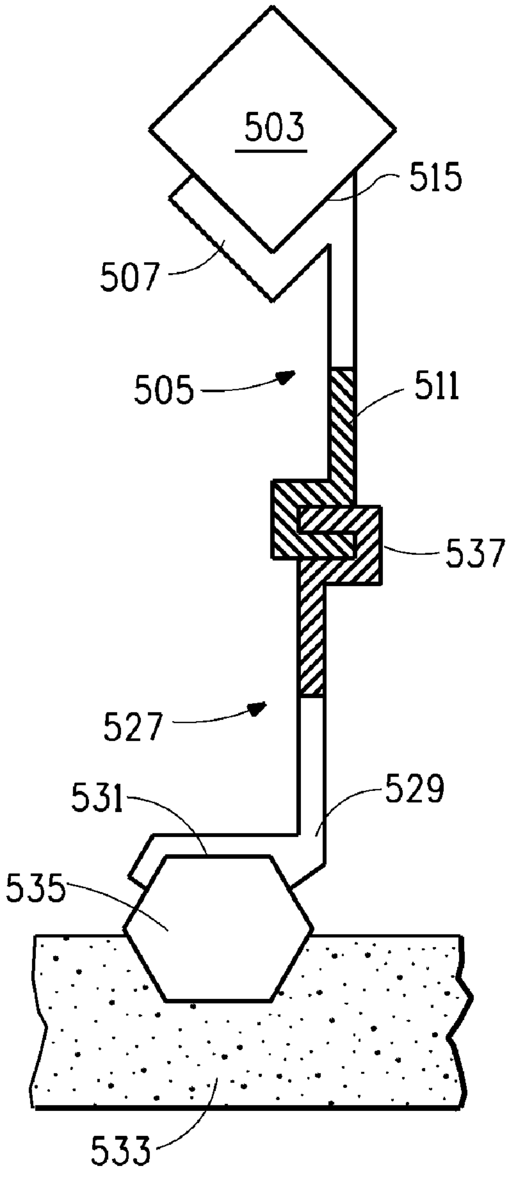

Additional embodiments disclosed herein are illustrated in FIGS. 4 and 5. Referring to FIGS. 4 and 5, a plurality of clay-binding peptides 305 may be employed to bring substances together. FIG. 4 depicts a clay-binding peptide 305 used to bring a clay-containing surface 301 together with another surface 333. The clay-containing surface 301 is comprised in whole or in part of clay moieties 303. At least some clay moieties 303 are exposed in part or in full on the at least one side of the surface 301. Likewise, the non-clay surface or complementary surface 333 is comprised in whole or in part of a known moiety 335 for which there exists a peptide binding-domain 329 or for which a peptide binding domain 329 can be designed using the methods described elsewhere herein. The amino acid structure of the clay-binding peptides 305 comprises in whole or in part of at least one clay-binding domain 307, but possibly more than one. The clay-binding domain 307, itself, comprises at least one or a plurality of clay-binding sites 315. Clay-binding sites 315 are able to bind to the exposed clay moieties 303 of the clay-containing surface 301 and in such way to adhere the clay-binding peptides 305 to surface 301. In addition to comprising one or more clay-binding domains 307, the clay-binding peptide 305 of this embodiment also comprises at least one, but possibly more, target binding domains 311. The target binding domain 311 specifically binds another target domain 337 in a handshake fashion allowing the complex to serve as an adhesive binding the clay and non-clay-containing surfaces together. The target binding domain 311 in some uses may be capable of binding to itself. In that case, the target binding domain 311 and the target domain 337 could be identical.

The complementary surface 333 is composed a known surface-exposed moiety or a complementary moiety 335, for which there is a known peptide binding domain 329, a complementary peptide binding domain 329. A complementary moiety binding peptide 327 is composed of at least one, but possibly more than one, complementary moiety binding domain 329, which itself is composed of at least one but possibly more than one complementary moiety binding site 331. The complementary moiety binding site 331 binds specifically to complementary moieties 335 exposed on the complementary surface 333. The complementary moiety binding peptide 327 is bound to the complementary surface 333 because it is composed of at least one complementary moiety binding domain 329 which contains at least one complementary moiety binding site 331. In addition to the complementary moiety binding domain 329, the complementary moiety binding peptide 327 also contains at least one but possibly more than one target domain 337. As discussed above, the target binding domain 311 of the clay-binding peptide 305 binds to the target domain 337.

It should be clear to one skilled in the art that the complementary surface 333 may be composed of clay itself and the complementary moiety binding domain 327 could be a clay-binding domain. This embodiment is useful because it provides an adhesive that is specific and functional even in adverse circumstances among such circumstances, as not limiting examples, are the presence of water, oil, or dirt.

FIG. 5 depicts another embodiment disclosed herein useful for binding two surfaces together. In this embodiment neither surface needs to necessarily contain clay, although that possibility is not excluded. The primary structure of the peptide based adhesive is similar to that shown in FIG. 4. Two surfaces are provided 433, 439. Each surface comprising a target molecule 435, 441 either of which may or may not be the same and may or not be clay. A reagent is provided comprising in each case a target binding peptide 405 with a target binding domain 411 comprising a target binding site 431. The target binding peptide 405 comprises a clay-binding domain 407 having a clay-binding site 415, useful for binding clay moieties. Juxtaposing of the two surfaces in the presence of clay moieties 403 results in adhesion of the surfaces though the clay.

It will be apparent to the skilled person that this embodiment may also be practiced with the addition of a benefit agent(s) and/or peptide domain(s) as describe above. This embodiment is useful because it provides an adhesive that is specific and functional even in adverse circumstances among such circumstances, as not limiting examples, are the presence of water, oil, or dirt.

FIG. 6 depicts an embodiment disclosed herein in which a surface 533 may be coated with clay 503 using clay-binding peptide 505 containing a target binding domain 511. FIG. 6 panel A depicts a surface 533 coated with a target peptide 527 that contains in part or whole a target domain 537. The target peptide 527 may be applied to the surface 533 by any method either described herein or known in the art; one method will be described in detail later when discussing FIG. 6 panel D. The clay-binding peptides 505 used in this embodiment each contain, as described above, at least one clay-binding domain 507 which in turn contains at least one clay-binding site 515. The clay-binding site 515 binds clay 503 specifically as described elsewhere herein. In addition to the clay-binding domain 507, the clay-binding peptides 505 also each contain at least one but possibly more than one target binding domain 511. The target binding domain used is selected, or created, using methods described or known, to bind specifically to the target domain 537 of the target peptide 527 on the surface 533. If the clay-binding peptide 505 and clay moieties 503 as described are allowed to move freely in a medium around the exposed surface 533, clay-binding peptide 505 will adhere to the peptides 527 on the surface 533 through the bonding of the target binding domain 511 of the clay-binding peptide 505 to the target domain 537 of the surface peptide 527. Clay moieties in the media will bind to the clay-binding site 515 of the clay-binding domain 507 of the clay-binding peptide 505 forming an affinity complex. With clay 503 bound to the clay-binding peptide 505 and it in turn bound to the surface peptides 527 that are bound to the surface 533, clay 503 moieties will coat the surface 533.

FIG. 6 panel B, depicts the same interactions of clay-binding peptide 505, clay 503 and a peptide coated surface 533, as described in panel A, with the addition of a benefit agent 517 coupled to the clay-binding peptide 505 which itself contains at least one target binding domain 511. Using methods described herein this embodiment couples a benefit agent 517 to the clay-binding peptide 505. When the complex of the benefit agent 517 and the clay-binding peptide 505 bind a clay moiety 503 an affinity complex is formed. The affinity complex does not prevent the benefit agent 517 from being functionally active or from the target binding domain 511 from binding the target peptide 527. The addition of a benefit agent 517 to the clay-binding peptide 505 allows the surface to be coated with both a benefit agent 519 and clay moieties 503. Non-limiting examples of benefits agents 517 that may be used with this embodiment are dyes, colorants, antimicrobials, and stain repelling moieties.

FIG. 6, panel C, depicts the same interactions as in panel A, and provides the addition of a benefit agent 523 bound to clay. In this embodiment, the benefit agent 523 is attached to the clay moiety or bead 503 with a bond structure 525. The bonding structure may be part of the benefit agent 523 or may be an independent structure that is bound to the clay 503 for the purpose of binding the benefit agent 523. Or in the alternative, the bond structure 525 may be bound to the benefit agent 523 for the purpose of binding it to the clay 503. The binding structure 523 may be a permanent bond, but in some forms of the embodiment may be easily broken under certain conditions. In other forms of the embodiment the binding structure 525 may allow the benefit agent 523 to be leached from the clay 503 under certain conditions. In still other forms of the embodiment the binding structure might allow the benefit agent 523 to be released over time at regular or specific time intervals or upon certain triggering events. In an alternative form of this embodiment the binding structure 525, itself, may be in whole or in part be composed of clay. In this form, the clay 503 may be in whole or in part the binding structure 525. The benefit agent 523 may be partially or fully embedded with the clay 503. An affinity complex is formed when the benefit agent 523 coupled to the clay moiety 503 that is in turn bound to the clay-binding peptide 505. The affinity complex is capable of binding the target peptide as described above.

FIG. 6 panel D, Depicts a clay-binding peptide 505 and clay moiety or bead 503 similar to the clay-binding peptide 505 described in panel A. In this embodiment, the target peptide 527 depicted is not attached directly to the surface 533. The target peptide 527 contains a target binding domain 537 as in panels A, B, and C and additionally contains a surface moiety binding domain 529. The surface moiety binding domain 529 is selected to bind specifically to a known moiety that is known to be exposed on the surface 533. The surface binding moiety domain 529 contains at least one, but possibly more than one, surface moiety binding site 531. The surface moiety binding site 531 is the point of attachment between the surface moiety 535 and the surface moiety binding domain 529. Through the interaction of the surface moiety binding domain 529 and the surface moiety 535 the clay-binding peptide 505 is attached to the surface 533. Further through the binding interaction of the clay moieties or beads 503 and clay-binding peptide 505 bound to the surface 503, the surface 503 is coated with clay moieties or beads 503.

Application of Clay-Binding Peptides in the Paper Industry

Industrial minerals have long been associated with papermaking and were originally used to reduce costs. For example, clays are considerably cheaper than fiber, and this factor is still a consideration today. However, minerals also impart specific properties to the paper, such as improved printability, brightness, opacity, smoothness and dimensional stability.

Clay fillers are considered a functional additive and are usually added to paper to enhance the optical (opacity and brightness) properties. Additional benefits of fillers include improved sheet formation, surface smoothness, printability and dimensional stability as well as reducing the furnish cost because of the favorable cost differential between fillers and fiber. However, the addition of filler interferes with the fiber-to-fiber bonding, as well as replacing some of the fiber, resulting in sheet strength reduction.

Consequently, the papermaker must manage the clay filler level to optimize the benefits without sacrificing too much strength. Filler suppliers can manipulate the mineral properties such as particle size, particle shape, particle size distribution etc. in order to minimize the impact on strength. However, there are limits to these manipulations, especially with naturally occurring mineral fillers. Additionally, changes that improve strength generally reduce the optical and other benefits.

Fillers are not simply inert optical entities; they interact with other additives, not only in terms of their own distribution but also to influence sheet structure, e.g. formation, bulk, pore structure and surface topography (texture). Aside from their optical effects, fillers or filler blends can be used to improve aspects of product uniformity and quality. Mastery of this technology requires an understanding of filler interactions with retention aids, sizing agents, cationic starch and the dynamics of the wet end forming system.

The main disadvantage of higher clay filler level is the deterioration of fiber-to-fiber bonding. This leads to lower stiffness and strength (above that resulting from higher density). The main thrust of high filler technology is to overcome the problems with reduced strength. As mentioned earlier, apart from the loss in strength, changes in product quality are seen to be aesthetic: poor "feel", low rattle and a general feeling of limpness. Surface dusting is higher as well as a tendency to an increased propensity to pick. As mentioned previously, the need for refining is increased to achieve the same strength levels. Finally a more efficient retention system will be necessary to cope with the increase.

Filled paper may be made by a process comprising providing a dilute aqueous suspension (termed a thinstock) of cellulosic fibers and filler, draining the thinstock suspension to form a sheet, and drying the sheet. It is desirable to retain as much as possible of the filler and fiber, including fiber fines, in the sheet and it is normal to add a retention aid to the thinstock in order to promote retention.

The thinstock is usually made by diluting with water (typically whitewater from the drainage stage if paper-making) a more concentrated suspension of filler and cellulosic fiber. This more concentrated suspension is normally called the thickstock. The thickstock may be made by blending together the desired amounts of fiber, filler and water. Typically, the thickstock suspension comprises about 2.5% to about 20% by weight of clay and cellulosic fiber in a dry weight ratio of about 10:1 to about 1:50. Typically, the thinstock is formed in an amount of about 0.02% to about 2% dry weight based on the dry weight of the suspension.

Some of the feed to the thickstock can be recycled material, for instance deinked pulp, and if the recycled pulp contains filler this previously used filler will be incorporated into the thickstock. Often additional, previously unused, filler is incorporated into the thickstock or thinstock.

Polymers of a wide range of molecular weights can be used as retention aids, and it is also known to add a high weight polymeric retention aid to the thinstock after incorporating a lower molecular weight polymeric coagulant into the thinstock or even the thickstock.

For instance it is known to treat unused filler with polymeric coagulant before adding that filler to the thickstock. The purpose of this coagulant addition is to coagulate the filler and thereby improve its retention. Unfortunately the process tends to result in the filler being less satisfactory (e.g. it gives less opacification to the paper) and so the addition of coagulant in this manner is not entirely satisfactory.

In many processes for making filled paper, a cationic, high weight, retention aid is added to the thinstock formed from good quality pulp (of low cationic demand). In such processes, the addition of retention aid usually results in improved retention of both filler and fines.

In order to improve filler and fines retention in paper-making processes to improve the yield on the starting materials and also to reduce the volume of the waste stream from paper-making, one or more clay-binding peptide reagents described herein may be added to the thickstock. The clay-binding peptide for this use include, but are not limited to, those having the general structure:

$(CLAYBD_x\text{-}TBD_y)_n$ or $[(CLAYBD_x\text{-}L_s)_q\text{-}(TBD_y\text{-}L_t)_r]_n$, wherein the clay-binding domain is specific for the clay employed in the process. The clay-binding peptide reagent may be added to the thickstock at a concentration of about 0.001% to about 5% dry weight based on the dry weight of the suspension. The clay-binding peptide reagent may also be added to the diluted thinstock, to the whitewater utilized in the dilution of the thickstock to thinstock, to the clay before addition of the clay to the thickstock, or any combination thereof.

In papermaking, it is often desirable to coat one or both surfaces of the paper or paperboard to impart desirable properties to that surface. The coating process can improve one or more of the properties such as gloss, opacity, color, barrier properties, ink reception, hand (i.e., a subjective assessment of the quality of the feel of fabric, leather, paper or other sheet materials. Good hand is soft, silky, cottony, drapable, suede-like, etc. Fine materials may also feel dry or brittle or harsh and so would have a poor hand.), or density. Generally, polymeric or surfactant compounds are added to a clay or other particulate material in the formulation of the coating suspension. In this embodiment, peptides such as those having the structures:

$(CLAYBD_x\text{-}TBD_y)_n$ or $[(CLAYBD_x\text{-}L_s)_q\text{-}(TBD_y\text{-}L_t)_r]_n$ wherein the TBD is specific to cellulose and the CLAYBD is specific to the particular clay being used may be employed to promote adhesion of the particulate clay materials to the cellulose of the paper. Subsequent to the process of making the paper and the coating suspension, the coating process includes the actual coating, drying and calendering. This method may also be used to prepare carbonless copy paper, commonly referred to as NCR paper, ubiquitous in preparing paper records for the credit card industry. NCR paper is a two-paper system, one of the papers having a special clay coating and the other having microencapsulated materials where writing on the paper or passing it through a credit card embosser or cash register breaks the capsules and transfers the chemical to the clay layer where an image appears as a result of the chemical reaction.

In papermaking, the finishing operation may be a calendering process, in which a paper web is passed between the nips formed between one or more pairs of rolls and the surface of the web is thereby flattened to form a smooth surface. Simultaneously, the thickness, or caliper, of the paper web is reduced and the web is densified.

Calendering generally reduces caliper, and, as a result, a higher density is obtained in the finished paper product. Bulk is inversely related to density, therefore when the density is increased, the bulk of finished paper product will be reduced. Calendering may generally be accomplished using a gloss calender, a soft calender or a supercalender.

The gloss calender is typically comprised of a hard, non-resilient, heated roll made, for example, of steel, positioned proximally to a soft roll so as to form a narrow gap or nip. As the web passes through the nip it is exposed to a nip load in the range of from about 100 to about 900 pounds per lineal inch (pli). Nip pressures in this type of device are usually in the range of less than about 2000 pounds per square inch (psi). A wide range of processing temperatures can be used in a gloss calender, with the typical maximum temperature being in the range of about 200° C. The finishing effect achieved using the gloss calender, however, is not as smooth or as flat, and therefore not as glossy, as the surface produced using an apparatus capable applying higher pressure.

It is therefore often useful to increase the nip load or the roll temperature, or both, to plasticize and smooth the surface layers of the paper. Such modifications are incorporated, for example, in the design and operation of the conventional soft calender. The soft calender is usually constructed as having one to two nips per coated side, or as a two- or four-nip device, with each nip being formed between a heated hard roll and an unheated soft roll.

Alternatively, supercalendering may be used as the finishing operation. In such a process, the web is sequentially passed between a series of nips formed between the vertically stacked rolls of a supercalender. The supercalender typically comprises a frame having an upper roll and a lower roll between which are positioned intermediate rolls. The rolls of the supercalender may be heated hard rolls or unheated soft rolls, in serial or alternating arrangement. As the web is passed through each nip, the web is compacted to form paper of substantially uniform density and high gloss by virtue of the repeated pressurization and heat exposure. In a supercalender, the nips are loaded initially by gravity, i.e., gravitational forces acting on the weight of the rolls themselves produce a distribution of the weight from the upper nip to the bottom nip that is substantially linear and increasing. This has the consequence that the load present in the bottom nip actually determines the loading capacity of the calender stack.

As used herein, "paper product" includes all varieties of finished paper or paperboard materials. The term "high gloss" means a TAPPI gloss value of greater than 60, as determined at a 75° angle of reflectance.

In the method of one embodiment, a coating formulation is applied to the surface of a base stock before finishing. The "base stock" may be a dried web or sheet or material otherwise formed from a paper furnish comprised of wood pulp and, optionally, other additives. Preferably, the pulp is a comprised mainly of chemical pulp, but the furnish may contain, if desirable, other types of pulp including mechanical pulp, semi-chemical pulp, recycled pulp, pulp containing other natural fibers, synthetic fibers, and any combination thereof. The base stock may be of any suitable fiber composition having a uniform dispersion of cellulosic fibers alone or in combination with other fiber materials, such as natural or synthetic fiber materials. Examples of suitable substrates include previously coated or uncoated paper or paperboard stock.

The coating formulation comprises a solid particulate pigment in a suitable solvent, and in the case of this disclosure the particulate pigment is a clay or a pigment coated with a clay. Suitable solvents include water, and mixtures of water with water-miscible organic solvents, such as glycols and alcohols. The coating formulation further comprises one or more clay-binding peptides including, but not limited to, those having the structures:

$(CLAYBD_x\text{-}TBD_y)_n$ or $[(CLAYBD_x\text{-}L_s)_q\text{-}(TBD_y\text{-}L_t)_r]_n$ (wherein the TBD is specific to cellulose and the CLAYBD is specific to the particular clay being used. The peptide reagent is employed to promote adhesion of the particulate clay materials to the cellulose of the paper. The brightness of the clay may be selected based on the brightness requirement for the finished product, and, accordingly, high or regular brightness clay may be used. Such clays may include No. 1 or No. 2 clays and kaolin clay. Examples of these are HYDRAFINE 90, available commercially from J. M. Huber Corporation, and ALPHACOTE and PREMIER No. 1 from English China Clay Inc (now Imrys). Preferably, regular or high brightness kaolin clay is used. The amount of clay added to the coating formulation may be up to about 90 parts by weight based on the total weight of the dry pigment. Other conventional additives, such as binders, opacifiers, whitening agents, pigments, starch, polyvinyl alcohol may be added to improve various properties of the coating process or the final coated paper product.

In one embodiment, a base stock is formed and at least one side of the base stock is coated with the coating formulation described above, which comprises a clay-binding peptide reagent. The base stock may be coated using methods known in the art, such as applying the coating with a jet applicator blade metering coater, a film coater, or a combination of these coating methods to obtain multiple layer coatings. The coated base stock is then passed through a calendering device, as described above, to form the clay-coated paper or paperboard.

In one embodiment, the CLAYBD is specific to the particular clay being employed and the TBD is specific to cellulose.

In another embodiment, CLAYBD is specific to the particular clay being employed and the TBD is specific to an ink pigment.

Intercalation and Exfoliation of Clays Using Clay-Binding Peptides

One embodiment disclosed herein is directed to intercalated layered materials, and exfoliates thereof, manufactured by sorption (adsorption and/or absorption) of one or more clay-binding peptides between planar layers of a sellable layered material, such as a clay or phyllosilicate, to expand the interlayer spacing of adjacent layers to at least about 10 Å. More particularly, one embodiment is directed to intercalates having at least two layers of clay-binding peptide molecules sorbed on the internal surfaces of layers of the platelets of a layered material, such as a phyllosilicate, preferably a smectite clay, to expand spacing to at least about 10 Å, preferably to at least about 20 Å, and more preferably to at least about 30-45 Å, up to about 100 Å, or disappearance of periodicity. The resulting intercalates are neither entirely organophilic nor entirely hydrophilic, but a combination of the two, and easily can be exfoliated for or during admixture with a polymer, ink, pigment, or other material. When the admixture is with a polymer, the polymer is a thermoplastic or thermosetting polymer melt, preferably a thermoplastic matrix polymer and the exfoliated layered material improves one or more properties of the matrix polymer. The resulting matrix polymer/platelet composite are useful wherever polymer/filler composite materials are used, for example, as external body parts for automotive industry; heat-resistant polymeric automotive parts in contact with an engine block; tire cord for radial tires, food wrap having improved resistance to gas impermeability; electrical components; food grade drink containers; and any other use where it is desired to alter one or more physical properties of a matrix polymer, such as elasticity and temperature characteristics, e.g., glass transition temperature and high temperature resistance.

It is well known that phyllosilicates, such as smectite clays, e.g., sodium montmorillonite and calcium montmorillonite, can be treated with organic molecules, such as organic ammonium ions, to intercalate the organic molecules between adjacent, planar silicate layers, thereby substantially increasing the interlayer (interlaminar) spacing between the adjacent silicate layers. The thus-treated, intercalated phyllosilicates, having interlayer spacing of at least 10-20 Å and up to about 100 Å, can be exfoliated, e.g., the silicate layers are separated by high shear mixing. Individual silicate layers, when admixed with a matrix polymer, before, after or during the polymerization of the matrix polymer have been found to substantially improve one or more properties of the polymer, such as mechanical and/or high temperature characteristics. Examples of such composites, also called "nanocomposites", are described by Maxfield et al. in WO 93/04118 and U.S. Pat. No. 5,385,776.

One embodiment disclosed herein is directed to intercalates formed by contacting a layered phyllosilicate with a clay-binding peptide to sorb or intercalate the peptide or mixtures of peptides between adjacent phyllosilicate platelets. The clay is contacted with a composition comprising a clay-binding peptide reagent at a concentration of at least about 2% by weight of the composition. Additionally, a mixture of different clay-binding peptide reagents may be used. If a mixture is used, the total concentration of clay-binding peptide reagents is about 2% by weight of the composition. The peptide reagent may be any of those described above. In one embodiment the peptide reagent has the general structure:

$$(CLAYBD_x\text{-}TBD_y)_n \quad \text{or} \quad [(CLAYBD_x\text{-}L_s)_q\text{-}(TBD_y\text{-}L_t)_r]_n$$

wherein the clay-binding domain is specific for the particular clay being used. In one embodiment, the TBD is selective for binding a material, including, but not limited to, polymers, body surfaces, print media, biological analytes, plant fibers, synthetic fibers, and benefit agents. Sufficient clay-binding peptide is sorbed between adjacent phyllosilicate platelets to expand the spacing between adjacent platelets (interlayer spacing) to a distance of at least about 10 Å (as measured after water removal) and preferably in the range of about 30-45 Å, so that the intercalate can be easily exfoliated (i.e., the platelets of the intercalated clay may be easily separated). The platelets of the intercalated clay may be separated naturally without shearing being necessary. At times, shearing may be required and may be readily accomplished using methods known in the art. For example, shearing may be required when mixing the intercalate with a polymer melt, to provide a matrix polymer/platelet composite material or nanocomposite, the platelets being obtained by exfoliation of the intercalated phyllosilicate. The clay-binding peptide should comprise a clay-binding domain having a specific affinity for the phyllosilicate so that it is sorbed between, and is maintained associated with the silicate platelets in the interlayer spaces, and after exfoliation.

While not wishing to be bound by theory, we note that it is likely that the clay-binding peptide should comprise a functionality to be sufficiently bound to metal cations by complexing or chelation of the metal cations of the phyllosilicate. Such clay-binding peptides may have sufficient affinity for the phyllosilicate platelets to maintain sufficient interlayer spacing for exfoliation, without the need for coupling agents or spacing agents, such as commonly used anion or silane coupling agents.

Once exfoliated, the platelets of the intercalate are predominantly completely separated into individual platelets and the originally adjacent platelets are no longer retained in a parallel, spaced disposition, but are free to move as predominantly individual platelets throughout a matrix polymer melt to act similar to a nanoscale filler material for the matrix polymer. Once the polymer/platelet composite material is set and hardened into a desired shape, the predominantly individual phyllosilicate platelets are permanently fixed in position and are randomly, homogeneously and uniformly dispersed, predominantly as individual platelets, throughout the matrix polymer/platelet composite material.

As recognized, the thickness of the exfoliated, individual platelets (about 10 Å) is relatively small compared to the size of the flat opposite platelet faces. The platelets have an aspect ratio in the range of about 200 to about 2,000. Dispersing such finely divided platelet particles into a polymer provides a very large area of contact between polymer and platelet particles, for a given of particles in the composite, and a high degree of platelet homogeneity in the composite material. Platelet particles of high strength and modulus, dispersed at sub-micron size (nanoscale), impart greater mechanical reinforcement and a higher glass transition temperature (Tg) to the polymer matrix than do comparable loadings of conventional reinforcing fillers of micron size, and can impart lower permeability to matrix polymers than do comparable loadings of conventional fillers.

Additionally, the intercalated or exfoliated clays may be used in paper making as a filler or a coating. These paper products may be prepared using the methods described above.

An important class of clays is the organically-modified clays, well known in the art. These include the intercalated clays described above. They also include a class of materials referred to as "pillared clays." These materials have been intercalated with longer molecules that serve to hold the hold the clay layers apart at a fixed distance while leaving room between the pillars. These materials are useful absorbents as a result of the space between the pillars. The structures are also amenable to reaction with the clay-binding peptides described herein. Because the layers are already open, intercalation of the peptides may be facilitated.

Personal Care Compositions

The personal care compositions disclosed herein include any composition that may be applied to the skin, hair, eyelashes, eyebrows, lips, or nails to provide a cosmetic or beneficial effect. These personal care compositions include, but are not limited to, skin care compositions, skin cleansing compositions, make-up, facial lotions, cream moisturizers, body washes, bar soaps, bath foam bath salts, body lotions, body mists, foot creams, hand creams, lipstick, eyeshadow, foundation, facial powders, deodorant, sunscreens, shaving cream compositions, nail polishes, shaving lotions, cream depilatories, lotion depilatories, facial masks made with clay materials, blushes, bronzers, concealers, anti-aging products, hydroalcoholic toners, foundations, makeup primers, mascaras, powders, shimmers, paste masks, eyeliners, hair conditioners, hair treatment creams, styling gels, styling foams, hair mousses, hair sprays, set lotions, blow-styling lotions, hair color lotions, and hair relaxing compositions. The personal care products comprise a clay mineral, including exfoliated or intercalated clays, treated with one or more clay-binding peptides, including, but not limited to, those having the general structure:

$(CLAYBD_x\text{-}TBD_y)_n$ or $[(CLAYBD_x\text{-}L_s)_q\text{-}(TBD_y\text{-}L_t)_r]_n$ In this embodiment, the TBD has a high affinity for a variety of functional ingredients including, but not limited to, chelating agents, colorants, dispersants, emollients, emulsifiers, fragrances, humectants, UV absorbing materials, opacifying agents, preservatives, skin conditioners, or thickener. Similarly, personal care compositions may comprise a clay mineral treated with one or more clay-binding peptides having the general structure:

$(CLAYBD_x\text{-}BA_p)_n$ or $(CLAYBD_x\text{-}L\text{-}BA)_n$ wherein the benefit agent is covalently linked, either directly or through a linking molecule, to the clay-binding peptide domain. In the two examples above, the clay may also serve the function of a chelating agent.

As described above, clay-binding peptides such as those having the general structure:

$(CLAYBD_x\text{-}TBD_y)_n$ or $[(CLAYBD_x\text{-}L_s)_q\text{-}(TBD_y\text{-}L_t)_r]_n$ wherein the TBD has affinity for a body surface, such as skin, hair, nails, and the like, may be used in various personal care compositions to color body surfaces. In this embodiment, either the natural color of the clay or a colored clay is used.

One embodiment disclosed herein pertains to personal care compositions which have skin conditioning and protection properties. The compositions may be in the form of a liquid or gel, such as hand washes and the like, or in the form of a bar soap, or for shower and bath application or a conditioning shampoo. The benefit agent is attached to the body surface through the body surface binding domain of the clay binding peptide and thus is persistent and the derived benefits may be maintained through washings and routine environmental exposure.

A wide variety of products are commonly available as skin conditioners. These compositions comprise one or more emollients, or skin conditioners, in a vehicle. The vehicle is typically optimized to provide for a method of depositing or contacting the skin with the emollient. More recently, these products have taken the form of hand and body washes the like. It remains difficult, however, to provide a formulation which can be applied in an environment of high water dilution, such as a shower or bath, as well as directly on the skin rinsing, and achieve significant improvements in skin conditioning. Modification of the clay particles with clay-binding peptides that also bind to skin, hair or other body surfaces will provide long-lasting adhesion of the clay particle to those surfaces.

One particularly advantageous application would be to bind titanium dioxide nanoparticles to the surface of a clay particle and to use clay-binding peptides designed for edge-binding to bind the clay particle to skin. The result would be a long-lasting sunscreen that would survive salt- or pool-water exposure and even bathing. Other ultra-violet radiation (UV) absorbers such as zinc oxide, cerium oxide and iron oxide may also be used, either alone or in combination with titanium dioxide nanoparticles.

Additionally, clays are popular particulate gellants or thickeners for aqueous compositions, particularly oil-in-water emulsions. These are particularly important in the formulation of personal care products. Fundamentally, the formation of particulate gels is a manifestation of suspended colloidal particles forming a network structure that entraps and thus immobilizes the suspending medium. Clay-based gels may form when individual platelets or stacks of a few aggregated platelets (tactoids) engage in interparticle associations with their neighboring platelets. If these particle-toparticle links extend throughout the total available volume, a gel, comprised of a continuous, linked particulate structure that entraps within itself the suspending medium, is formed. Such interparticle associations are governed by the interplay between the attractive and repulsive forces that generally act between particles suspended in a liquid. Hydrodynamic effects due to the orientation of planar clay particles in a flow-field may also contribute to the rheological properties of clay suspensions.

The strength of particulate gels will depend on the number of interparticle associations in a given volume of the gel, implying that the greater the number-concentration of suspended particles, the stronger is the gel. Also, a dominance of the attractive interactions over the repulsive interactions, the likelihood of which increases with a decrease in interparticle separation distance, is required for suspended particles to associate with their neighbors. An increase in the number-concentration of particles will tend to reduce their separation distances, an effect that could be especially dramatic for planar particles since the separation distance between two adjacent platelets will vary along their lengths when their faces do not align in parallel configuration. Nonetheless, too strong an attraction between adjacent clay platelets may draw them into strong association or coagulation, minimizing the particle number-concentration, once such coagulation occurs via face-to-face associations. In fact, it is these attractive forces that hold the clay platelets together in a stack. The clay-binding peptides described herein are ideal for the modification of the surface to surface interactions between clay particles.

Considering the above, the key to making clay-based gels is to ensure that there is sufficient interplatelet repulsion for the clay platelets to exfoliate (delaminate or deflocculate) under shear, releasing a large number of platelets as individual platelets or tactoids having fewer stacked platelets, that would then be available to form a particle network, on the other hand, in order to form a voluminous network structure, the net interaction (the sum of attractive and repulsive forces) between the delaminated platelets must be such that they can remain “bound” (attracted) to their neighboring platelets without being drawn into coagulation with their neighbors via face-to-face association.

Accordingly, the gel-network may form if the delaminated platelets, while being separated from the surrounding platelets by as thick as possible an intervening layer of the suspending medium, reside in a relatively deep minimum in free energy of interaction with the neighboring platelets. Albeit physically separated from their neighbors, the individual platelets are no longer free to move independently, being trapped in a free energy minimum, producing in effect a continuous particle network, and hence thickening or gelation.

Yet another way by which clay-based gels may form is where clay platelets coagulate due to edge-to-face associations, forming the so-called “card-house” structure described in clay literature. It may be possible to finely tune this interaction by the proper combination of peptides designed to bind to the face of the clay platelets coupled to peptides designed to bind to the edges of the clay platelets.

Forming clay-based gels, as an outcome of the aforementioned phenomena, would require tuning of interplatelet forces as described. Adding complexity, these attractive and repulsive forces may vary the properties of the suspending medium. Evidence of this may be found in that the clay-based gels form far more easily in pure water than in hydrophilic organic solvents such as glycols, glycerols and alcohols. It is therefore an object of the present disclosure to modify the surface of a clay in a manner that provides for achieving the thickener-performance of the particulate material in water and/or in one or more hydrophilic solvents, particularly the solvents used in personal care and cosmetic product manufacturing. An underlying goal of such clay-surface modification is to stabilize the clay platelets against strong face-to-face aggregation, such that the suspended-state of the delaminated platelets may be preserved over extended periods of time.

A number of the embodiments described herein may be used in hair care compositions. Hair care compositions are herein defined as compositions for the treatment of hair, including but not limited to shampoos, conditioners, lotions, aerosols, gels, mousses, and hair dyes. If the clay-binding peptides described herein are desired to be used in connection with a hair care composition, an effective amount of the peptide reagent for use in a hair care composition is herein defined as a proportion of from about 0.01% to about 10%, preferably about 0.01% to about 5% by weight relative to the total weight of the composition. Components of a cosmetically acceptable medium for hair care compositions are described by Philippe et al. in U.S. Pat. No. 6,280,747, and by Omura et al. in U.S. Pat. No. 6,139,851 and Cannell et al. in U.S. Pat. No. 6,013,250, all of which are incorporated herein by reference. For example, these hair care compositions can be aqueous, alcoholic or aqueous-alcoholic solutions, the alcohol preferably being ethanol or isopropanol, in a proportion of from about 1 to about 75% by weight relative to the total weight, for the aqueous-alcoholic solutions. Additionally, the hair care compositions may contain one or more conventional cosmetic or dermatological additives or adjuvants including but not limited to, antioxidants, preserving agents, fillers, surfactants, UVA and/or UVB sunscreens, fragrances, thickeners, wetting agents and anionic, nonionic or amphoteric polymers, and dyes or pigments. These adjuvants are well known in the field of cosmetics and are described in many publications, for example see *Harry's Cosmeticology,* 8th edition, Martin Rieger, ed., Chemical Publishing, New York (2000).

A number of embodiments disclosed herein may be used in a skin care composition. Skin care compositions are herein defined as compositions comprising an effective amount of a skin conditioner or a mixture of different skin conditioners in a cosmetically acceptable medium. The uses of these compositions include, but are not limited to, skin care, skin cleansing, make-up, and anti-wrinkle products. If it is desired to use the methods or materials disclosed herein in connection with a skin care composition an effective amount of the peptide reagent for skin care compositions is herein defined as a proportion of from about 0.001% to about 10%, preferably about 0.01% to about 5% by weight relative to the total weight of the composition. This proportion may vary as a function of the type of skin care composition. Suitable compositions for a cosmetically acceptable medium are described by Philippe et al. supra. For example, the cosmetically acceptable medium may be an anhydrous composition containing a fatty substance in a proportion generally of from about 10 to about 90% by weight relative to the total weight of the composition, where the fatty phase containing at least one liquid, solid or semi-solid fatty substance. The fatty substance includes, but is not limited to, oils, waxes, gums, and so-called pasty fatty substances. Alternatively, the compositions may be in the form of a stable dispersion such as a water-in-oil or oil-in-water emulsion. Additionally, the compositions may contain one or more conventional cosmetic or dermatological additives or adjuvants, including but not limited to, antioxidants, preserving agents, fillers, surfactants, UVA and/or UVB sunscreens, fragrances, thickeners, wetting agents and anionic, nonionic or amphoteric polymers, and dyes or pigments. These adjuvants are well known in the field of cosmetics and are described in many publications, for example see *Harry's Cosmeticology*, supra.

Among these adjuvants, the fillers are generally present in personal care products in a maximum proportion of about 99.9% by weight relative to the total weight of the composition. These fillers, in the form of very fine powders, can be of natural or synthetic origin and include, but are not limited to, mineral powders, such as talc, kaolin, mica, silica, silicates, alumina, zeolites, hydroxyapatite, sericite, titanium dioxide, titanium micas, barium sulfate, calcium carbonate, calcium sulfate, bismuth oxychloride, boron nitride and metal powders such as aluminum powder; plant powder, such as corn starch, wheat starch or rice starch powders; organic powders, such as polyamide powder, polyester powder, polytetrafluoroethylene powder, the powder of fluorinated alkanes, polyethylene powder and other inert plastics. These various powders can also be coated, for example with metal salts of fatty acids, amino acids, lecithin, collagen, silicone compounds, fluoro compounds or with any common coating agent.

In one embodiment, the skin care composition comprises a clay, a clay-binding peptide and a solvent which is an oil in water emulsion. The solvent is present in an amount of at least about 60%, in addition at least about 70%, and in addition at least about 80% by weight relative to the total weight of the composition. The skin care composition may further comprise at least one solubilizing agent, including, but not limited to, polyethylene glycol ether of a fatty alcohol, a polyethylene glycol ether of hydrogenated castor oil, a polyethylene glycol derivative of a sorbitan ester, a polysorbate, a propylene glycol, a glycerol ester, a polyethylene glycol derivative of a glycerol ester, an alkyl phosphate, and an alkyl sulfate. The solubilizing agent is typically present in an amount less than about 10% by weight relative to the total weight of the composition.

In another embodiment, the skin care composition comprises a clay, a clay-binding peptide and a solvent which is an oil in water emulsion, as described above, and the clay binding peptide has the general structure:

$(CLAYBD_x\text{-}TBD_y)_n$ or $[(CLAYBD_x\text{-}L_s)_q\text{-}(TBD_y\text{-}L_t)_r]_n$ wherein the clay-binding domain (CLAYBD) is selective for the edge of a clay particle or the face of a clay particle. Additionally, the TBD may have a specific affinity for one or more substrates, including but not limited to UV radiation absorbing materials, such as titanium dioxide, zinc oxide, cerium oxide and iron oxide; pigments; and dyes.

The skin care compositions described herein may be prepared using the following process: adding a clay to a solvent which comprises water, adding one or more clay-binding peptide reagents, as described herein, adding an oil, and homogenizing the mixture.

The skin care compositions disclosed herein may be used to effect at least one of the following skin moisturizing, skin hydrating, skin smoothing, and skin softening.

Printing Applications

One application of the peptide reagents described herein is in aqueous inks, such as ink jet inks. These inks may be used to print onto a clay-coated paper. In this embodiment, the peptide reagent comprises a clay-binding domain coupled to a pigment or a clay-binding domain and a pigment-binding domain. In either case, the clay-binding domain binds to a clay-coated paper surface, thereby attaching the pigment to the paper.

Aqueous ink formulations are well known in the art. For example suitable formulations are described by Ma et al. in U.S. Pat. No. 5,272,201 and by Ma et al. in U.S. Pat. No. 5,085,698, both of which are incorporated herein by reference. Aqueous ink formulations typically comprise an aqueous carrier medium, a pigment or a mixture of pigments, a dispersant, and various other ingredients.

The aqueous carrier medium comprises water or a mixture of water and at least one water-soluble organic solvent. Deionized water is commonly used. Representative examples of water-soluble organic solvents are disclosed by Ma et al. in U.S. Pat. No. 5,085,698. The selection of a suitable mixture of water and water-soluble organic solvent depends upon the requirements of the specific application, such as the desired surface tension and viscosity, the selected pigment, drying time of the ink, and the type of media substrate onto which the ink will be printed. A mixture of a water-soluble polyhydric alcohol having at least 2 hydroxyl groups, e.g., diethylene glycol, and deionized water is preferred as the aqueous carrier medium, with water comprising between about 30% and about 95%, preferably about 60% to about 95%, by weight, based on the total weight of the aqueous carrier medium. The amount of aqueous carrier medium is in the range of about 70% to about 99.8%, preferably about 94% to about 99.8%, based on total weight of the ink when an organic pigment is selected, and about 25% to about 99.8%, preferably about 70 to about 99.8% when an inorganic pigment is selected.

The pigment may be a single pigment or a mixture of pigments. Suitable pigments for printing applications are described above. The ink may contain up to about 30% pigment by weight, preferably the amount of pigment is between about 0.1% to about 15% by weight.

The peptide reagents described herein may be used alone or in combination in the ink formulation. The peptide reagent is present in the ink composition in the range of about 0.1% to about 30% by weight.

The peptide reagent may serve as a dispersant for the pigment, or conventional dispersants or self-dispersing pigments may be used. When a dispersant is used to disperse the pigment, the dispersant may be any suitable dispersant known in the art, including, but not limited to, random or structured organic polymeric dispersants, as described below; protein dispersants, such as those described by Brueckmann et al. (U.S. Pat. No. 5,124,438); and peptide-based dispersants, such as those described by O'Brien et al (copending and commonly owned U.S. Patent Application Publication No. 2005/0054752). Preferred random organic polymeric dispersants include acrylic polymer and styrene-acrylic polymers. Most preferred are structured dispersants, which include AB, BAB and ABC block copolymers, branched polymers and graft polymers. Preferably the organic polymers comprise monomer units selected from the group consisting of acrylate, methacrylate, butyl methacrylate, 2-ethylhexyl methacrylate, benzylmethacrylate, phenoxyethyl acrylate, and ethoxytriethyleneglycolmethacrylate, such as those described by Nigan (U.S. Patent Application Publication No. 2004/0232377). Some useful structured polymer dispersants are disclosed in U.S. Pat. No. 5,085,698, EP-A-0556649 and U.S. Pat. No. 5,231,131 (the disclosures of which are incorporated herein by reference). Additionally, pigments may be dispersed using a surface active agent comprising lignin sulfonic acids and a polypeptide, as described by Cioca et al. in U.S. Pat. No. 4,494,994, which is incorporated herein by reference.

A self-dispersing pigment is a pigment that has been surface modified with chemically attached, dispersibility imparting groups to allow stable dispersion without a separate dispersant. For dispersion in an aqueous carrier medium, surface modification involves addition of hydrophilic groups and most typically ionizable hydrophilic groups. The self-dispersing pigment may be prepared by grafting a functional group or a molecule containing a functional group onto the surface of the pigment, by physical treatment (such as vacuum plasma), or by chemical treatment (for example, oxidation with ozone, hypochlorous acid or the like). A single type or a plurality of types of hydrophilic functional groups may be bonded to one pigment particle. Self-dispersing pigments are described, for example, in U.S. Pat. No. 5,571,311, U.S. Pat. No. 5,609,671, U.S. Pat. No. 5,968,243, U.S. Pat. No. 5,928,419, U.S. Pat. No. 6,323,257, U.S. Pat. No. 5,554, 739, U.S. Pat. No. 5,672,198, U.S. Pat. No. 5,69,8016, U.S. Pat. No. 5,718,746, U.S. Pat. No. 5,749,950, U.S. Pat. No. 5,803,959, U.S. Pat. No. 5,837,045, U.S. Pat. No. 5,846,307, U.S. Pat. No. 5,895,522, U.S. Pat. No. 5,922,118, U.S. Pat. No. 6,123,759, U.S. Pat. No. 6,221,142, U.S. Pat. No. 6,221, 143, U.S. Pat. No. 6,281,267, U.S. Pat. No. 6,329,446, U.S. Pat. No. 6,332,919, U.S. Pat. No. 6,375,317, U.S. Pat. No. 6,287,374, U.S. Pat. No. 6,398,858, U.S. Pat. No. 6,402,825, U.S. Pat. No. 6,468,342, U.S. Pat. No. 6,503,311, U.S. Pat. No. 6,506,245, and U.S. Pat. No. 6,852,156. The disclosures of the preceding references are incorporated herein by reference.

Consistent with the requirements for the particular application, various types of aqueous additives can be used to modify the properties of the ink composition. Surfactant compounds may be used in addition to the peptide reagents describe herein. These may be anionic, cationic, nonionic, or amphoteric surfactants. It is known in the art that certain surfactants may be incompatible with certain ink compositions and may destabilize the pigment dispersion. The choice of a specific surfactant is also highly dependent on the type of print medium substrate to be printed. It is expected that one skilled in the art can select the appropriate surfactant for the specific substrate to be used in the particular ink composition. In aqueous inks, the surfactants may be present in the amount of about 0.01% to about 5% and preferably about 0.2% to about 2%, based on the total weight of the ink. Co-solvents to improve penetration and pluggage inhibition properties of the ink composition may also be added, and in fact are preferred. Such co-solvents are well known in the prior art. Additionally, biocides may be used in the ink compositions to inhibit growth of microorganisms. Sequestering agents such as ethylenediaminetetraacetic acid (EDTA) may also be included to eliminate deleterious effects of heavy metal impurities. Other known additives, such as humectants, viscosity modifiers and other acrylic or non-acrylic polymers may also be added to improve various properties of the ink compositions as desired.

The ink compositions described herein may be prepared in the same manner as other aqueous ink compositions, such as described by Ma et al. in U.S. Pat. No. 5,272,201.

The ink compositions may be applied to a clay-coated paper using methods well known in the art, such as ink jet printing, screen printing, or gravure roll printing.

Additionally, new pigment compounds, coating compounds and methods for making the new compounds, such as coatings for ink jet receiving materials are facilitated by the use of peptide-modified clay materials. The coated ink jet receiving material can provide improved printability, water fastness and reduced spreading. In one embodiment, the print medium is coated with one or more clay-binding peptides, including but not limited to, those having the general structure:

$(CLAYBD_x\text{-}TBD_y)_n$ or $[(CLAYBD_x\text{-}L_s)_q\text{-}(TBD_y\text{-}L_t)_r]_n$ wherein the clay-binding domain has affinity for a clay coating on the print medium and the TBD has affinity for the pigment used in the ink formulation. Then, the print medium is used as a receiving material for the application of the ink.

Additional Applications of Clay-Binding Peptides

Clays treated with peptides comprising binding domains specific for the binding of clays and target binding domains having affinity for other materials may find utility in a variety of other applications. These applications are detailed in the following paragraphs.

Clays are useful for ion exchange and chelation therapy. Coupled with peptides comprising a clay-binding domain and a target binding domain having affinity for a polymer, allows them to be selectively coupled to polymeric supports for extracorporeal therapy. Coupled with other materials, they are more compatible with the gastrointestinal system.

Selective dispersion of water-laden clays in polymeric systems using selective binding peptides allows the manufacture of flame-retardant products.

The use of clay-binding peptides such as those having the general structure:

$(CLAYBD)_n$, $(CLAYBD_x\text{-}BA_p)_n$, $(CLAYBD_x\text{-}L\text{-}BA)_n$, or $[(CLAYBD)_q\text{-}L_x\text{-}(CLAYBD)_r]_n\text{-}L\text{-}BA$, wherein the clay-binding domain has specificity for clay surfaces rather than clay edges allows the manufacture and dispersion of platy kaolin compounds having improved physical properties for use in production of paper products, particularly glossy paper. The compound comprises kaolin having a diameter to thickness of at least 20, indicative of a high degree of exfoliation.

Primary or sedimentary kaolin clay may be purified by providing a dispersed aqueous suspension containing the kaolin particulate material and having at least one selective flocculation polymer having two CLAYBDs at opposite ends of a long tether. The impurities removed by the process include titania, anatase, smectite, iron oxide, and mica.

A process for the accumulation of prions wherein the prions are bioaccumulated on clay and the clay is treated with a clay-binding peptide having a higher binding constant for the clay would allow elution of the prions from the clay as a means of prion accumulation or removal. This could allow a process for the removal of prions from a biological fluid wherein the clay is bound to a support using a tethered CLAYBP having a high affinity for the support. The clay is already known to have a high affinity for prions (see for example, Rigou et al., *Environ. Sci. Technol.* 40(5):1497-1503 (2006)). The clay is treated with a secondary CLAYBP having a lower affinity for the clay to block the random binding of most proteins but which is selectively displaced by prions. The treated clay would be exposed to the biological fluid containing the prions and then the prion-contaminated clay would be disposed. This technology could also lead to a device for the process of removing of prions from a biological fluid.

Clays modified with clay-binding peptides may find use in pharmaceutical applications as an adsorbent, suspending agent, tablet disintegrant and tablet/capsule diluent, or in oily suspension filled capsules to reduce the sedimentation rate of the incorporated powders. Modified clays may also be employed in nutraceutical applications to prevent the alteration of the absorption of orally administered drugs such as amoxicillin, ampicillin, cimetidine, digoxin, lincomycin, phenytoin, and tetracycline There are a wide variety of applications for the peptide-modified clays in agrochemical and agricultural applications. The clays may be coated on seeds to provide a number of beneficial effects during planting. The clays can be modified to provide timed release of insecticides. The modified clays can be modified to act as simple carriers of insecticides and pesticides. The clays may also be modified to selectively bind to chitin so that they selectively bind to insects in close proximity to the seeds. Clays can also be modified to act as carriers of fungicides and biocides or humidity-controlled release of fertilizers and/or herbicides, fungicides or insecticides.

As mined materials, clays show considerable variation from mine to mine and even from different locations within a single mine. These variations include the associated impurities that may be removed by selective complexation with peptides. This is particularly important in food and medicinal grades of clays. This will certainly include the refining of the clays to remove harmful materials as described above. It can also include the incorporation of benefit agents that simply make the clay materials more palatable or add flavorants, etc. It can also include means of binding the clays to other foods such as soy protein to improve texture, processability, appearance, and marketability. The bentonite clays for food applications can be modified to target specific materials in addition to the ion exchange properties of the bentonite. The modified clays may also be useful as bonding agents in animal feeds designed to carry selected benefit agents. Modified clays may be superior for clarifying wine, beer, and vegetable oil; and purifying wastewater. Modified kaolin may be useful in the manufacture of kaolin-coated papers for the manufacture of cigarettes to control burning rates.

The military currently uses fine-particle aluminosilicate for the emergency treatment of severe hemorrhagic wounds. The purpose is to stop the bleed-out until the casualty can be removed to the back lines. The current material is almost purely mechanical in its means of action, but peptide-modified clays may be specifically designed to adhere to tissue to improve the efficacy of the system.

One embodiment disclosed herein provides a method for beneficiating and dewatering a clay. The method comprises the following steps: (a) providing a clay for which beneficiation is desired; (b) forming an aqueous suspension of said clay; (c) deflocculating said aqueous suspension; (d) optionally adding a reducing agent to said deflocculated aqueous suspension; (e) adding a peptide reagent of the general structure:

$$(CLAYBD)_n \text{ or } [(CLAYBD_x\text{-}L_s)_q\text{-}(CLAYBD_y\text{-}L_t)_r]_n$$

where CLAYBD is specific to the clay used in step (a); (f) separating said flocculated clay product from the remainder of the suspension; (g) redispersing the separated clay of (f) to form a deflocculated clay product having a higher weight percent solids content than the deflocculated aqueous suspension of (c); (h) optionally further dewatering or drying said deflocculated clay product.

The aqueous suspension formed in step (b) may be obtained by any method known in the art; for example, by blunging the crude clay feed with water, or by hydrolic mining with use of a monitor, according to known methods. Typically, a dry kaolin may be blunged such that the resulting kaolin/water composition will have a solids concentration of from 30% to 70% by weight.

The deflocculated clay suspension of step (c) may typically be degritted, and optionally further beneficiated, prior step (d) and/or step (e). Degritting may be accomplished according to methods known in the art. Additional beneficiation processes include, but are not limited to, fractionation, classification, floatation, froth floatation, and magnetic separation. The solids concentration of the aqueous suspension may be diluted prior to degritting and fractionation to between about 25% to about 30%. Following other beneficiation procedures, and prior to selective flocculation, the slurry solids concentration will advantageously be reduced further to about 10% to about 20%, preferably about 15%.

The deflocculation in step (c) may be accomplished by any suitable method. For example, the method could comprise the addition of one or more chemical agents capable of increasing the pH of the aqueous suspension sufficient to facilitate deflocculation. Typically the pH will be raised to between 6 and 12, more typically between 7 to 11.5. Agents suitable for adjusting the pH include sodium carbonate, sodium hydroxide, and ammonium hydroxide, or mixtures thereof, but may also include any other dispersing agents capable of performing this function. One or more dispersing agents may also be additionally added to further disperse the deflocculated clay. Such dispersing agents include sodium polyphosphates, sodium silicates, and sodium polyacrylates, but may also include any other dispersing agents capable of performing this function.

The reducing agent referred to in step (d) is used to effect alkaline bleaching. As indicated in the discussion above, it is advantageous to perform alkaline bleaching when the feed clay referred to in step (a) is in need of additional whitening or brightening due to the presence of iron oxide impurities.

The reducing agent referred to in step (d) is preferably added prior to the addition of a high molecular weight polymer to allow time for complete mixing and action by the bleaching agent. The amount of time required will depend on the degree of mixing and other factors, and may readily be determined by those of ordinary skill in the art. Good results have been obtained by waiting from 20 minutes to 3 days, preferably 1-2 hours between adding the reducing agent and the high molecular weight polymer. However, the reducing agent may also be added at the same time, or after the addition of the clay-binding peptide.

The reducing agent in step (d) may be either chemical (organic or inorganic) or microbiological. Preferred chemical reducing agents include sodium hydrosulfite, formamidine sulphinic acid (FAS), thiourea dioxide, and dithionate, but may also include any other chemical reducing agents capable of reducing iron oxides under the conditions prescribed.

Useful microbiological reducing agents include *Aspergillus niger; Enterobacter aerogenes* and *Leuconostoc mesenteroides*, and mixtures thereof, but may also include any other microbiological reducing agents capable of performing the function under the conditions prescribed. Microbiological reducing agents may be used in processes called bioleaching. Bioleaching techniques such as those described by Shelobolina (2000) in the Georgia Geological Society Guidebook, Volume 20, titled *Geology of the Commercial Kaolin Mining District of Central and Eastern Georgia*, may be followed. While bioleaching requires the introduction of bacteria and nutrients, we believe that introduction of a bioleaching stage in place of inorganic or organic chemical reducing agents is made possible by an embodiment disclosed herein because the selective flocculation step (step (e)) enables the separation of clay from contaminants such as iron-bearing organic compounds, bacterial matter, nutrient matter or other residues resulting from the bioleaching process. An oxidative process such as ozone may be required after the selective flocculation process to make the clay product fit for use by preventing microbiological contamination of the product.

The separation between the liquid and flocculated solid referred to in step (f) may be achieved by any manner known in the art. Such separation may be performed using a settling bowl, thickener, centrifuge, hydrocyclone rotary vacuum filter, low pressure filter press, high pressure filter press, or tube press. Use of a thickener or a separator designed for this application is preferred.

The redispersion referred to in step (g) may be accomplished by various methods, depending in part upon the nature of the high molecular weight polymer used. When high molecular weight polymers such as Nalco 9877 (Nalco Co., Naperville, Ill.) are used, the flocculated clay product referred to in step (f) may be subjected to a polymer-destroying amount of at least one chemical or gaseous agent. Such chemical or gaseous agents may advantageously be oxidizing agents. Such chemical oxidizing reagents may include sodium hypochloride, hydrogen peroxide, and potassium permanganate, but may also include any chemical oxidizing agent capable of performing this function. Alternatively, and preferably, the polymer-destroying agent may be an oxidizing gas. Such oxidizing gasses include ozone, but may also include any gaseous oxidizing agent capable of performing this function. When other high molecular weight polymers are used, redispersion may require addition of a chemical dispersant, optionally together with high shear mixing, to redisperse the flocculated clay. The separated, redispersed clay selective flocculation product will have greater than 40% solids, preferably greater than 55%.

As per step (h), the product of step (g) may optionally be further dewatered using a filter press, evaporator, or membrane filter or the like. The product of step (g) may also optionally be further dried using known techniques and machinery, such as an apron dryer, fluid bed dryer, rotary dryer or spray dryer. Further dewatering or back mixing will typically increase the solids content to about 70%. Apron or spray drying may optionally be used to increase solids to above 90%.

Applicants specifically incorporate the entire contents of all cited references in this disclosure. Further, when an amount, concentration, or other value or parameter is given either as a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

EXAMPLES

The methods or materials described herein are further defined in the following Examples. It should be understood that these Examples, while indicating preferred embodiments disclosed herein, are given by way of illustration only. From the above discussion and these Examples, one skilled in the art can ascertain the essential characteristics of methods or materials described herein, and without departing from the spirit and scope thereof, can make various changes and modifications disclosed herein to adapt it to various uses and conditions.

The meaning of abbreviations used is as follows: "min" means minute(s), "sec" means second(s), "h" means hour(s), "μL" means microliter(s), "mL" means milliliter(s), "L" means liter(s), "nm" means nanometer(s), "mm" means millimeter(s), "cm" means centimeter(s), "μm" means micrometer(s), "mM" means millimolar, "M" means molar, "mmol" means millimole(s), "μmole" means micromole(s), "g" means gram(s), "μg" means microgram(s), "mg" means milligram(s), "g" means the gravitation constant, "rpm" means revolutions per minute, "pfu" means plaque forming unit, "BSA" means bovine serum albumin, "PEG" means polyethylene glycol, "ELISA" means enzyme linked immunosorbent assay, "IPTG" means isopropyl β-D-thiogalacto-pyranoside, "A" means absorbance, "$A_{450}$" means the absorbance measured at a wavelength of 450 nm, "TBS" means Tris-buffered saline, "TBST-X" means Tris-buffered saline containing TWEEN® 20 where "X" is the weight percent of TWEEN® 20, "Xgal" means 5-bromo-4-chloro-3-indolyl-beta-D-galactopyranoside, "SEM" means standard error of the mean, "vol %" means volume percent, and "wt %" means percent by weight.

General Methods:

Standard recombinant DNA and molecular cloning techniques used in the Examples are well known in the art and are described by Sambrook, J., and Russell, D., *Molecular Cloning: A Laboratory Manual,* $3^{rd}$ Ed. Cold Spring Harbor Laboratory Press, Cold Spring Harbor, N.Y., 2001, by T. J. Silhavy, M. L. Bennan, and L. W. Enquist, *Experiments with Gene Fusions*, Cold Spring Harbor Laboratory, Cold Spring Harbor, N.Y., 1984, and by Ausubel, F. M. et al., *Short Protocols in Molecular Biology,* $5^{th}$ Ed. Current Protocols and John Wiley and Sons, Inc., N.Y., 2002.

Materials and methods suitable for the maintenance and growth of bacterial cultures are also well known in the art. Techniques suitable for use in the following Examples may be found in *Manual of Methods for General Bacteriology*, Phillipp Gerhardt, R. G. E. Murray, Ralph N. Costilow, Eugene W. Nester, Willis A. Wood, Noel R. Krieg and G. Briggs Phillips, eds., American Society for Microbiology, Washington, D.C., 1994, or by Thomas D. Brock in *Biotechnology: A Textbook of Industrial Microbiology*, Second Edition, Sinauer Associates, Inc., Sunderland, Mass., 1989.

All reagents, restriction enzymes and materials used for the growth and maintenance of bacterial cells were obtained from Aldrich Chemicals (Milwaukee, Wis.), BD Diagnostic Systems (Sparks, Md.), Life Technologies (Rockville, Md.), or Sigma Chemical Company (St. Louis, Mo.), unless otherwise specified.

Example 1 (Prophetic)

Selection of Clay-Binding Peptides Using Phage Display Biopanning

The purpose of this prophetic Example is to describe how to identify phage peptides that bind to clay using a modified phage display biopanning method.

Phage Display Peptide Libraries:

The phage libraries described herein, Ph.D.-12™ Phage Display Peptide Library Kit and Ph.D.-7™ Phage Display Library Kit, are purchased from New England BioLabs (Beverly, Mass.). These kits are based on a combinatorial library of random peptide 7 or 12-mers fused to a minor coat protein (pIII) of M13 phage. The displayed peptide is expressed at the N-terminus of pIII, such that after the signal peptide is cleaved, the first residue of the coat protein is the first residue of the displayed peptide. The Ph.D.-7 and Ph.D.-12 libraries consist of approximately $2.8\times10^9$ and $2.7\times10^9$ sequences, respectively. A volume of 10 μL contains about 55 copies of each peptide sequence. Each initial round of experiments is carried out using the original library provided by the manufacturer in order to avoid introducing any bias into the results.

Biopanning Against a Clay Surface:

The clay sample is Kaogloss 90 which is available from Thiele Kaolin Co. (Sandersville, Ga.). The following protocol is used for biopanning against the clay particles. The clay particles are suspended in a tube filled with 5 mL of 90% isopropanol for 30 min at room temperature and then washed 5 times for 10 min each with deionized water before being collected by vacuum filtration. Then, 5 mL of blocking buffer consisting of 1 mg/mL BSA in TBST containing 0.5% TWEEN® 20 (TBST-0.5%) is added to the tube and incubated for 1 h at 4° C.

The clay particles are filtered and washed 5 times with TBST-0.5% and then 2 mL of TBST-0.5% containing 1 mg/mL BSA is added to the tube. Then, 10 μL of the original phage library ($2\times10^{11}$ pfu), either the 12-mer or 7-mer library, is added to the clay particles and incubated for 15 min at room temperature. The clay particles are filtered and washed 10 times with TBST-0.5%. The clay is then transferred to a clean tube, 2 mL of a non-specific elution buffer consisting of 1 mg/mL BSA in 0.2 M glycine-HCl, pH 2.2, is added to the tube and incubated for 10 min. The clay particles are filtered and washed three more times with the elution buffer and then washed three times with TBST-0.5%. The clay, which has acid resistant phage peptides still attached, is used to directly infect the host cells *E. coli* ER 2738 (New England BioLabs, Beverly, Mass.), for phage amplifications. The clay is incubated with an overnight *E. coli* ER2738 culture diluted 1:100 in LB medium, at 37° C. for 4.5 h. After this time, the cell culture is centrifuged for 30 s and the upper 80% of the supernatant is transferred to a fresh tube, ⅙ volume of PEG/NaCl (20% polyethylene glycol-800, obtained from Sigma Chemical Co. St. Louis, Mo., 2.5 M sodium chloride) is added, and the phage is allowed to precipitate overnight at 4° C. The precipitate is collected by centrifugation at 10,000×g at 4° C. and the resulting pellet is resuspended in 1 mL of TBS. This is the first round of amplified stock. The amplified first round phage stock is then titered according to the method described below. For the next round of biopanning, more than $2\times10^{11}$ pfu of phage stock from the first round is used. The biopanning process is repeated for 3 to 4 rounds depending on the experiments.

After the acid wash steps in the final round of biopanning, the clay is used to directly infect 500 μL of mid-log phase bacterial host cells, *E. coli* ER2738, which are then grown in LB medium for 20 min and then mixed with 3 mL of agarose top (LB medium with 5 mM $MgCl_2$, and 0.7% agarose) at 45° C. This mixture is spread onto a LB medium/IPTG/S-Gal™ plate (LB medium with 15 g/L agar, 0.05 g/L IPTG, and 0.04 g/L S-Gal™) and incubated overnight at 37° C. The black plaques are counted to calculate the phage titer. The single black plaques are randomly picked for DNA isolation and sequencing analysis. The peptide sequences identified will have a high binding affinity for the kaolin clay. This same procedure may be used to identify peptide sequences that bind to other types of clays.

Example 2

Selection of Clay-Binding Peptides Using mRNA-Display Biopanning

The purpose of this prophetic Example is to describe how clay-binding peptides were selected using an mRNA display biopanning method.

mRNA-Display Peptide Libraries:

Methods to make libraries of DNA molecules suitable as starting materials for mRNA-display are well-known in the art (see WO2005/051985). The following procedure was used to identify 27-mer peptides that have a specific affinity for a clay target material (montmorillonite).

Briefly, a library of random nucleic acid molecules (dsDNA) encoding a peptide of desired length was generated. A linear peptide library containing 27 randomized amino acid positions was used ("p27 library"). The DNA molecules were designed to include appropriate 5' and 3' regions for efficient in vitro transcription, translation, purification, and coupling to the MHA-oligonucleotide linker (MHA is 3'-[α-amino-p-methoxy-hydrocinnamido]-3'-deoxy-adenosine).

The DNA encoding the linear peptide library was designed to include a T7 promoter and a tobacco mosaic virus (TMV) translation initiation sequence operably linked to the coding sequence (CDS) (Liu et al., *Methods in Enzymology,* 318: 268-293 (2000)). The CDS was designed to encode: (1) a constant N-terminal flaking region comprising a hexa-histidine tag followed by a flexible linker (italicized) sequence (MHHHHHHSGSSSGSGSG; SEQ ID NO: 199), (2) the randomized 27-mer linear peptide, and (3) a constant C-terminal flanking region (TSGGSSGSSLGVASAI; SEQ ID NO: 200) comprising another flexible linker region (bold) and a C-terminal sequence optimized for efficient coupling to the MHA-oligonucleotide linker (underlined).

In Vitro Transcription

Double stranded DNA as result of the PCR reactions were transcribed into RNA using the RiboMax Express in vitro transcription kit (Promega Madison, Wis.). After incubation for at least 45 min at 37° C., DNase I was added and the incubation continued at 37° C. for additional 30 minutes to degrade all template DNA. The reaction mixture was purified by phenol/chloroform extraction. Then free nucleotides were removed by gel filtration using G25 microspin columns (Pharmacia; Milwaukee, Wis.). Concentration of purified RNA was determined by photometry at 260 nm.

Library Preparation:

Approximately 10 pmol of highly purified RNA was produced by in vitro transcription from the p27 DNA library and purified after DNase I digestion (by phenol/chloroform extraction and gel filtration, methods described below). The 3'-end of the p27 library RNA was modified by attachment of a MHA-linker molecule (as described below) and translated in vitro by means of a rabbit reticulocyte lysate. Covalent fusion products between peptide and coding RNA were purified on magnetic oligo(dT) beads, reverse transcribed, and again purified on a Ni-NTA purification matrix to remove uncoupled RNA and free peptides. About 8 pmol of peptide-RNA-cDNA-fusions were used as input for the first contact with target material during selection round 1.

Chemical Coupling of RNA and MHA-oligonucleotide Linker

Purified RNA was annealed (by heat denaturation for 1 minute at 85° C. and cooling down to 25° C. for 10 minutes) with a 1.5-fold excess of MHA-oligonucleotide linker-$PEG_2$A18 (5'-psoralen-UAG CGG AUG C $A_{18}$ $(PEG-9)_2$ CC-MHA [nucleotides shown in italics represent 2'-O-methyl-derivatives] (SEQ ID NO: 201). The covalent coupling was induced by radiation with UV-light (365 nm) for 15 min at room temperature. Aliquots of this reaction mixture before and after irradiation with UV were analyzed on a 6%-TBE-Urea-polyacrylamidgel to control the coupling efficiency (usually at least 60%).

In Vitro Translation and $^{35}$S-labelling of Peptide-RNA Fusions

Ligated RNA was translated using a rabbit reticulocyte lysate from Promega in presence of 15 μCi $^{35}$S-methionine (1000 Ci/mmole). After a 30 min incubation at 30° C., KCl and $MgCl_2$ were added to a final concentration of 530 mM and 150 mM respectively in order to promote formation of mRNA-peptide-fusions.

Oligo(dT) Purification

For the purification of peptide-RNA-fusions from translation mixtures molecules were hybridized to magnetic oligo (dT) beads (Miltenyi Biotec; Bergisch Gladbach, Germany) in annealing buffer (100 mM Tris-HCl pH 8.0, 10 mM EDTA, 1 M NaCl and 0.25% Triton X-100) for 5 min at 4° C. Beads were separated from the mixture using MiniMACS-filtration columns (Miltenyi Biotec), repetitively washed with 100 mM Tris-HCl pH 8.0, 1 M NaCl, 0.25% Triton X-100 and finally eluted with water. A sample of this reaction was analyzed on 4-20% Tris/glycine-SDS-PAGE; radioactive bands were visualized using a PhosphoroImager.

Reverse Transcription (RT)

The RNAs of Oligo(dT)-purified peptide-RNA-fusions were reverse transcribed using SuperScript II Reverse Transcriptase (Invitrogen, Carlsbad, Calif.) according to the manufacturers recommendations. RT reactions contained about 1.5-fold excess of 3'-ReversePrimer. A sample of this reaction was analyzed on 4-20% Tris/glycine-SDS-PAGE; radioactive bands were visualized using a PhosphorImager.

His-tag Purification

Reverse transcribed mRNA-peptide-fusion molecules were mixed with Ni-NTA-agarose (QIAGEN; Valencia, Calif.) in HBS buffer (20 mM HEPES pH 7.0, 150 mM NaCl, 0.025% Triton X-100, 100 μg/mL sheared salmon sperm DNA, 1 mg/mL BSA) and incubated for 60 min at room temperature under gentle shaking. Ni-NTA was then filtrated and washed with HNT buffer (20 mM HEPES pH 7.0, 150 mM NaCl, 0.025% Triton X-100) containing 5 mM imidazole. Finally peptide-RNA-cDNA-fusions were eluted with 150 mM imidazole in HNT buffer (20 mM HEPES pH 7.0, 150 mM NaCl, 0.025% Triton X-100). A sample of this reaction was analyzed on 4-20% Tris/glycine-SDS-PAGE; radioactive bands were visualized using a PhosphorImager. BSA (final concentration 1 mg/mL) and shared salmon sperm DNA (final concentration 100 μg/mL) were added to the eluates before contacting with target materials during selection step.

Selection by Binding to Target Materials and Washing

A. Incubation of Peptid-RNA-cDNA-fusion Library with Target Material:

Purified peptide-RNA-cDNA-fusions (PROFUSION™ molecules; Adnexus Therapeutics, Waltham, Mass.) after Ni- NTA purification were incubated for 60 minutes at room temperature in 1 mL (final volume) of 20 mM Hepes, pH 7.4, 150 mM NaCl, 1 mg/mL BSA, 100 μg/mL shared Salmon sperm DNA, 0.025% TritonX-100 in presence of DEPC-treated, blocked target material. Input activity of purified peptide-RNA-cDNA-fusions was determined by scintillation measurement.

B. Washing:

Non-binding variants were washed away by one of the following washing procedures listed below:

Washing procedure A: used for washing the target material during round 1:

- 5× 5 sec. each with HNTriton buffer (20 mM Hepes, pH 7.4, 150 mM NaCl, 0.025% Triton-X100)
- 2× 3 min. with 10% shampoo in HNTriton buffer
- 3× 5 sec. each with HNTriton buffer
- 1× 5 sec 150 mM NaCl (for buffer removal before elution with KOH)

Washing procedure B: used for washing the target material during selection round 2-7:

- 2× 5 sec. each with HNTween buffer (20 mM Hepes, pH 7.4, 150 mM NaCl, 0.5% TWEEN®-20)
- 1× 5 min. with 10% shampoo in HNTriton buffer
- 1× 5 sec with HNTween buffer including tube change
- 1× 5 min with 10% shampoo in HNTriton buffer
- 3× 5 sec with HNTween buffer; 1 tube change during the third wash
- 1× 5 sec 150 mM NaCl (for buffer removal before elution with KOH)

The shampoo used in the above washing procedures was a commercially available hair shampoo having the following composition:

| | |
|---|---|
| Water | 51% |
| Ammonium lauryl sulfate | 20% |
| Sodium lauryl ether sulfate | 15% |
| Cocamidopropyl betaine | 7% |
| Cocamide MEA | 2.5% |
| Miscellaneous minor components** | ~4.5% |

**(e.g. various pH adjusters, preservatives, vitamins, chelating agents, dispersants, lubricants, fragrances, and dyes)

Comment on Incubation and Washing Conditions:

Normally during mRNA display selections a low detergent concentration is chosen to have low stringent conditions during up to 6 rounds of selection by keeping the detergent concentration at 0.025% Triton-X100. However, a higher stringency for the target material was applied from the beginning during incubation and washing (see washing procedures). The applied high concentrations of TWEEN®-20 and shampoo are close to the so called "critical micelle concentration" (CMC) allowing the formation of small micelles which might contain more than one peptide-RNA-cDNA-fusion. Since CMC driven aggregation of peptide-RNA-cDNA-fusions are critical for successful selections, higher concentrations of the detergents described above were not used.

cDNA Elution:

cDNAs of binding variants were eluted by incubation of target material in 50 μL of 100 mM KOH at 60° C. for 30 minutes. After centrifugation, supernatant was removed from target material and transferred into a fresh tube. KOH eluates were subsequently neutralized by addition of 1 μL of 1 M Tris/HCl, pH 7.0 and 3.8 μL of 1 M HCl (per 50 μL 100 mM KOH).

Polymerase Chain Reaction (PCR):

After elution in KOH and neutralization, the recovered cDNAs were amplified by quantitative PCR with increasing numbers of amplification cycles (12, 15, 18, 21, 24 and 27 cycles). Products were subsequently analyzed by agarose gel electrophoresis over 2% agarose gels. Optimized conditions (minimal cycle number to get good enrichment of DNA of correct length) were then applied for a preparative PCR reaction and controlled again by agarose gel electrophoresis.

Analytical and preparative PCR reactions were performed in presence of 10 mM Tris-HCl (pH 8.8 at 25° C.), 50 mM KCl, 0.08% Nonidet P40, 2 mM $MgCl_2$, 2.5 mM dNTPs, 1 μM of each forward and reverse primer (5'-TAATACGACTCATAGGGACAATTACTATTTACAATTACAATG-3'; SEQ ID NO: 202) and (5'-AATTAAATAGCGGATGCTACACCAAGACTAGAACCGCTG-3'; SEQ ID NO: 203), ⅕ volume of neutralized cDNA eluate and 0.05 U/μL Taq polymerase (Promega). Temperature program of PCR reaction is given below: Initial denaturation: 90 sec at 94° C.; cycling: 15 sec at 94° C. (denaturation), 20 sec at 60° C. (annealing), 30 sec at 72° C. (extension); post treatment: 3 min at 72° C. (post-treatment); hold at 4° C.

Enrichment of cDNA-RNA-Peptide Fusion Molecules Binding to Clay

Seven rounds of selection were conducted and the relative binding of radioactively labeled cDNA-RNA-peptide fusion molecules to the clay target material was measured. The amount of target used per round was 20 μg (montmorillonite).

Round 1 selection used washing procedure A as described above. Rounds 2-7 used washing procedure B. The relative amount of enrichment (reported as percent enrichment of binding molecules relative to their respective input signals [activity of cDNA-RNA-peptide fusions before contacting with the target material]) is provided in Table 10.

TABLE 10

| Selection Round | Washing Procedure | % Enrichment of cDNA-RNA-peptide fusion molecules having an affinity for montmorillonite clay |
|---|---|---|
| R1 | A | 0.00 |
| R2 | B | 0.02 |
| R3 | B | 0.38 |
| R4 | B | 0.30 |
| R5 | B | 0.12 |
| R6 | B | 2.59 |
| R7[a] | B | 4.11 |

[a]= processed for sequencing

Sequencing of 27-mer Clay-binding Peptides

The cDNA molecules from the enriched pool of clay-binding fusion molecules were isolated and PCR amplified as described above. The sequences of the DNA molecules encoding the clay-binding peptides isolated after the $7^{th}$ round of selection were determined (~30 samples). The corresponding amino acid sequences of the clay-binding peptides are provided in Table 11. Several samples were identified encoding an identical or nearly identical amino acid sequence.

TABLE 11

Enriched Clay-binding Peptides

| Sample(s) | Amino Acid Sequence | SEQ ID NO: |
|---|---|---|
| 1, 3, 14, 23, 29 | GHGSPSNSHHGSKKCDMGNSRAKCKRL | 204 |
| 9, 12, 24, 25 | SDRHNLRNSWSISRHCRRKQGRCLPAH | 205 |
| 6, 28 | KKSNKGHHPSSKGKGPPWSEWDKKNGP | 206 |
| 5[a] | KKSNKGPHPSSKGKGPPWSEWDKKNGP | 207 |
| 4, 11, 21, 27 | VGRHHSKAKQKRPHGGKGQNKN | 208 |
| 13[b] | VGRHHPKAKQKRPHGGKGQNKN | 209 |
| 7, 22, 26 | GRRPRARGRSRRGSTKT | 210 |
| 15, 17 | LGVIRNHVVRGRRHHQHVR | 211 |
| 2 | QPGRPTEVHPELVRKSAYLVNPSEDIR | 212 |
| 8 | HRSEKPKNVKYKRGYWERGNQKKHGPG | 213 |
| 10 | GSHKRRGSYALLRTRGVGRQAELEHLL | 214 |
| 16 | VGEKPRRKSKGAKAKKARTKEEKLPKN | 215 |
| 18 | NKGHKQSGSPRHSNKKEKKTQQKRGQP | 216 |
| 19 | HWGSQHKTGLRNHKRSRRDSLGKRGTD | 217 |
| 30 | KGWGSSSGPPGLTGKALGKGRLKPKKK | 218 |

[a] = sequence nearly identical to the sequence identified in samples 6 and 28. The single amino acid different is underlined.
[b] = sequence nearly identical to the sequences identified in samples 4, 11, 21, and 27. The single amino acid different is underlined.

Example 3 (Prophetic)

Characterization of Clay-Binding Peptide Clones by ELISA

The purpose of this prophetic Example is to describe how to evaluate the clay binding affinity of the selected peptide clones identified by the methods described in Example 1 or Example 2 using enzyme-linked immunosorbent assay (ELISA).

Compressed pellets of the kaolin clay sample are placed in a 96-well apparatus, a Minifold I Dot-Blot System from Schleicher & Schuell, Inc. (Keene, N.H.) and are used as the target. For each clone to be tested, the well is incubated for 1 h at room temperature with 200 μL of blocking buffer, consisting of 2% non-fat dry milk in TBS. The blocking buffer is removed by inverting the systems and blotting them dry with paper towels. The wells are rinsed 6 times with wash buffer consisting of TBST-0.5%. The wells are filled with 200 μL of TBST-0.5% containing 1 mg/mL BSA and then 10 μL (over $10^{12}$ copies) of purified peptide stock are added to each well. A skin-binding phage clone (skin-1) having a skin-binding peptide sequence given as SEQ ID NO:81, serves as the control. The samples are incubated at 37° C. for 15 min with slow shaking. The non-binding peptides are removed by washing the wells 10 to 20 times with TBST-0.5%. Then, 100 μL of horseradish peroxidase/anti-M13 antibody conjugate (Amersham USA, Piscataway, N.J.), diluted 1:500 in the blocking buffer, is added to each well and incubated for 1 h at room temperature. The conjugate solution is removed and the wells are washed 6 times with TBST-0.05%. TMB substrate (200 μL), obtained from Pierce Biotechnology (Rockford, Ill.) is added to each well and the color is allowed to develop for between 5 to 30 min, typically for 10 min, at room temperature. Then, stop solution (200 μL of 2 M $H_2SO_4$) is added to each well and the solution is transferred to a 96-well plate and the $A_{450}$ is measured using a microplate spectrophotometer (Molecular Devices, Sunnyvale, Calif.).

The results will demonstrate that all of the clay-binding peptides tested have a significantly higher binding affinity for clay than the control skin-1 peptide.

Example 4 (Prophetic)

Determination of the Clay-Binding Affinity of Clay-Binding Peptides

The purpose of this prophetic Example is to describe how to determine the affinity of the clay-binding peptides for clay surfaces, measured as $MB_{50}$ values, using an ELISA assay. The term "$MB_{50}$" refers to the concentration of the binding peptide that gives a signal that is 50% of the maximum signal obtained in an ELISA-based binding assay. The $MB_{50}$ provides an indication of the strength of the binding interaction or affinity of the components of the complex. The lower the value of $MB_{50}$, the stronger the interaction of the peptide with the clay substrate.

A clay-binding peptide, identified using the method described in Example 1 or Example 2, is synthesized by Synpep Inc. (Dublin, Calif.). The peptide is biotinylated by adding a biotinylated lysine residue at the C-terminus of the amino acid binding sequence for detection purposes and an amidated cysteine is added to the C-terminus of the sequence.

$MB_{50}$ Measurement of Clay-Binding Peptide:

The $MB_{50}$ measurements of biotinylated peptide binding to clay are done using the 96-well plate format. Compressed pellets of the kaolin clay sample are added to the wells. The wells containing the clay samples are blocked with blocking buffer (SuperBlock™ from Pierce Chemical Co., Rockford, Ill.) at room temperature for 1 h, followed by six washes with TBST-0.5%, 2 min each, at room temperature. Various concentrations of biotinylated, binding peptide are added to each well, incubated for 15 min at 37° C., and washed six times with TBST-0.5%, 2 min each, at room temperature. Then, streptavidin-horseradish peroxidase (HRP) conjugate (Pierce Chemical Co., Rockford, Ill.) is added to each well (1.0 μg per well), and incubated for 1 h at room temperature. After the incubation, the wells are washed six times with TBST-0.5%, 2 min each at room temperature. Finally, the color development and the absorbance measurements are performed as described in Example 3.

The results are plotted as $A_{450}$ versus the concentration of peptide using GraphPad Prism 4.0 (GraphPad Software, Inc., San Diego, Calif.). The $MB_{50}$ values are calculated from Scatchard plots. The results will demonstrate that the clay-binding peptide has a high affinity for the kaolin clay, as indicated by a low $MB_{50}$ value (i.e., less than about $1\times10^{-44}$ M).

Example 5 (Prophetic)

Process for Producing Paper Comprising a Clay and a Clay-Binding Peptide Reagent The purpose of this prophetic Example is to describe how to prepare paper containing a clay filler and a clay-binding peptide reagent.

An aqueous feed (thickstock) is made by blending 10% (on eventual total solids) of calcined clay filler with thermomechanical wood pulp (TMP) to form an aqueous feed suspension having a total solids content of 3.5% and a dry weight ratio of filler:fiber of 1:4, based on total solids. This thickstock is then diluted with whitewater to form a thinstock of consistency of 1%. The thinstock is drained to form a sheet and whitewater, which is collected. The paper sheet is dried and analyzed, as is the resulting whitewater. The first pass retentions are observed.

The clay-binding peptide $(CLAYBP\text{-}L\text{-}TBD)_n$ where CLAYBD is specific to clay, n=1, and TBD is specific to cellulose, may be added at several different points in the process. For example, it may be added to the aqueous feed thickstock containing TMP alone. Alternatively, it may be added to the recycled whitewater, with the addition of clay taking place to the whitewater before combination with the TMP thickstock. Finally, rather than adding the clay-binding peptide during the paper making process, it is possible to utilize clay that has been pretreated with (CLAYBP-L-TBD).

It is expected that adding the (CLAYBP-L-TBD) reagent to the thinstock will improve both fines and filler retention, particularly when the first cellulosics material exposed to the (CLAYBP-L-TBD) is the fines.

Example 6 (Prophetic)

Process for Producing a Clay-Coated Paper

The purpose of this prophetic Example is to describe how to prepare clay-coated paper using a clay-binding peptide reagent.

Three coating formulations A-C are prepared and coated separately or in combination onto a base stock, which is then finished under various coating and finishing conditions. Each coating is formulated according to the recipes below. Formulation A contains the clay and a conventional polymeric binder.

Formulation B contains the clay and $(CLAYBD\text{-}L\text{-}TBD)_n$ where the TBD is specific to cellulose, n=1, and the CLAYBP is specific to the particular clay being employed.

Formulation C contains the clay, a conventional polymeric binder, and $(CLAYBP\text{-}L\text{-}TBD)_n$ where the TBD is specific to a printing ink pigment, n=1, and the CLAYBD is specific to the particular clay being employed.

The coating formulations are then applied to both sides of a base stock paper at a total coating weight of about 5 lbs/ream per side. In this regard, where multiple coatings are applied, the total coating weight is approximately 5 lbs/ream per side. The coating alternatives included: (a) applying a single layer coating on each side of the web with a jet applicator blade metering coater; or (b) applying a first coating layer of 2 lbs/ream on each side with a film coater, followed by a second top coating layer of 3 lbs/ream on each side with a jet applicator blade metering coater. Each of the coated papers is then subjected to calendering with a conventional supercalender. Gloss and other properties of the finished products are measured.

It is expected that the gloss of papers from formulation A and B will be similar, but formulation B will show better adhesion to the paper surface.

It is also expected that the paper coated with formulation C will show higher dye-fastness to the printed pigment than will the paper coated with either formulation B or formulation A.

Example 7 (Prophetic)

Preparation of Clay Intercalates with a Clay-Binding Peptide

The purpose of this prophetic Example is to describe how to prepare a clay intercalate with a clay-binding peptide. Three different processes to prepare clay-peptide intercalates are described.

The clay used is a sodium montmorillonite. The clay binding peptide has the structure CLAYBD, which may be obtained from SynPep.

In the first process, a 2% by weight clay-binding peptide solution is mixed with a 2% clay/water suspension in a ratio sufficient to provide a peptide concentration of at least about 15% based on the dry weight of the clay. The resulting solution is agitated at room temperature.

In the second process, dry clay powder (about 8% by weight moisture) is gradually added to the 2% peptide solution in a ratio sufficient to provide a peptide concentration of at least about 15% based on the weight of the clay. The resulting solution is agitated at room temperature.

In the third process, dry peptide is mixed with dry clay, the mixture is hydrated with water and then extruded.

All three methods of preparation will yield the clay-peptide complexes (intercalates), and the results of the intercalation should not depend on the method of preparation. The uptake of the specific-binding peptide may be measured as by the increase in weight of the isolated and dried clay. The intercalated clays are examined using X-ray diffraction.

For a montmorillonite clay, the d(001) values of 12 Å for no intercalated peptide will be maintained, but will begin to diminish in intensity while 24-25 Å d-spacings will appear and will grow in intensity. These new d-spacings are the result of peptide intercalation between adjacent platelets expanding the spacing with one layer of peptide. These spacings will ultimately be replaced by an even greater d-spacing caused by two layers of peptide between each layer of clay.

Example 8 (Prophetic)

Preparation of an Exfoliated Clay and a Polymer/Platelet Composite

The purpose of this prophetic Example is to describe how to prepare an exfoliated clay, which is then incorporated into polymer/platelet composite.

Intercalated clays are prepared using the three processes described in Example 7. The intercalated clays are then transferred to a nylon-66 melt in an extruder under high-shear conditions to form the polymer/platelet composite.

The resulting polymer/platelet composites are examined using X-ray diffraction. The composites comprising the clay containing two layers of peptide between platelets of clay will show a loss of all diffraction from the clay, indicating complete exfoliation of the clay layers. This is in contrast to clay that has not been treated with the peptide, in which diffraction of the clay will be maintained after dispersion in a polymer melt.

Example 9 (Prophetic)

Refining of Clay Using Clay-Binding Peptides

The purpose of this prophetic Example is to describe how to refine a clay using clay-binding peptides.

An oxidized crude kaolin having an off-white color and containing titania, iron oxides, and other impurities is blunged to 70% solids for 20 min. The pH of the blunged product is adjusted to 7.5 using sodium hydroxide, the sample is diluted to half solids, and classified or degritted. The classified intermediate crude is then subjected to beneficiation methods by adjusting the pH to 11.5 using sodium hydroxide, heating to 60° C., adding the clay-binding peptide (CLAYBD-L-CLAYBD), waiting 30 min for the selective flocculation to occur and then selectively isolating the flocculated product.

A control procedure is to use high molecular weight water-soluble polymers and then adjust the pH to achieve flocculation. When the described process is performed prior to selective flocculation, it is expected that a beneficiated product having superior conductivity (lower levels of salt impurities) and equivalent brightness as compared to the control will be achieved.

Example 11 (Prophetic)

Preparation of Sunscreen Compositions Comprising a Clay-Binding Peptide

The purpose of this prophetic Example is to describe how to prepare a sunscreen composition comprising a clay-binding peptide.

The sunscreen formulation is prepared using the ingredients shown in Table 12.

TABLE 12

| Phase | Ingredient | Function | Wt % |
|---|---|---|---|
| A | Deionized Water | Hydrophilic carrier | 35 |
| A | Propylene Glycol | Humectant | 4 |
| A | Keltrol T (2%) | Thickener | 15 |
| A | Clay-affinity complex (30% solids) | Thickener | 22 |
| A | $TiO_2$ | Particulate Sunscreen | 2 |
| B | Lipomulse 165 | Emulsifier | 2 |
| B | Lipowax D | Emulsifier | 5 |
| B | Finsolv TN | Emollient | 10 |
| B | DC 245 | Fluid Emollient | 4.8 |
| C | Glydant | Preservative | 0.2 |

The clay-affinity complex comprises a clay attached to a clay-binding peptide having the structure: (CLAYBD)-L-(TBD), wherein the TBD has affinity for skin and the linker is selected so that the clay-binding peptide acts as an effective dispersant for the clay.

The formulation is prepared by mixing the components of phase A and heating to 75° C. The components of phase B are mixed together and heated to 75° C. Then phase B is added to phase A. The mixture is allowed to cool to 40° C. and phase C is added. The resulting mixture is homogenized using a homogenizer (Silverson Machines, Inc., Longmeadow, Mass.) for 3 min at 5,000 rpm.

In order to improve the durability of the sunscreen formulation, the titanium dioxide sunscreen may be bound to the clay. In this way the sunscreen is bound to the skin via the affinity complex.

What is claimed is:

1. A peptide reagent having a general structure selected from the group consisting of:

a) $(CLAYBD)_n$;
b) $(CLAYBD_x\text{-}BA_p)_n$;
c) $(CLAYBD_x\text{-}AD_y)_n$;
d) $(CLAYBD_x\text{-}TBD_y)_n$;
e) $[(CLAYBD_x\text{-}L_s)_q\text{-}(TBD_y\text{-}L_t)_r]_n$;
f) $[(CLAYBD_x\text{-}L_s)_q\text{-}(CLAYBD_y\text{-}L_t)_r]_n$;
g) $(CLAYBD_x\text{-}L\text{-}BA)_n$; and
h) $[(CLAYBD)_q\text{-}L_x\text{-}(CLAYBD)_r]_n\text{-}L\text{-}BA$;

wherein:

i) CLAYBD is a clay-binding domain having affinity for a clay moiety;
ii) BA is at least one benefit agent;
iii) AD is at least one active domain incorporated into a clay-binding peptide;
iv) TBD is at least one target binding domain incorporated into a clay-binding peptide;
v) L is a linker molecule;
vi) n, p, x, y, q, and r independently range from 1-20; and
vii) s and t are each independently 0 or 1, provided that both s and t may not be 0 wherein, the clay binding peptide of the clay binding peptide domain (CLAYBD) is selected from the group consisting of SEQ ID NOs: 204-218.

2. An affinity complex between a clay and a peptide reagent having a general structure selected from the group consisting of:

a) $clay_m\text{-}(CLAYBD)_n$;
b) $clay_m\text{-}(CLAYBD_x\text{-}BA_p)_n$;
c) $clay_m\text{-}(CLAYBD_x\text{-}AD_y)_n$;
d) $clay_m\text{-}(CLAYBD_x\text{-}TBD_y)_n$;
e) $clay_m\text{-}[(CLAYBD_x\text{-}L_s)_q\text{-}(TBD_y\text{-}L_t)_r]_n$;
f) $clay_m\text{-}[(CLAYBD_x\text{-}L_s)_q\text{-}(CLAYBD_y\text{-}L_t)_r]_n$;
g) $clay_m\text{-}(CLAYBD_x\text{-}L\text{-}BA)_n$; and
h) $clay_m\text{-}[(CLAYBD)_q\text{-}L_x\text{-}(CLAYBD)_r]_n\text{-}L\text{-}BA$;

wherein:

i) clay is a clay moiety;
ii) CLAYBD is a clay-binding domain having affinity for the clay moiety;
iii) BA is at least one benefit agent;
iv) AD is at least one active domain incorporated into a clay-binding peptide;
v) TBD is at least one target binding domain incorporated into a clay-binding peptide;
vi) L is a linker molecule;
vii) m=the number of clay moieties available for binding;
viii) n=is less than or equal to m;
ix) p, x, y, q, and r independently range from 1-20; and
x) s and t are each independently 0 or 1, provided that both s and t may not be 0 wherein, the clay binding peptide of the clay binding peptide domain (CLAYBD) is selected from the group consisting of SEQ ID NOs: 204-218.

3. A composition comprising the peptide reagent of claim 1.

4. The composition of claim 3 selected from the group consisting of a personal care composition, an aqueous ink composition, and a paper composition.

5. The composition of claim 3, wherein the clay is selected from the group consisting of kaolinites, dickites, nacrites, halloysites, hisingerite smectites, beidellites, pyrophyllites, talc, vermiculites, sauconites, saponites, nontronites, montmorillonites, muscovites, illites, chlorites, amesites, baileychlore, chamosites, clinochlore, kaemmererite, cookeites, corundophilites, daphnites, delessites, gonyerites, nimites, odinites, orthochamosites, penninites, pannantites, rhipidolites, prochlore, sudoites, thuringites, albites, phillipsites, analcites, and gibbsites.

6. The composition of claim 3, wherein the TBD has affinity for a material selected from the group consisting of cellulosic materials, lignin materials and ligno-cellulosic materials.

7. The composition of claim 6, wherein said material is derived from soft-woods or hardwoods woods.

8. The composition of claim 7 wherein the soft-woods or hardwoods woods are selected from the group consisting of pine, spruce, fir, oak, maple, eucalyptus, poplar, beech, and aspen.

9. The composition of claim 8, wherein said one or more wood source is in the form of sawdust, wood chips, or wood flour.

10. The composition of claim 4, wherein the composition is an aqueous ink comprising:

a) an aqueous carrier medium; and
b) a pigment;

wherein said peptide reagent has the general structure:

$(CLAYBD_x\text{-}BA_p)_n$, wherein BA is the pigment; or
ii) $(CLAYBD_x\text{-}TBD_y)_n$; or $[(CLAYBD_x\text{-}L_s)_q\text{-}(TBD_y\text{-}L_t)_r]_n$
wherein the TBD has affinity for the pigment.

11. The composition of claim 4 wherein the composition is a personal care composition wherein the TBD has an affinity for a body surface.

12. The composition of claim 11 wherein the body surface is selected from the group consisting of hair, skin, nails, and teeth.

13. A process for applying a pigment to a clay-coated paper comprising:

a) providing an aqueous ink composition according to claim 10; and b) applying the aqueous ink composition to the clay-coated paper, whereby the clay-binding peptide binds to the clay-coated paper, thereby attaching the pigment to the paper.

14. A process for making paper containing a clay comprising:

a) providing an aqueous thickstock suspension comprising cellulosic fibers, and a specific clay in water;

b) diluting the aqueous thickstock suspension of step (a) with water to form an aqueous thinstock suspension;

c) draining the water from the thinstock suspension to form a sheet;

d) drying the sheet;

e) providing a peptide reagent according to claim 1 and having a general structure:

$(CLAYBD_x\text{-}TBD_y)_n$ or $[(CLAYBD_x\text{-}L_s)_q\text{-}(TBD_y\text{-}L_t)_r]_n$ where CLAYBD has specific binding affinity for the clay used in step (a) and TBD has specific binding affinity for cellulose;

f) adding the peptide reagent of (e) to any of the following:

i) the clay of (a);

ii) the thickstock of (a);

iii) the thinstock of (b);

whereby paper containing day is produced.

15. The process of claim 14 wherein the thickstock contains about 2.5% to about 20% by weight of clay and cellulosic fiber in a dry weight ratio of 10:1 to 1:50.

16. The process of claim 14 wherein the $(CLAYBD_x\text{-}TBD_y)_n$ or $[(CLAYBD_x\text{-}L_s)_q\text{-}(TBD_y\text{-}L_t)_r]_n$ is present in the thickstock at a concentration from about 0.001% to about 5% dry weight based upon the dry weight of the suspension.

17. The process of claim 14 wherein the thinstock is formed in an amount of about 0.02 to about 2% dry weight based upon dry weight of the suspension.

18. The process of claim 14 wherein the water used to dilute the thickstock to thinstock is whitewater recycled from the papermaking process.

19. The process of claim 18 wherein the $(CLAYBD_x\text{-}TBD_y)_n$ or $[(CLAYBD_x\text{-}L_s)_q\text{-}(TBD_y\text{-}L_t)_r]_n$ is present in the whitewater utilized in the dilution of the thickstock to thinstock.

20. A paper made according to the process of claim 14.

21. The paper of claim 20, wherein said paper is a carbonless copy paper.

22. A process for producing a beneficiated and dewatered clay comprising:

(a) providing a clay for which beneficiation is desired;

(b) forming an aqueous suspension of said clay;

(c) deflocculating said aqueous suspension;

(d) adding the peptide reagent of claim 1 having the general structure:

$(CLAYBD)_n$ or $[(CLAYBD_x\text{-}L_s)_q\text{-}(CLAYBD_y\text{-}L_t)_r]_n$ where CLAYBD has specific binging affinity to the clay used in step (a) to produce a flocculated clay product in the suspension; and (e) separating said flocculated clay product from the suspension, wherein a beneficiated and dewatered clay is produced.

23. The process of claim 22 wherein the process further comprises one or more additional steps, alone or in combination, said steps including:

(i) adding a reducing agent to said deflocculated aqueous suspension of step (c);

(ii) redispersing the separated flocculated clay product of step (e) to form a deflocculated clay product having a higher weight percent solids content than the deflocculated aqueous suspension of step (c); and (iii) further dewatering or drying said deflocculated clay product of step (ii).

24. A beneficiated and dewatered clay produced by the process of claim 22.

25. A process for producing a clay-coated paper or paperboard comprising the steps of:

a) providing a base stock;

b) providing a coating formulation comprising a clay and the peptide reagent of claim 1 having the general structure $(CLAYBD_x\text{-}TBD_y)_n$ or $[(CLAYBD_x\text{-}L_s)_q\text{-}(TBD_y\text{-}L_t)_r]_n$, in water;

c) coating at least one side of the base stock with the coating formulation; and d) passing the coated base stock through a calender device whereby a clay-coated paper or paperboard is produced.

26. The process of claim 25 wherein the TBD of the peptide reagent having the general structure $(CLAYBD_x\text{-}TBD_y)_n$ or $[(CLAYBD_x\text{-}L_s)_q\text{-}(TBD_y\text{-}L_t)_r]_n$, has specific binding affinity for cellulose and the CLAYBD has specific binding affinity for the clay.

27. The process of claim 25 wherein the TBD of the peptide reagent having the general structure $(CLAYBD_x\text{-}TBD_y)_n$ or $[(CLAYBD_x\text{-}L_s)_q\text{-}(TBD_y\text{-}L_t)_r]_n$ has specific binding affinity for an ink pigment and the CLAYBD has specific binding affinity for the clay.

28. The clay-coated paper or paperboard produced according to the process of claim 25.

29. A coating formulation comprising:

a) a clay;

b) the peptide reagent of claim 1 having the general structure $(CLAYBD_x\text{-}TBD_y)_n$ or $[(CLAYBD_x\text{-}L_s)_q\text{-}(TBD_y\text{-}L_t)_r]_n$; and c) a solvent.

30. The composition of claim 3, wherein the TBD has affinity for one or more of the following:

a) acrylics or urethanes;

b) natural or synthetic rubbers;

c) silicone materials;

d) a material selected from the group consisting of: chelating agents, colorants, dispersants, emollients, emulsifiers, fragrances, humectants, opacifying agents, preservatives, skin conditioners, and thickeners; or e) a polymer.

31. The peptide reagent of claim 1 or the affinity complex of claim 2 wherein the linker molecule is selected from the group consisting of: a peptide linker and an organic linker.

32. The peptide reagent of claim 1 or the affinity complex of claim 2 wherein the active domain performs a function selected from the group consisting of: a linker, a binding function, a catalytic function, and an antimicrobial function.

33. The peptide reagent according to claim 1 or the affinity complex of claim 2 wherein the target binding domain has affinity for a target selected from the group consisting of pigments, benefit agents, print media, chemical functional groups, body surfaces, and biological analytes.

34. The peptide reagent of claim 1 or the affinity complex of claim 2 wherein the target binding domain binds to a target selected from the group consisting of: proteins, nucleic acids, cells, cell membrane fractions, antibodies, antibody fragments, viral proteins, plant fibers, synthetic fibers, and organic and inorganic complexes.

35. The peptide reagent of claim 1 or the affinity complex of claim 2 wherein the target binding domain is a body surface binding domain.

36. The peptide reagent or an affinity complex according to claim 35 wherein the body surface binding domain binds to a body surface selected from the group consisting of hair, skin, nails and teeth.

37. The peptide reagent of claim 1 or an affinity complex of claim 2 wherein the clay moiety is incorporated into a surface.

38. The peptide reagent or an affinity complex according to claim 37 wherein the surface is selected from the group consisting of paper, a solid support, a bead, a microsphere, a sheet, and a fiber.

39. The peptide reagent or an affinity complex according to claim 38 wherein said surface comprises a dye.

40. The peptide reagent of claim 1 or an affinity complex of claim 2 wherein the clay moiety is comprised within a clay film.

41. The peptide reagent of claim 1 or an affinity complex of claim 2 wherein the clay moiety is comprised within a print medium.

42. The peptide reagent or an affinity complex affinity complex according to claim 41 wherein the print medium is selected from the group consisting of paper, sheets, films, nonwovens and textile fabrics.

43. The composition of claim 3, wherein said composition further comprises a substance selected from the group consisting of: pharmaceuticals, cosmetics, nutraceuticals, cancer treatment agents, markers, colorants, conditioners, fragrances, antibacterial agents, antiviral agents, antifungal agents, anti-cancer agents, vaccines, radiolabels, anti-inflammatory agents, anti-glaucomic agents, anesthetics, anti-neoplastic agents, antibodies, and hormones.

44. A method for binding a substrate comprising at least one clay moiety to a target comprising the steps of:

a) providing a target;

b) providing a surface comprising at least one clay moiety c) providing the peptide reagent of claim 1 having the general structure: $(CLAYBD_x\text{-}TBD_y)_n$ or $[(CLAYBD_x\text{-}L_s)_q\text{-}(TBD_y\text{-}Lt)_r]_n$;

d) contacting the target of (a) with said peptide reagent of (c) thereby forming a complex between said target and said peptide; and e) contacting the complex with the substrate comprising said clay moiety thereby binding said substrate to said target.

45. A method for delivering a benefit agent to a substrate comprising clay or a clay moiety comprising:

(a) providing the peptide reagent according to claim 1 having a benefit agent: and (b) contacting the peptide reagent of (a) with a substrate comprising a clay moiety under conditions whereby the peptide reagent binds to the clay moiety, whereby the benefit agent is delivered to the substrate.

46. The method according to claim 45 wherein the benefit agent is selected from the group consisting of pharmaceuticals, markers, colorants, conditioners and fragrances.

47. A method for adhering two surfaces comprising:

a) providing a first surface comprising clay comprising a first peptide regent according to claim 1 having the general formula: $((CLAYBD_x\text{-}AD1_y)_n$;

(b) wherein:

i) CLAYBD is a clay-binding domain;

ii) AD1 is a first active domain; and iii) x, y, and n independently range from 1-20; and (c) providing a second surface comprising a target molecule comprising a second peptide reagent have the general formula (TBD-AD2) wherein:

i) TBD is a target binding domain; and ii) AD2 is a second active domain having affinity for the first active domain; and (a) juxtaposing the first and second surfaces wherein the first and second peptide reagents adhere to each other through the first and second active domains, whereby the surfaces are adhered.

48. A method for adhering two surfaces comprising:

(a) providing a first surface comprising a first target molecule comprising a first peptide regent having the general formula $(CLAYBD_x\text{-}TBD1_y)_n$ according to claim 1 wherein:

i) TBD1 is a first target binding domain;

ii) CLAYBD is a clay-binding domain; and iii) x, y, and n independently range from 1-20;

(b) providing a second surface comprising a second target molecule comprising a second peptide reagent having the general formula $(CLAYBD_x\text{-}TBD2_y)_n)$ wherein:

i) TBD2 is a second target binding domain;

ii) CLAYBD is a clay-binding domain; and iii) x, y, and n independently range from 1-20; and c) juxtaposing the first and second surfaces in the presence of a clay moiety wherein the first and second peptide reagents adhere to the clay moiety through the clay-binding domain, whereby the surfaces are adhered.

49. The peptide reagent of claim 1 wherein the clay-binding peptide domain is isolated by a process comprising the steps of:

(a) providing a library of combinatorially generated peptides;

(b) contacting the library of (a) with a clay sample to form a reaction solution comprising:

(i) peptide-clay complex;

(ii) unbound clay, and (iii) uncomplexed peptides;

(c) isolating the peptide-clay complex of (b);

(d) eluting the weakly bound peptides from the isolated peptide complex of (c) whereby the clay-binding peptide domain is isolated.

50. A method of producing an intercalated clay comprising:

contacting a clay, having adjacent clay platelets, with a composition comprising a peptide reagent according to claim 1 to achieve intercalation of said peptide reagent between said adjacent clay platelets in an amount sufficient to space said adjacent clay platelets a distance of at least about 10 Å; wherein the peptide reagent comprises a clay-binding domain specific for the clay and the composition comprises at least about 2% by weight of the peptide reagent.

51. The method of claim 50 wherein the peptide reagent is $(CLAYBD_x\text{-}TBD_y)_n$ or $[(CLAYBD_x\text{-}L_s)_q\text{-}(TBD_y\text{-}L_t)_r]_n$.

52. The method of claim 51 wherein the TBD is selective for binding to one or more materials selected from the group consisting of polymers, body surfaces, print media, biological analytes, plant fibers, synthetic fibers, and benefit agents.

53. The product made by the process of claim 50.

54. The personal care composition of claim 11 wherein the composition is selected from the group consisting of skin care compositions, skin cleansing compositions, make-up, facial lotions, cream moisturizers, body washes, bar soaps, bath foam bath salts, body lotions, body mists, foot creams, hand creams, lipstick, eyeshadow, foundation, facial powders, deodorant, sunscreens, shaving cream compositions, nail polishes, shaving lotions, cream depilatories, lotion depilatories, facial masks made with clay materials, blushes, bronzers, concealers, anti-aging products, hydroalcoholic toners, foundations, makeup primers, mascaras, powders, shimmers, paste masks, eyeliners, hair conditioners, hair treatment creams, styling gels, styling foams, hair mousses, hair sprays, set lotions, blow-styling lotions, hair color lotions, and hair relaxing compositions.

55. A process for making a personal-care product composition comprising:

a) providing a solvent comprising water;

b) adding a clay;

c) adding one or more peptide reagents according to claim 1;

d) adding an oil; and e) homogenizing said mixture.

* * * * *

UNITED STATES PATENT AND TRADEMARK OFFICE

CERTIFICATE OF CORRECTION

PATENT NO. : 7,749,957 B2
APPLICATION NO. : 11/696380
DATED : July 6, 2010
INVENTOR(S) : Scott D. Cunningham et al.

It is certified that error appears in the above-identified patent and that said Letters Patent is hereby corrected as shown below:

Column 142, line 61, delete "ii)" before "$(CLAYBD_x - TBD_y)_n$;"

Column 143, line 26, after "cellulose;" insert --and--

Column 146, line 11, delete "(a)" and insert --(d)--

Column 146, line 44, after "(b);" insert --and--

Signed and Sealed this

Sixteenth Day of November, 2010

David J. Kappos

*Director of the United States Patent and Trademark Office*